United States Patent [19]

Castellino et al.

[11] Patent Number: 5,190,756
[45] Date of Patent: Mar. 2, 1993

[54] METHODS AND MATERIALS FOR EXPRESSION OF HUMAN PLASMINOGEN VARIANT

[75] Inventors: Francis J. Castellino, Granger, Ind.; Deborah L. Higgins, San Carlos, Calif.

[73] Assignee: Genentech, Inc., South San Francisco, Calif.

[21] Appl. No.: 752,125

[22] Filed: Aug. 29, 1991

Related U.S. Application Data

[62] Division of Ser. No. 444,584, Dec. 1, 1989, Pat. No. 5,087,572.

[51] Int. Cl.$^5$ .................. C12N 15/58; C12N 9/68; A61K 37/547; A61K 37/62
[52] U.S. Cl. .................. 424/94.64; 435/217; 435/216; 435/226; 514/822
[58] Field of Search .................. 424/94.63, 94.64; 435/215, 216, 217, 188, 174; 514/802, 822

[56] References Cited

U.S. PATENT DOCUMENTS

| 3,943,245 | 3/1976 | Silverstein . |
| 5,087,572 | 2/1992 | Castellino .................. 435/240.2 |

FOREIGN PATENT DOCUMENTS

| 028489 | 5/1981 | European Pat. Off. . |
| 0199574 | 10/1986 | European Pat. Off. . |
| 0201153 | 11/1986 | European Pat. Off. . |
| 0233013 | 8/1987 | European Pat. Off. . |
| 0241209 | 10/1987 | European Pat. Off. . |
| 0292009 | 11/1988 | European Pat. Off. . |
| 0293934 | 12/1988 | European Pat. Off. . |
| 0293936 | 12/1988 | European Pat. Off. . |
| WO8805081 | 7/1988 | PCT Int'l Appl. . |
| WO8810119 | 12/1988 | PCT Int'l Appl. . |

OTHER PUBLICATIONS

Davidson et al., Biochemistry 29:3585 (1990).
McClintock et al., Biochem. Biophys. Res. Comm., 43(3):694 (1971).
Whitefleet-Smith et al., Arch. Biochem. Biophys., 271, 390-399 (1989).
Forsgren et al., FEBS Letts, 213, 254-260 (1987).
Malinowski et al., Biochem., 23, 4243-4250 (1984).
McLean et al., Nature, 330, 132-137 (1987).
Wiman, Eur. J. Biochem., 39, 1-9 (1973).
Castellino & Powell, Methods of Enzymology, 80:365-379 (1981).
Sottrup-Jensen et al., Prog. Chem. Fibrinolysis Thrombolysis, 3:191-209 (1978).
Wiman, Eur. J. Biochem., 76:129-137 (1977).
Violand & Castellino, J. Biol. Chem., 251:3906-3912 (1976).
Castellino, Bioscience, 33:647-650 (1983).
Anderle et al., Haemostasis, 18:(Suppl. 1), 165-175 (1988).
Busby et al., Fibrinolysis, 2:64 (1988) (Suppl. I).
Bajaj & Castellino, J. Biol. Chem., 252:492-498 (1977).

Primary Examiner—Robert A. Wax
Assistant Examiner—Dian Cook
Attorney, Agent, or Firm—Ginger Dreger

[57] ABSTRACT

A cleavage-resistant plasminogen molecule is provided that is conveniently produced in recombinant cells by expression of a nucleic acid sequence encoding the plasminogen molecule. Preferably the plasminogen is a sequence variant with a modification in its two-chain cleavage site. The plasminogen molecule may be purified, acylated, complexed with acylated or non-acylated fibrinolytic enzymes, and formulated into pharmaceutical compositions for use in thrombolytic therapy.

13 Claims, 33 Drawing Sheets

```
                                                                        hinPI
                                                                        hhaI
                                                             fnu4HI     mseI
                                                      sfaNI  bbvI       fspI
      aluI
  701 GAGCTGAATG AAGCCATACC AAACGACGAG CGTGACACCA CGATGCCAGC AGCAATGGCA ACAACGTTGC GCAAACTATT AACTGGGAA CTACTTACTC
      CTCGACTTAC TTCGGTATGG TTTGCTGCTC GCACTGTGGT GCTACGGTCG TCGTTACCGT TGTTGCAAGG CGTTTGATAA TTGACCGCTT GATGAATGAG mspI
      hpaII                                mseI
      scrFI                                aseI                                 sau96I      hinPI   bglII(m.haeIII-)
      aluI ncII                            foki mnlI                            avaII       hhaI   haeIII   mspI
  801 TAGCTTCCCG GCAACAATTA ATAGACTGGA TAAAGTTGCA TGGAGGCGGA CCTTCCGGCT CCTTCCGGCT TGCGCTCGGC CCTTCCGGCT GGCTGGTTTA
      ATCGAAGGGC CGTTGTTAAT TATCTGACCT ATTTCAACGT ACCTCCGCCT GGAAGGCCGA GGAAGGCCGA ACGCGAGCCG GGAAGGCCGA CCGACCAAAT AACGACTATT mspI
      hpaII                thaI     fnu4HI    haeIII                                                     pleI
      nlaIV hphI           bstU     bbvI      sau96I(M.haeIII-)                                          hinfI
  901 ATCTGAGCCC GGTGAGCGTG GTCTCGCGG TATCATTGCA GCACTGGGGC CAGATGGTAA GCCCTCCCGT ATCGTAGTTA TCTACACGAC GGGGAGTCAG
      TAGACTCGGG CCACTCGCAC CCAGAGCGCC ATAGTAACGT CGTGACCCCG GTCTACCATT CGGAGGGCA TAGCATCAAT AGATGTGCTG CCCCTCAGTC
                                                                                 mnlI sau3AI
                  mboI(dam-)              nlaIV
            fokI  dpnI      ddeI          banI mnlI
 1001 GCAACTATGG ATGAACGAAA TAGACAGATC GCTGAGATAG GTGCCTCACT GATTAAGCAT TGGTAACTGT CAGACCAAGT TTACTCATAT ATACTTAGA
      CGTTGATACC TACTTGCTTT ATCTGTCTAG CGACTCTATC CACGGAGTGA CTAATTCGTA ACCATTGACA GTCTGGTTCA AATGAGTATA TATGAAATCT sau3AI
                                                    mboI(dam-)
                                        sau3AI      dpnI
                                        mboI(dam-)  alwI
            mseI                        dpnI        mboII(dam-)                               nlaIII           ddeI
            draI                        xhoII       xhoII                                     bspHI            mseI
            ahaIII          mseI ahaIII alwI hphI   xhoII                                     tcatgaccaa       aatcccttaa cgtgagtttt cgttccactg
 1101 TTGATTTAAA ACTTCATTTT TAATTTAAAA GGATCTAGT GAAGATCCTT TTTGATAATC TCATGACCAA AATCCCTTAA CGTGAGTTTT CGTTCCACTG
      AACTAAATTT TGAAGTAAAA ATTAAATTTT CCTAGATCCA CTTCTAGGAA AAACTATTAG AGTACTGGTT TTAGGGAATT GCACTCAAAA GCAAGGTGAC sau3AI
                             mboI(dam-)
                             dpnI
                             alwI                      thaI
             sau3AI  xhoII                             bstU(M.hhaI-)
             mboI(dam-) alwI mboII(dam-)               hinPI        fnu4HI
      hgaI   dpnI                xhoII                 hhaI         bbvI
 1201 AGCGTCAGAC CCCGTAGAA AGATCAAAGG ATCTTCTTGA GATCCTTTTT TTCTGCGCGT AATCTGCTGC TTGCAAACAA AAAACCACC GCTACCAGCG
      TCGCAGTCTG GGGCATCTTT TCTAGTTTCC TAGAAGAACT CTAGGAAAAA AAGACGCGCA TTAGACGACG AACGTTTGTT TTTTGGTGG CGATGGTCGC
```

Fig.1C.

```
                          sau3AI
                          mboI(dam-)
                          dpnI
                          alwI
                          mspI
                          hpaII          aluI                                                              hinPI
                                                                                                          hhaI
1301 GTGGTTTGTT TGCCGGATCA AGAGCTACCA ACTCTTTTTC CGAAGGTAAC TGGCTTCAGC CGAAGGCAGA TACCAAATAC TGTCCTTCTA GTGTAGCCGT
     CACCAAACAA ACGGCCTAGT TCTCGATGGT TGAGAAAAAG GCTTCCATTG ACCGAAGTCG GCTTCCGTCT ATGGTTTATG ACAGGAAGAT CACATCGGCA haeIII                                                                               fnu4HI
           haeI                                                     mnlI                        bbvI
1401 AGTTAGGCCA CCACTTCAAG AACTCTGTAG CACCGCCTAC ATACCTCGCT CTGCTAATCC TGTTACCAGT GGCTGCTGCC AGTGGCGATA AGTCGTGTCT
     TCAATCCGGT GGTGAAGTTC TTGAGACATC GTGGCGGATG TATGGAGCGA GACGATTAGG ACAATGGTCA CCGACGACGG TCACCGCTAT TCAGCACAGA scrFI                          fnu4HI
     ncII                            bbvI
     mspI          pleI      mspI   hinPI                                                 hgIAI
     hpaII         hinfI     hpaII   hhaI                                                 bsp1286              aluI
1501 TACCGGGGTTG GACTCAAGAC GATAGTTACC GGATAAGGCG GCTGAACGGG GGGTTCGTGC ACACAGCCGA GCTTGGAGCG AACGACCTAC
     ATGGCCCAAC CTGAGTTCTG CTATCAATGG CCTATTCCGC CGACTTGCCC CCCAAGCACG TGTGTCGGCT CGAACCTCGC TTGCTGGATG hinPI
                                 hhaI                                                     mspI
                    ddeI         haeII                                                    hpaII        fnu4HI
1601 ACCGAACTGA GCGTGAGCAT TGAGAAAGCG CCACGCTTCC CGAAGGGAGA AAGGCGGACA GGTATCCGGT AAGCGGCCAG GTCGGAACAG
     TGGCTTGACT CGCACTCGTA ACTCTTTCGC GGTGCGAAGG GCTTCCCTCT TTCCGCCTGT CCATAGGCCA TTCGCCGTCC CAGCCTTGTC hinPI    scrFI(dcm-)  scrFI(dcm-)                                           mnlI                       sfaNI
       hhaI     bstNI        bstNI                                                                taqI
1701 GAGAGCGCAC GAGGGAGCTT CCAGGGGGAA ACGGCTGGTA TCTTTATAGT CCTGTCGGGT TTCGCCACCT CTGACTTGAG CGTCGATTTT TGTGATGCTC
     CTCTCGCGTG CTCCCTCGAA GGTCCCCCTT TGCCGACCAT AGAAATATCA GGACAGCCCA AAGCGGTGGA GACTGAACTC GCAGCTAAAA ACACTACGAG haeIII
                                            scrFI(dcm-)          haeIII
                    hinPI            fnu4HI bstNI                haeI
                    hhaI             thaI   nlaIV haeI                                                nlaIII
1801 GTCAGGGGGG CGGAGCCTAT GGAAAAACGC CAGCAACGCG GCCTTTTTAC GGTTCCTGCC CTTTTGCTCG ACATGTTCTT TCCTGCGTTA
     CAGTCCCCCC GCCTCGGATA CCTTTTTGCG GTCGTTGCGC CGGAAAAATG CCAAGGACGG GAAAACGAGC TGTACAAGAA AGGACGCAAT
              nlaIV
```

Fig. 1D.

```
                                                                                         fnu4HI
                                                                              fnu4HI      bbvI
                                                                              bbvI       hinPI    pleI
              hinfI                              aluI                         fnu4HI     hhaI     hinfI     mnlI
1901 TCCCCTGATT CTGTGGATAA CCGTATTACC GCCTTTGAGT GAGCTGATAC CGCTCGCCGC AGCCGAACGA CCGAGCGGCAG CGAGTCAGTG AGCGAGGAAG
     AGGGGACTAA GACACCTATT GGCATAATGG CGGAAACTCA CTCGACTATG GCGAGCGGCG TCGGCTTGCT GGCTCGCCGTC GCTCAGTCAC TCGCTCCTTC hinPI           thaI
          hhaI            bstU[M.hhaI-]
          haeII           hinPI
          mboII           hhaI                                          aluI
                          thaI       haeIII            mseI            pvuII              mspI
                          bstU[M.hhaI-]    eaeI hinfI  aseI                               hpaII
                                mnlI                                        CAGGTTCCC GACTGGAAAG CGGGCAGTGA
2001 CGGAAGAGCG CCCAATACGC TCCCCGGCG TTGGCCGATT CATTAATCCA GCTGGCACGA CAGGTTTCCC GACTGGAAAG CGGGCAGTGA
     GCCTTCTCGC GGGTTATGCG AGGGGCCGC AACCGGCTAA GTAATTAGGT CGACCGTGCT GTCCAAGGG CTGACCTTTC GCCCGTCACT hinPI                                 nlaIV  scrFI(dcm-)
     hhaI   mseI                           banI   bstNI
            aseI     mnlI
2101 GCGCAACGCA ATTAATGTGA GTTACCTCAC TCATTAGGCA CCCCAGGCTT TACACTTTAT GCTTCCGGCT CGTATGTTGT GTGGAATTGT GAGCGGATAA
     CGCGTTGCGT TAATTACACT CAATGGAGTG AGTAATCCGT GGGGTCCGAA ATGTGAAATA CGAAGGCCGA GCATACAACA CACCTTAACA CTCGCCTATT
```

Fig. 1E.

```
2201 CAATTCACA
     GTTAAGTGT
                                                                                                    nlaIV
                                                                                          sau3AI    kpnI
                                                                                          mboI(dam-)
                                                                                          dpnI      banI
                                                                                     xholI         scrFI
                                                                                     nlaIV        ncII
                                                  pleI                               bamHI        mspI
                                        taqI          mnlI                                        smaI
                                        salI  xbaI   alwI                                         scrFI                                    alu1    taqI
                                        hincII[M.taqI-]                                           ncII   rsaI                              sacI    salI   pflMI
          aluI  sphI    pstI            accI[M.taqI-] hinfI[M.taqI-] avaI[M.hpaII-]              alwI  hpaII                              hgiAI[M.aluI-] hincII[M.taqI-]
          aluI  hindIII nlaIII bspMI                                                                                                      bsp1286[M.aluI-]
                nlaIII                                                                                                                    banII[M.aluI-] accI[M.taqI-]
2211 CAGGAAACAG CTATGACCAT GATTACGCCA AGCTTGCATG CCTGCAGGTC GACTCTAGAG GATCCCCGGG TACCGAGCTC GTCGACCCAC
     GTCCTTTGTC GATACTGGTA CTAATGCGGT TCGAACGTAC GGACGTCCAG CTGAGATCTC CTAGGGGCCC ATGGCTCGAG CAGCTGGGTG
                                                                                                              pmgn cDNA linker start
                                                                                                              end pUC119 vector
                                                                                                                      pmgn mRNA 5'ut start
```

Fig. 1F.

```
                    haeIII
                    haeI
                    eaeI
       bsp1286      balI                                xmnI        mboII                                           mnlI    fokI
2301 TTTCTGGGCA CTGCTGGCCA GTCCCAAAAT GGAACATAAG GAAGTGGTTC TTCTACTTCT TTTATTTCTG AAATCAGGTC AAGGAGAGCC TCTGATGAC
     AAAGACCCGT GACGACCGGT CAGGGTTTTA CCTTGTATTC CTTCACCAAG AAGATGAAGA AAATAAAGAC TTTAGTCCAG TTCCTCTCGG AGACCTACTG
 -19                                  M  E  H  K  E  V  V  L  L  L  L  F  L  K  S  G  Q  G  E  P  L  D  D
                                      start initiation codon, pmgn protein leader sequence          start pmgn amino terminus aluI
            scrFI(dcm-]                     pvuII(M.HI-)                                                      mnlI      ecoRI
            bstNI                ddeI       fnu4HI                            mboII              fnu4HI               mnlI    mboII
                                            bbvI                                                 bbvI
2401 TATGTGAATA CCCAGGGGGC TTCACTGTTC AGTGTCACTA AGAACCAGCT GGGAGCAGGA AGTATAGAAG AATGTGCAGC AAAATGTGAAG GAGGACGAAG
     ATACACTTAT GGGTCCCCCG AAGTGACAAG TCACAGTGAT TCTTGGTCGA CCCTCGTCCT TCATATCTTC TTACACGTCG TTTTACACTC CTCCTGCTTC
  6  Y  V  N  T  Q  G  A  S  L  F  S  V  T  K  Q  L  G  A  G  S  I  E  E  C  A  A  K  C  E  E  D  E  E pstI
           bspMI                                                                            mnlI                  fokI
       hphI     bsmI
2501 AATTCACCTG CAGGGCATTC CAATATATCACA GTAAAGAGCA CATTCTCGT CATTACACAC TATTACCGAC AAAACAGGAA GTCCTCCATA ATCATTAGGA TGAGAGATGT
     TTAAGTGGAC GTCCCGTAAG GTTATAGAGT CATTTCTCGT GTTACACAC TATTACCGAC TTTTGTCCTT CAGGAGTAT TAGTAATCCT ACTCTCTACA
  40 F  T  C  R  A  F  Q  Y  H  S  K  E  Q  C  V  I  H  A  E  N  R  K  S  S  I  I  I  R  M  R  D  V tth111I
                                                   ddeI                                 sfaNI                                      hphI
                                                           mnlI                                                                    sau3AI
                                                                                                                                   mboI(dam-)
                                                                                                                                   dpnI
2601 AGTTTATTT GAAAGAAAG TGTATCTCTC AGAGTGCAAG ACTGGGAATG GAAAGAACTA CAGAGGGACG ATGTCCAAAA CAAAAATGG CATCACCTGT                      alwI
     TCAAAATAAA CTTTCTTTTC ACATAGAGAG TCTCACGTTC TGACCCTTAC CTTTCTTGAT GTCTCCCTGC TACAGTTTT GTTTTTACC GTAGTGGACA
  73 V  L  F  E  K  K  V  Y  L  S  E  C  K  T  G  N  G  K  N  Y  R  G  T  M  S  K  T  K  N  G  I  T  C
                                                          start pmgn protein kringle 1 ddeI
              hphI                                     mnlI          mnlI            mnlI         pstI  hinfI
              hinfI bspMI                                                                            
2701 CAAAAATGGA GTTCCACTTC TCCCCACAGA CCTAGATTCT CACCTGCTAC ACACCCCTCA GAGGGACTGG AGGAGAACTA CTGCAGGAAT CTGCAGACACG
     GTTTTTACCT CAAGGTGAAG AGGGGTGTCT GGATCTAAGA GTGGACGATG TGTGGGGAGT CTCCCTGACC TCCTCTTGAT GACGTCCTTA GACGTCGTTGC
 106 Q  K  W  S  S  T  S  P  H  R  P  R  F  S  P  A  T  H  P  S  E  G  L  E  E  N  Y  C  R  N  P  D  N  D
```

Fig. 1G.

```
          sau96I[dcm-][M.haeIII-]
          haeIII
          sau96I[M.haeIII-]
          nlaIV
          eco109I[dcm-]
          bsp1286[M.haeIII-]
          banII[M.haeIII-]              sau3AI
          apaI scrFI[dcm-]              mbo[dam-]
          nlaIV bstNI                   dpnI
          eco109I                       alwI                                                    mnlI      nlaI
                                                                                                mboII     avaII
2801 ATCCGCAGGG GCCCTGGTGC TATACTACTG ATCCAGAAAA GAGATATGAC TACTGCGACA TTCTTGAGTG TGAAGAGGAA TGTATGCATT GCAGTGGAGA
     TAGGCGTCCC CGGGACCACG ATATGATGAC TAGGTCTTTT CTCTATACTG ATGACGCTGT AAGAACTCAC ACTTCTCCTT ACATACGTAA CGTCACCTCT
140    P  Q  G   P  W  C    Y  Y  T    D  P  E  K   R  Y  D    Y  C  D    I  L  E   C  E  E    E  C  M   H  C  S  G  E
                                                                                              end pmgn protein kringle 1
                                                                                                start pmgn protein kringle 2 scrFI[dcm-]
                                              haeIII pleI
                                              stuI[dcm-]
                                              haeI    hinfI
                                              scrFI[dcm-]
                                   nlaIII     bsmI bstNI     ddeI banII   bsp1286
                                   tthIIII    haeIII bstNI   bstNI                nlaIII
2901 AAACTATGAC GGCAAAATTT CCAAGACCAT GTCTGGACTG GAATGCCAGG CCTGGGACTC TCAGAGCCCA CACGCTCATG GATACATTCC TTCCAAATTT
     TTTGATACTG CCGTTTTAAA GGTTCTGGTA CAGACCTGAC CTTACGGTCC GGACCCTGAG AGTCTCGGGT GTGCGAGTAC CTATGTAAGG AAGGTTTAAA
173    N  Y  D   G  K  I  S   K  T  M   S  G  L    E  C  Q   A  W  D    S  Q  S    P  H  A  H   G  Y  I   P  S  K  F fnu4HI styI                                             hinPI
                                       bbvI  haeIII                                            hhaI
                     mboII              alu I fnu4HI                       hphI                haeII
3001 CCAAACAAGA ACCTGAAGAA GAATTACTGT CGTAACCCCG ATAGGGAGCT GGGGCCTTGG TGTTTCACCA CCGACCCCAA CAAGCGCTGG GAACTTGCCG
     GGTTTGTTCT TGGACTTCTT CTTAATGACA GCATTGGGGC TATCCCTCGA CCCCGGAACC ACAAAGTGGT GGCTGGGGTT GTTCGCGACC CTTGAACGC
206    P  N  K  N    L  K  K    N  Y  C   R  N  P  D    R  E  L   R  P  W   C  F  T  T    D  P  N    K  R  W   E  L  C  D sau96I
                                       nlaIV
              fnu4HI         mboII    avaII                                                 thaI
       fokI   bbvI    mnlI   pfIMI                          alwNI                           bstU
3101 ACATCCCCCG CTGCACAACA CCTCCACCAT CTTCTGGTCC CACCTACCAG TGTCTGAAGG GAACAGGTGA AAACTATCGC GGGAATGTGG CTGTTACCGT
     TGTAGGGGGC GACGTGTTGT GGAGGTGGTA GAAGACCAGG GTGGATGGTC ACAGACTTCC CTTGTCCACT TTTGATAGCG CCCTTACACC GACAATGGCA
240    I  P  R    C  T  T    P  P  S   S  G  P    T  Y  Q   C  L  K  G    T  G  E    N  Y  R   G  N  V  A    V  T  V
              end pmgn protein kringle 2                                   start pmgn protein kringle 3
```

Fig.1H.

```
                    bsp1286
         scrFI         hglAI
         ncII          bsp1286
         mspI                                                                                         fokI                fnu4HI
         hpaII         apaLI    mnlI
3201 GTCCGGGCAC ACCTGTCAGC ACTGGAGTGC ACAGACCCCT CACACACATA ACAGGACACC AGAAAACTTC CCCTGCAAAA ATTTGGATGA AAACTACTGC
     CAGGCCCGTG TGGACAGTCG TGACCTCACG TGTCTGGGGA GTGTGTGTAT TGTCCTGTGG TCTTTTGAAG GGGACGTTTT TAAACCTACT TTTGATGACG
273  S  G  H   T  C  Q  H   W  S  A   Q  T  P   H  T  H  N   R  T  P   E  N  F   P  C  K  N   L  D  E  N   Y  C nlaIII
                       sau96I[M.haeIII-]
                          nlaIV
                          haeIII
                          sau96I[M.haeIII-]
                          nlaIV styI                                              rsaI
                          ecoO109I   nlaIV                                        scaI           pleI
                          bsp1286[M.haeIII-]                                                     hinfI
                          banII[M.haeIII-]
                        apaI  ncoI
                        ecoO109I banI
3301 CGCAATCCTG ACGGAAAAAG GGCCCCATGG TGCCATACAA CCAACAGCCA AGTGCGGTGG GAGTACTGTA AGATACCGTC CTGTGACTCC TCCCCAGTAT
     GCGTTAGGAC TGCCTTTTTC CCGGGGTACC ACGGTATGTT GGTTGTCGGT TCACGCCACC CTCATGACAT TCTATGGCAG GACACTGAGG AGGGGTCATA
306  R  N  P  D   G  K  R   A  P  W   C  H  T  T   N  S  Q   V  R  W   E  Y  C   L  I  P  S   C  D  S   S  P  V  S
                                                                                                           end pmgn protein kringle 3 scrFI(dcm-)    hphI
                                         bstNI          nlaIII                                              mnlI
                              aluI       sau96I[dcm-]   styI
                              ddeI[M.aluI-] avaII[dcm-] ncoI                         aluI        mnlI  fokI
                         nlaIV                          bstXI
3401 CCACGGAACA ATTGGCTCCC ACAGCACCAC CCCTGTGGTC CAGGACTGCT ACCATGGTGA TGGACAGAGC TACCGAGGCA CATCCTCCAC
     GGTGCCTTGT TAACCGAGGG TGTCGTGGTG GGACACCAGG GTCCTGACGA TGGTACCACT ACCTGTCTCG ATGGCTCCGT GTAGGAGGTG
340  T  E  Q   L  A  P   T  A  P  P   E  L  T   P  V  V   Q  D  C   Y  H  G  D   G  Q  S   Y  R  G   T  S  S  T
                                                                start pmgn protein kringle 4 haeIII
                          nlaIV                                                         haeI
                          banI                                              pflMI
                        mspI                                                haeI
                        hpaII     mboII
3501 CACCACCACA GGAAAGAAGT GTCAGTCTTG ACACCACCTG GTCATCTATG ACTCCCAGAA GACCCCAGAA AACTACCCAA ATGCTGGCCT GACAATGAAC
     GTGGTGGTGT CCTTCTTCA CAGTCAGAAC TGTGGTGGAC CAGTAGATAC TGAGGGTCTT CTGGGGTCTT TTGATGGGTT TACGACCGGA CTGTTACTTG
373  T  T  T   G  K  K  C   Q  S  W   S  S  M   T  P  H  R   H  Q  L   T  P  E   N  Y  P  N   A  G  L   T  M  N
```

Fig. 1I.

```
                                                 scrFI[dcm-]
                                                 bstNI
                                                 sau96I[M.haeIII-]                                    rsaI
                                                 nlaIV                                  hgaI          scaI
     pstI  hinfI   sfaNI                         haeIII  ecoO109I
3601 TACTGCAGGA ATCCAGATGC CGATAAAGGC CCCTGTGTT TTACCACAGA CCCCAGCGTC AGGTGGGAGT ACTGCAACCT
     ATGACGTCCT TAGGTCTACG GCTATTTCCG GGGACACAA AATGGTGTCT GGGGTCGCAG TCCACCCTCA TGACGTTGGA
406  Y  C  R  N   P  D  A   D  K  G    P  W  C  F   T  T  D    P  S  V    R  W  E  Y   C  N  L ddeI
3681 GAAAAAATGC TCAGGAACAG
     CTTTTTTACG AGTCCTTGTC
433  K  K  C   S  G  T  E
     end pmnprotein kringle4 mnlI
                                       mnlI                         pleI
                                                                    hinfI      mboII
3701 AAGGAGTGT TGTAGCAACCT CCGGCCTGTTG TCCTGCTTCC AGATGTAGAG ACTCCTTCCG AAGAAGACTG TATGTTTGGG AATGGGAAAG GATACCGAGG
     TTCCTCACA ACATCGTTGGA GGCCGGACAAC AGGACGAAGG TCTACATCTC TGAGGAAGGC TTCTTCTGAC ATACAAACCC TTACCCTTTC CTATGGCTCC
440  A  S  V   A  P  P    P  V  V   L  L  P    D  V  E  T    P  S  E  E   D  C  M  F   G  N  G  K   G  Y  R  G
                                                                      start pmgn protein kringle 5 bsp1286
                                            banII
                          scrFI[dcm-]        scrFI[dcm-]
             hgaI nlaIII  fnu4HI  nlaIV
             ahaII bstNI  bbvI bstNI
3801 CAAGAGGGCG ACCACTGTTA CTGGGACGCC ATGCCAGGAC TGGGCTGCCC AGGAGCCCCA TAGACACAGC ATTTTCACTC CAGAGACAAA TCCACGGGCG
     GTTCTCCCGC TGGTGACAAT GACCCTGCGG TACGGTCCTG ACCCGACGGG TCCTCGGGGT ATCTGTGTCG TAAAAGTGAG GTCTCTGTTT AGGTGCCCGC
473  K  R  A  T  T  V  T  G  T  P   C  Q  D    W  A  A  A   Q  E  P  H   R  H  S    I  F  T  P   E  T  N   P  R  A
```

Fig. 1J.

```
                                                                                                          scrFI[dcm-]
                                                                                                          bstNI
                                                                              sau96I
                                                                              nlaIV
                                                       hphI                   avaII
3901 GGTCTGGAAA AAATTACTG CCGTAACCCT GATGGTGATG TAGGTGGTCC CTGGTGCTAC ACGACAAATC CAAGAAAACT TTACGACTAC TGTGATGTCC
     CCAGACCTTT TTTAATGAC GGCATTGGGA CTACCACTAC ATCCACCAGG GACCACGATG TGCTGTTTAG GTTCTTTTGA AATGCTGATG ACACTACAGG
506  G  L  E  L  N  Y  C  R  N  P  D  G  D  V  G  G  P  W  C  Y  T  T  N  P  R  K  L  Y  D  Y  C  D  V  P
                                                                                                                 mnlI sau96I[M.haeIII-]
     nlaIV
     haeIII
     ddeI       fnu4HI                       mnlI
4001 CTCAGTGTGC GGCCCCTTCA TTTGATTGTG GGAAGCCTCA
     GAGTCACACG CCGGGGAAGT AAACTAACAC CCTTCGGAGT
540  Q  C  A  P  S  F  D  C  G  K  P  Q
     end pmgn protein kringle 5
     "start" pmgn protein protease scrFI[dcm-]                    scrFI[dcm-]
                                                bstNI                          bstNI
                        nlaIV                         sau96I[M.haeIII-]
           nlaIV mboII                                haeIII  bstXI[M.haeIII-]
4041 AGTGGAGCCG AAGAAATGTC CTGGAAGGGT TGTAGGGGGG TGTGTGGCCC ACCCACATTC
     TCACCTCGGC TTCTTTACAG GACCTTCGCA ACATCCCCCC ACACACCGGG TGGGTGTAAG
553  V  E  P  K  K  C  P  G  R  V  V  G  G  C  V  A  H  P  H  S pmgn protein protease activation arg
```

Fig. 1K.

```
              scrFI[dcm-]
              bstNI                                                            nlaIV
              sau96I[dcm-][M.haeIII-]                                          banI
              haeIII         ddeI              bsmI                            mnlI       ecoRV           hincII      fnu4HI
                                                                                                                     bbvI  pflMI
4101 CTGGCCCTGG CAAGTCAGTC TTAGAACAAG GTTTGGAATG CACTTCTGTG GAGGCACCTT GATATCCCCA GAGTGGGTGT TGACTGCTGC CCACTGCTTG
     GACCGGGACC GTTCAGTCAG AATCTTGTTC CAAACCTTAC GTGAAGACAC CTCCGTGGAA CTATAGGGGT CTCACCCACA ACTGACGACG GGTGACGAAC
573   W  P  W  Q  V  S  L   R  T  R   F  G  M    H  F  C  G   G  T  L    I  S  P  E  W  V  L  T  A  A  H  C  L stuI                             hgiAI
              haeI haeIII                      scrFI[dcm-]
              styI haeIII                      bstNI bsp1286
                             fokI              apaLI                  hinfI taqI         nlaIII
4201 GAGAAGTCCC CAAGGCCTTC ATCCTACAAG GTCATCCTGG GTGCACACCA AGAAGTGAAT CTCGAACCGC ATGTTCAAGA AATAGAAGTG TCTAGGCTGT
     CTCTTCAGGG GTTCCGGAAG TAGGATGTTC CAGTAGGACC CACGTGTGGT TCTTCACTTA GAGCTTGGCG TACAAGTTCT TTATCTTCAC AGATCCGACA
606   E  K  S  P  R  P  S   S  Y  K   V  I  L  G   A  H  Q    E  V  N   L  E  P  H   V  Q  E   I  E  V   S  R  L  F bsp1286
              banII              ddeI[M.aluI-]
              nlaIV              espI
                                 aluI                                                       aluI      fokI
4301 TCTTGGAGCC CACACGAAAA GATATTGCCT TGCTAAAGCT AAGCAGTCCT GCCGTCATCA CTGACAAAGT GACTGTTTCA TGTCTGCCAT CCCCAAATTA
     AGAACCTCGG GTGTGCTTTT CTATAACGGA ACGATTTCGA TTCGTCAGGA CGGCAGTAGT GACTGTTTCA CTGACAAAGT ACAGACGGTA GGGGTTTAAT
640   L  E  P  T  R  K   D  I  A  L   L  K  L  S   S  P  A   V  I  T   D  K  V   I  P  A   C  L  P  S   P  N  Y sau96I
              avaII[M.hpaII-]
              rsrII                                                haeIII
              mspI                                                 haeI
              hpaII                                     styI rsaI  aluI econI                     aluI
4401 TGTGGTCGCT GACCGGACCG AATGTTTCAT CACTGGCTGG GGAGAAACCC AAGGTACTTT TGGAGCTGGC CTTCTCAAGG AAGCCCAGCT CCCTGTGATT
     ACACCAGCGA CTGGCCTGGC TTACAAAGTA GTGACCGACC CCTCTTTGGG TTCCATGAAA ACCTCGACCG GAAGAGTTCC TTCGGGTCGA GGGACACTAA
673   V  V  A  D  R  T  G   C  F  I   T  G  W   E  T  Q   G  T  F   G  A  G   L  K  E  A  Q   L  P  V  I mspI[M.haeIII-]
              pleI                                                                     hpaII          hphI
              hinfI                                                                    haeIII         scrFI[dcm-]
              mboI                                                                     eaeI mnlI      bstNI
4501 GAGAATAAAG TGTGCAATCG CTATGAGTTT CTGAATGAA GAGTCCAATC CACCGAACTC TGTGCTGGGC ATTTGGCCCG AGGCACTGAC AGTTGCCAGG
     CTCTTATTTC ACACGTTAGC GATACTCAAA GACTTACTT CTCAGGTTAG GTGGCTTGAG ACACGACCCG TAAACCGGGC TCCGTGACTG TCAACGGTCC
706   E  N  K  V  C  N  R   Y  E  F   F  L  N  G   R  V  Q   S  T  E   L  C  A  G  H   L  A  G  T  D   S  C  Q  G
```

Fig. 1L.

```
                                                                hgiAI
                                                                bsp1286                    scrFI[dcm-]
                                        pleI                    apaLI                      bstNI
      sau96I                            hinfI                                                      hphI
      avaII                                                                                        pleI    mnlI
      ppuMI                                                                              hgaI      hinfI[M.hphI-]
      ecoO109I                                            mseI
      mnlI mnlI          taqI                             aseI
4601 GTGACAGTGG AGGTCCTCTG GTTTGCTTCG AGAAGGACAA ATACATTTTA CAAGGAGTCA CTTCTTGGGG TCTTGGCTGT GCACGCCCCA ATAAGCCTGG
     CACTGTCACC TCCAGGAGAC CAAACGAAGC TCTTCCTGTT TATGTAAAAT GTTCCTCAGT GAAGAACCCC AGAACCGACA CGTGCGGGGT TATTCGGACC
 740  D  S  G   G  P  L   V  C  F  E   K  D  K    Y  I  L   Q  G  V  T   S  W  G    L  G  C    A  R  P  N   K  P  G mnlI
4701 TGTCTATGTT CGTGTTTCAA GGTTTGTTAC TTGGATTGAG GGAGTGATGA GAAATAATTA ATTGGACGGG AGACAGAGTG ACGCACTGAC TCACCTAGAG
     ACAGATACAA GCACAAAGTT CCAAACAATG AACCTAACTC CCTCACTACT CTTTATTAAT TAACCTGCCC TCTGTCTCAC TGCGTGACTG AGTGGATCTC
 773  V  Y  V   R  V  S  R   F  V  T   W  I  E   G  V  M  R   N  N
                                                                     end of pmgn protein sequence
                                                                     start pmgn mRNA 3' ut nlaIII                                     tth111I
              sphI                                       mboII              aluI   aluI        mnlI
4801 GCTGGAACGT GGGTAGGGAT TTAGCATGCT GGAAATAACT GGCAGTAATC AAACGAAGAC ACTGTCCCCA GCTACCAGCT ACGCCAAACC TCGGCATTTT
     CGACCTTGCA CCCATCCCTA AATCGTACGA CCTTTATTGA CCGTCATTAG TTTGCTTCTG TGACAGGGGT CGATGGTCGA TGCGGTTTGG AGCCGTAAAA
```

Fig. 1M.

```
                            hinfI         hphI       aluI            mseI
4901 TTGTGTTATT TTCTGACTGC TGGATTCTGT AGTAAGGTGA CATAGCTATG ACATTGTTA AAAATAAACT CTGTACTTAA
     AACACAATAA AAGACTGACG ACCTAAGACA TCATTCCACT GTATCGATAC TGTAAACAAT TTTATTTGA GACATGAATT
                                                                                  rsaI  mseI 4981 CTTTGAAAAA AAAAAAAAA
     GAAACTTTTT TTTTTTTTT
     end pmgn mRNA 3'ut
     start pmgn mRNA poly(A)+

5001 AAAAAAAAA AAAAAAAAAA AAAAAAAAAA AAAAAAAA
     TTTTTTTTT TTTTTTTTTT TTTTTTTTTT TTTTTTTT taqI
           aluI
           sacI   ecoRI
           hglAI[M.aluI-]
       taqI bsp1286[M.aluI-]
       salI banII[M.aluI-]            haeIII
       hincII[M.taqI-]                 eaeI
       accI[M.taqI-]
5071 AAAAGGTCGA CGAGCTCGAA TTCTACTGGC
     TTTTCCAGCT GCTCGAGCTT AAGATGACCG
     end pmgn mRNA poly (A)+
     start pUC119 vector
     end pmgn cDNA 127 linker
```

Fig. 1N.

```
                                     scrFI[dcm-]           fnu4HI          aluI
                                     bstNI         mseI    bbvI    fokI    pvuII
5101 CGTCGTTTA CAACGTCGTG ACTGGGAAAA CCCTGGCGTT ACCCAACTTA ATCGCCTTGC AGCACATCCC CCCTTCGCCA GCTGGCGTAA
     GCAGCAAAAT GTTGCAGCAC TGACCCTTTT GGGACCGCAA TGGGTTGAAT TAGCGGAACG TCGTGTAGGG GGGAAGCGGT CGACCGCATT
     sau96I[M.haeIII-]
       haeIII
         mnlI
           mboII
5191 TAGCGAAGAG
     ATCGCTTCTC
                                                 hinPI
                                                 hhaI
                                                  nlaIV
                                                  narI
                                                  haeII
                      sau3AI                      banI         sfaNI
                      mbo[dam-]                   ahaII[M.hhaI-]
                      dpnI            bglI                                                   sfaNI
                      pvuI
5201 GCCCGCACCG ATCGCCCTTC CCAACAGTTG CGTAGCCTGA ATGGCGAATG GCGCCTGATG CGGTATTTTC TCCTTACGCA TCTGTGCGGT ATTTCACACC
     CGGGCGTGGC TAGCGGGAAG GGTTGTCAAC GCATCGGACT TACCGCTTAC CGCGGACTAC GCCATAAAAG AGGAATGCGT AGACACGCCA TAAAGTGTGG
```

Fig. 10.

```
                   hinPI                                          fnu4HI
                   hhaI                          fnu4HI           bbvI
                   thaI               hinPI      thaI             hinPI
                   bstU[M.hhaI-]      hhaI      hinPI             hhaI          hinPI
            rsaI            fnu4HI    msaI bstU[M.hhaI-] hhaI     thaI          hhaI
                                                                  bstU[M.hhaI-] haeII
5301 GCATACGTCA AAGCAACCAT CTGTAGCGGC GCATTAAGCG CGGGGGGTGT GGTGGTTACG CGCAGCGTGA CCGCTACACT TGCCAGCGCC
     CGTATGCAGT TTCGTTGGTA GACATCGCCG CGTAATTCGC GCCCCCCACA CCACCAATGC GCGTCGCACT GGCGATGTGA ACGGTCGCGG hinPI                                                        mspI                       nlaIV
     hhaI                                                         hpaII                      bsp1286
     haeII           mboII                                        naeI          alul         banII
5401 CTAGCGCCCG CTCCTTTCGC TTTCTTCCCT TCCTTTCTCG CCACGTTCGC CGGCTTTCCC CGTCAAGCTC TAAATCGGGG GCTCCCTTTA
     GATCGCGGGC GAGGAAAGCG AAAGAAGGGA AGGAAAGAGC GGTGCAAGCG GCCGAAAGGG GCAGTTCGAG ATTTAGCCCC CGAGGGAAAT mnlI
          nlaIV                                        haeIII
          banI  taqI                          hphI     draIII sau96I[M.haeIII-]              nlaIV
5501 TTAGTGCTTT ACGGCACCTC GACCCCAAAA AACTTGATTT GGGTGATGGT TCACGTAGTG GCCATCGCC CTGATAGACG GTTTTTCGCC CTTTGACGTT
     AATCACGAAA TGCCGTGGAG CTGGGGTTTT TTGAACTAAA CCCACTACCA AGTGCATCAC CGGTAGCGG GACTATCTGC CAAAAGCGG GAAACTGCAA pleI
     hinfI      mseI                                              avaI
5601 GGAGTCCACG TTCTTTAATA GTGGACTCTT CTCGGGCTAT TCTTTGATT TATAAGGGAT TTTGCCGATT
     CCTCAGGTGC AAGAAATTAT CACCTGAGAA GAGCCCGATA AGAAACTAA ATATTCCCTA AAACGGCTAA
```

Fig. 1P.

```
                                                                                        thaI                 hgiAI        rsaI
                                                                                        bstU                 bsp1286 ddeI
                                      aluI       mseI         mseI  sspI mseI                                apaLI
       haeIII      mseI                                TAACAAAAAT TTTAACAAA ATATTAACGT TTACAATTT ATGGTGCACT CTCAGTACAA
5701   TCGGCCTATT GGTTAAAAAA TGAGCTGATT TAACAAAAAT TTTAACAAA ATATTAACGT TTACAATTT ATGGTGCACT CTCAGTACAA
       AGCCGGATAA CCAATTTTTT ACTCGACTAA ATTGCGCTT TATAATTGCA AATGTTAAAA TACCACGTGA GAGTCATGTT hinPI
                                                                    hinPI            hhaI
             fnu4HI                                                 fnu4HI           thaI
         sfaNI      mseI                          tthIIII nlaIII    hhaI             bstU[M.hhaI-]
                                                                                               hgaI
5801   TCTGCTCTGA TGCCGCATAG TTAAGCCAAC TCCGCTATCG CTACGTGACT GGGTCATGGC TGCGCCCCGA CACCCGCCAA CACCCGCTGA CGGCGCCCTGA
       AGACGAGACT ACGGCGTATC AATTCGGTTG AGGCGATAGC GATGCACTGA CCCAGTACCG ACGCGGGGCT GTGGGCGGTT GTGGGCGACT GCGCGGGACT thaI
                                                                                                            bstU[M.hhaI-]
                     sfaNI                                                                                  hinPI
                                             scrFI                                                          hhaI
                        mspI                 ncII   fnu4HI                                                  thaI mnII
                        hpaII                mspI   bbvI                                                    bstU[M.hhaI-]
                        scrFI         aluI   hpaII aluI nlaIII      mnlI     hphI
                        ncII fokI
5901   CGGGCTTGTC TGCTCCCGGC ATCCGCTTAC AGACAAGCTG TGACCGTCTC CGGGAGCTGC ATGTGTCAGA GGTTTTCACC GTCATCACCG AAACGGCGA
       GCCCGAACAG ACGAGGCCG TAGGCGAATG TCTGTTCGAC ACTGGCAGAG GCCCTCGACG TACACAGTCT CCAAAAGTGG CAGTAGTGGC TTTGCCGCT

6001   GGCAGTATTC
       CCGTCATAAG
```

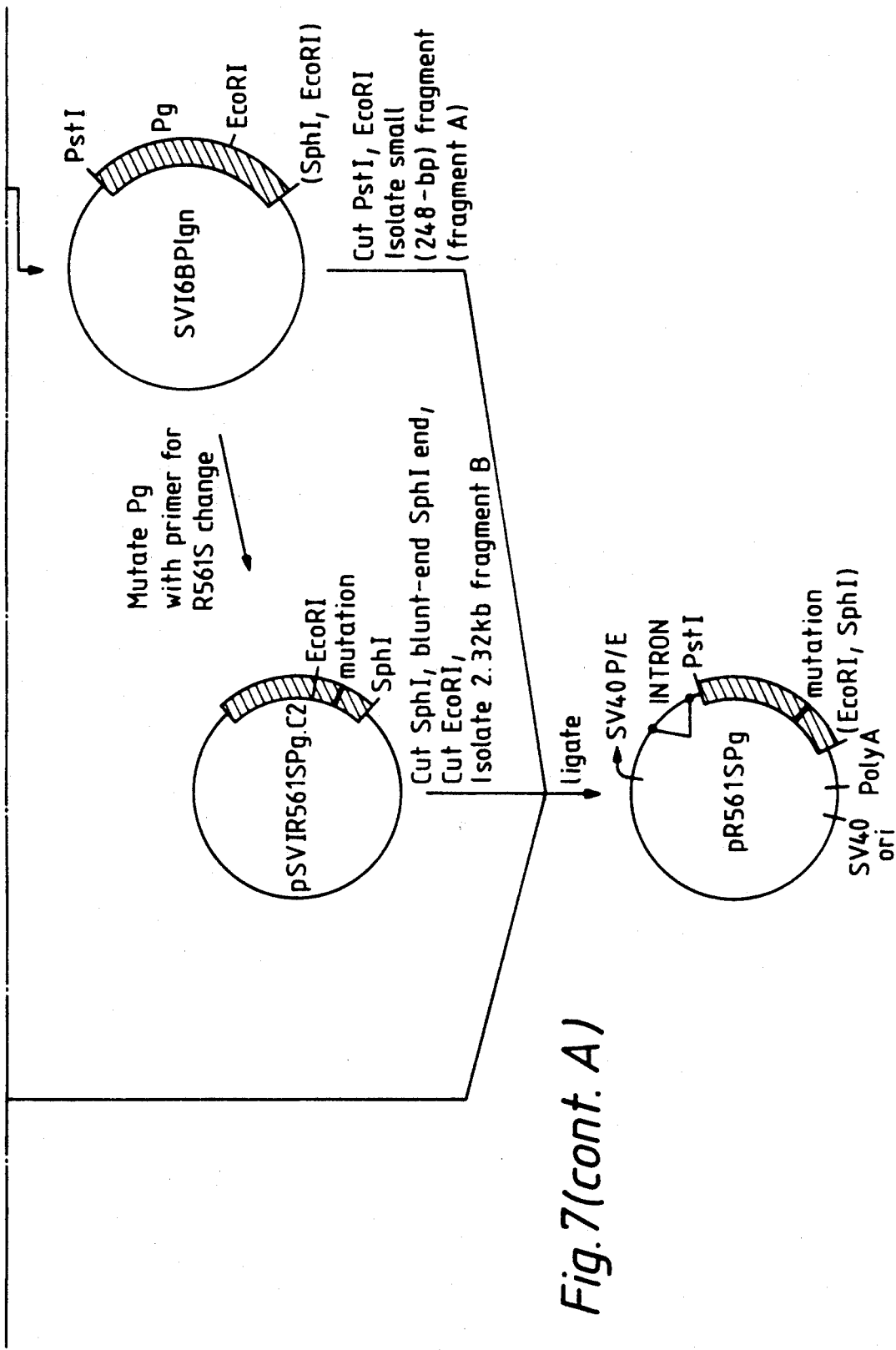
Fig.7(cont. A)

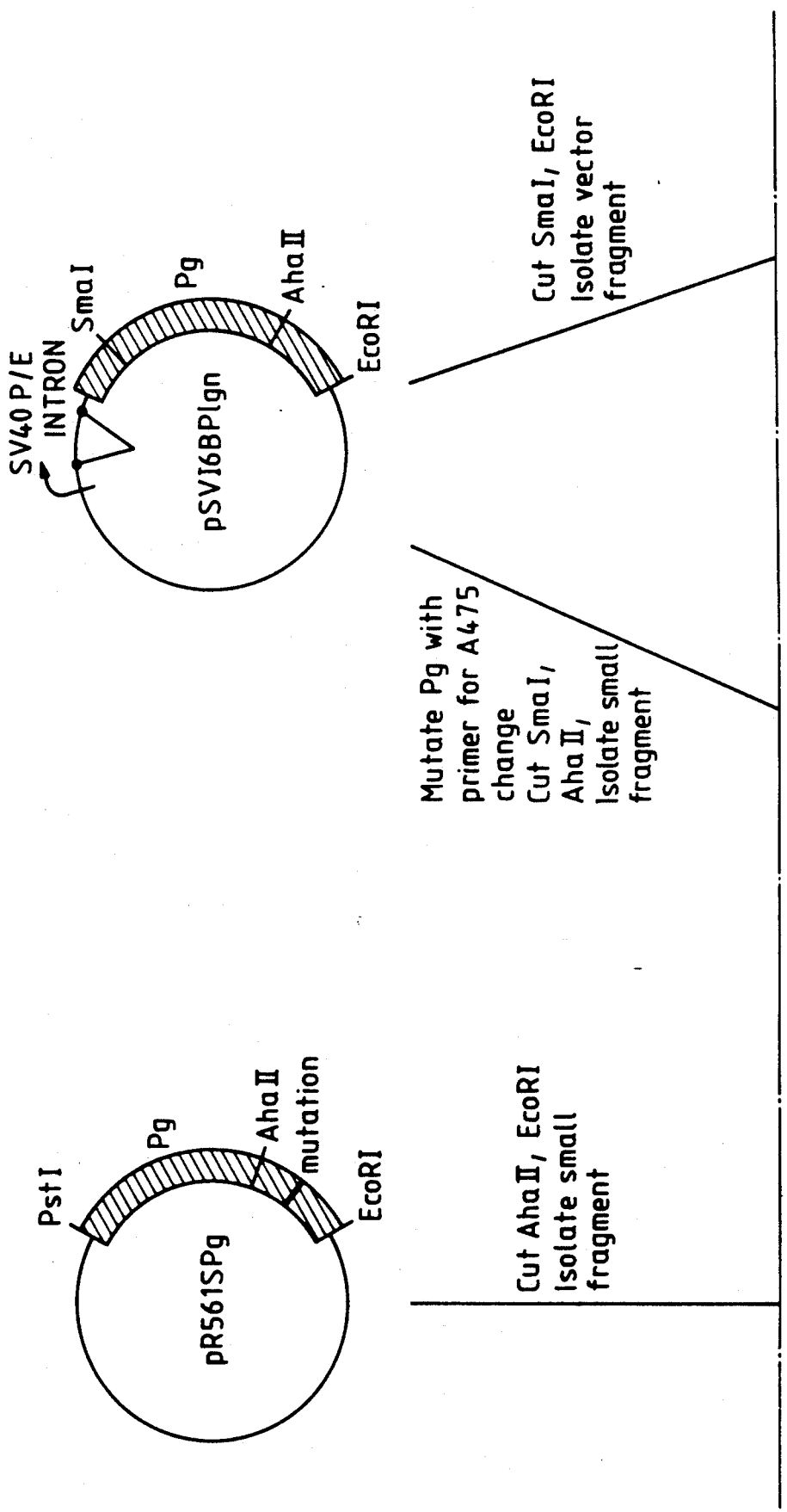
Fig.7(cont.B)

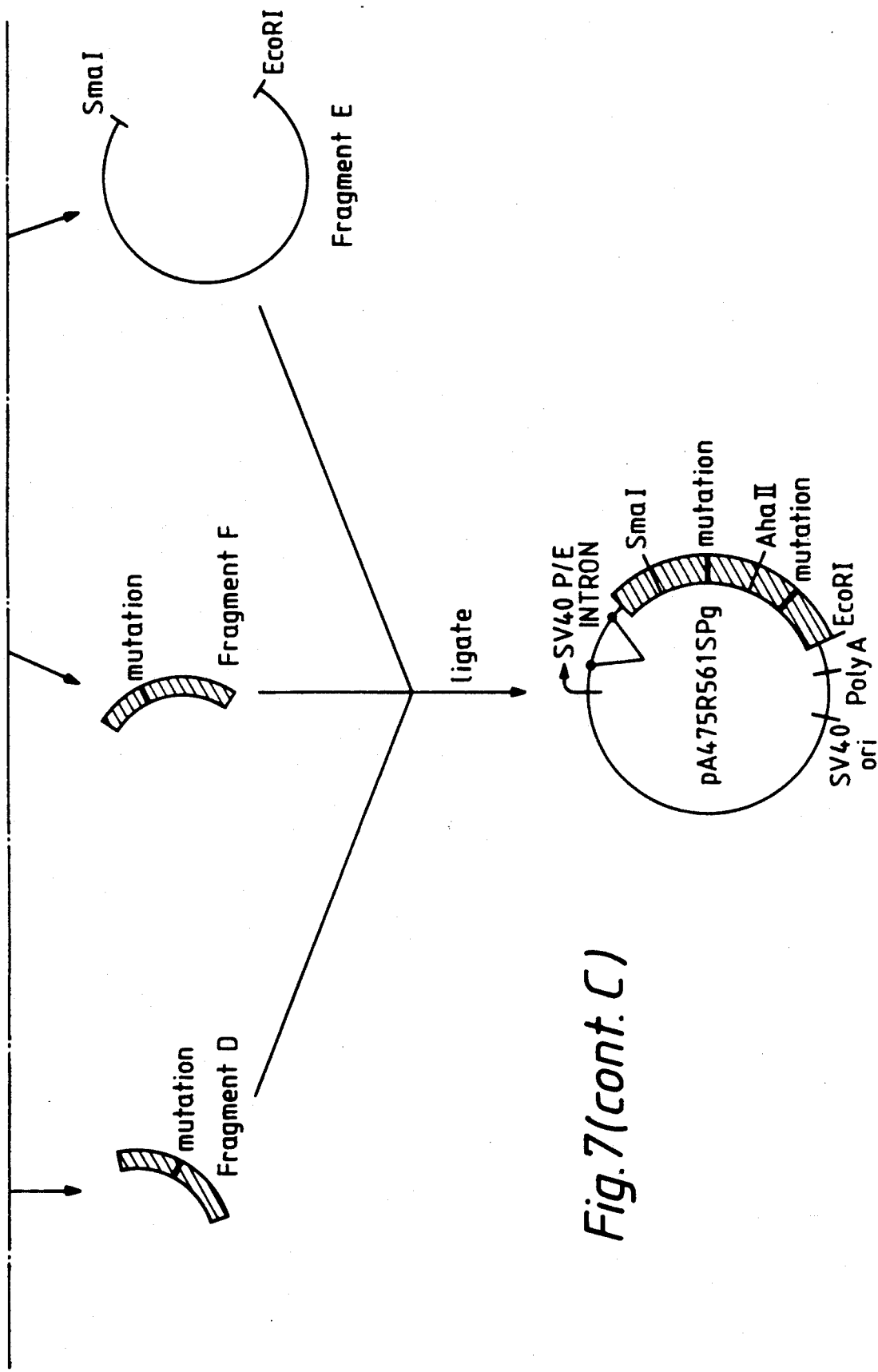
Fig.7(cont.C)

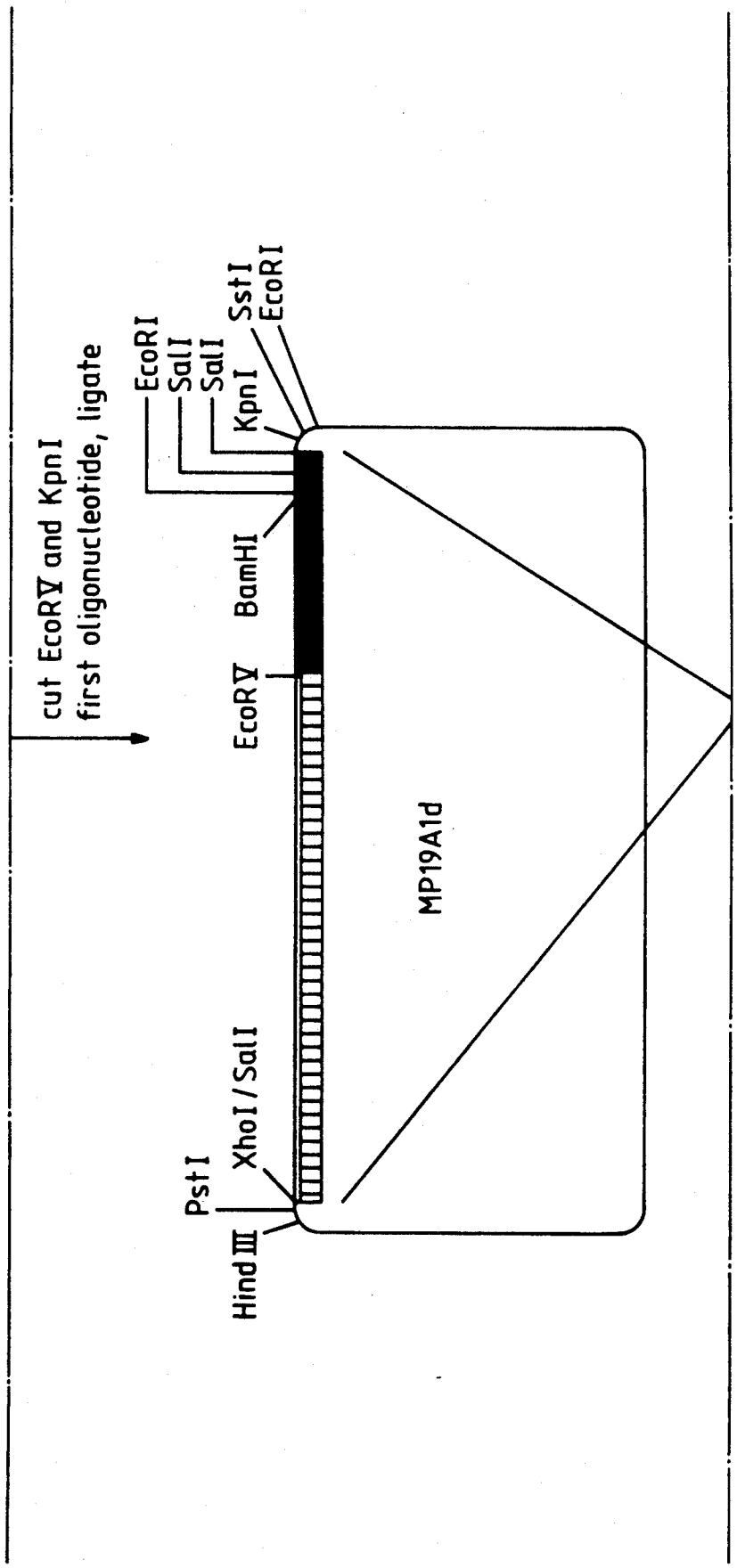
Fig. 8 (cont. A)

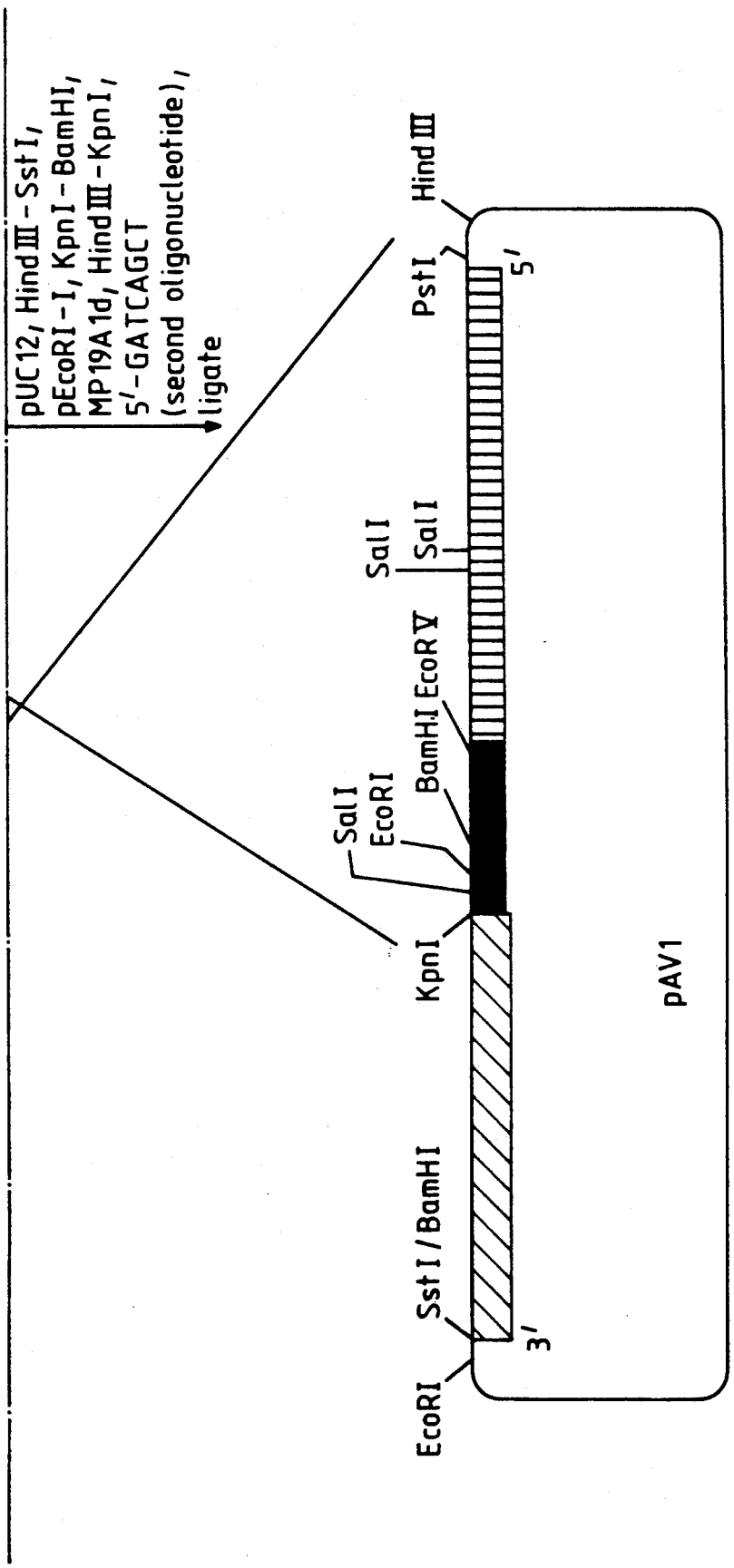
Fig. 8(cont. B)

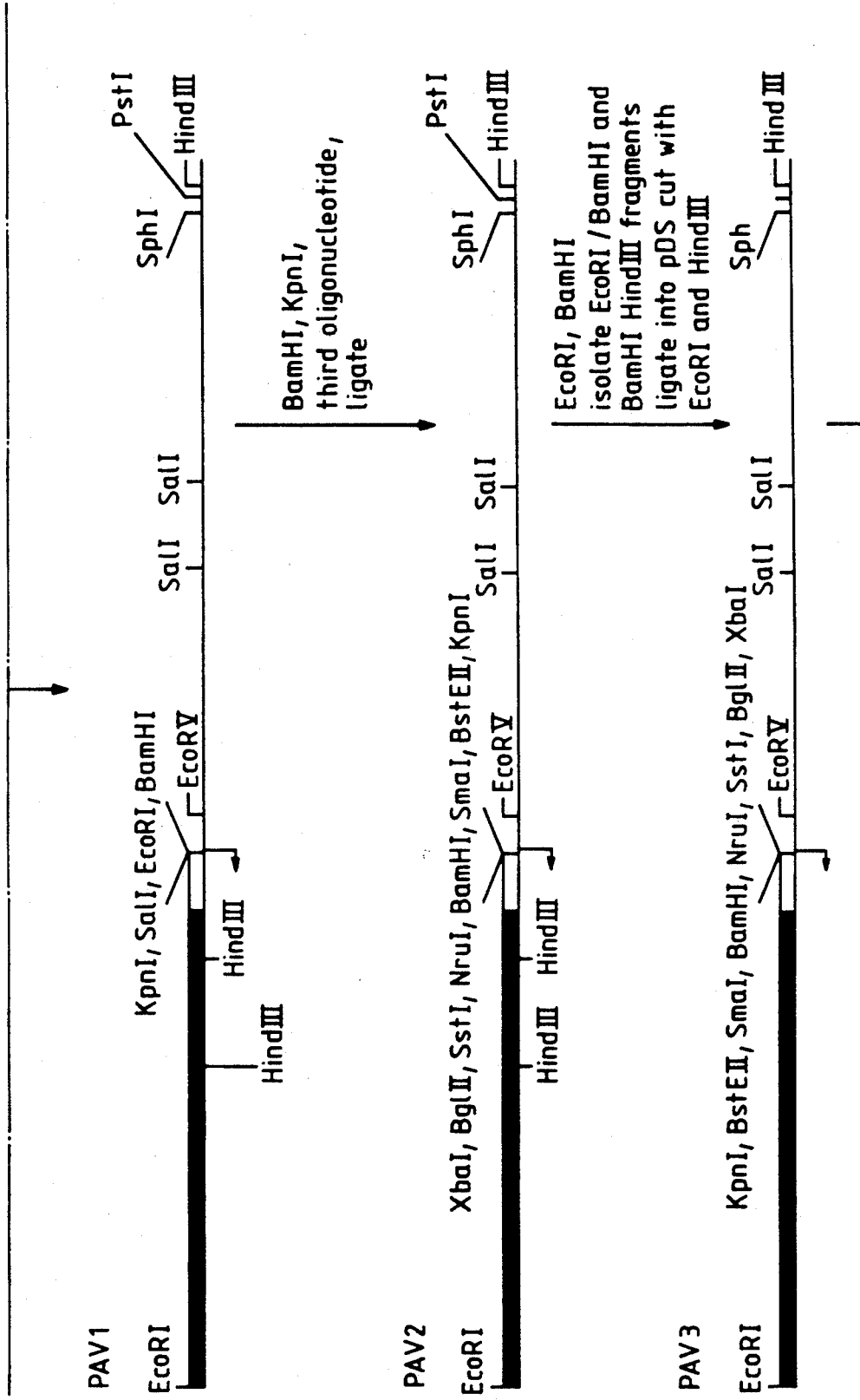
Fig. 8 (cont. C)

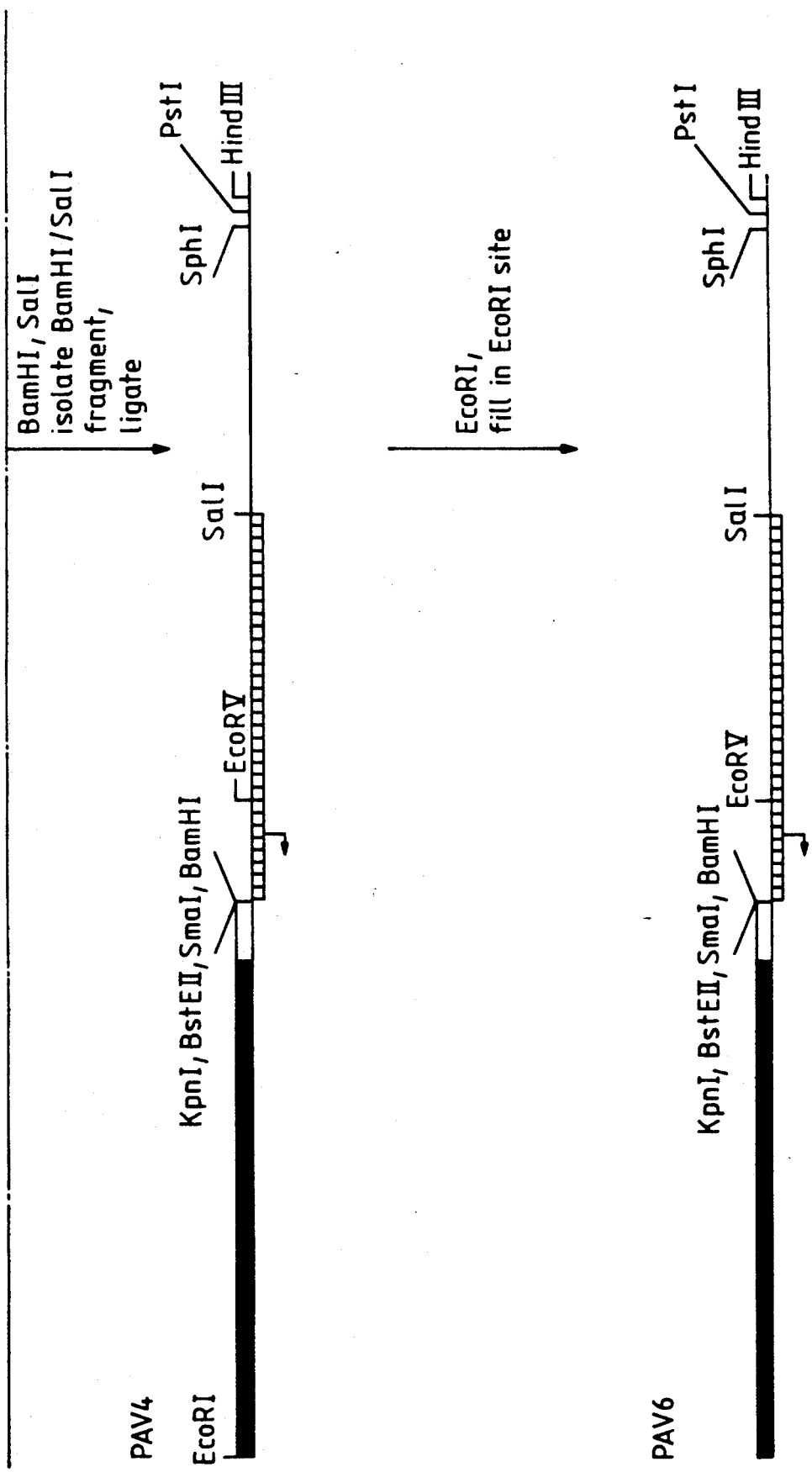
Fig.8(cont.D)

METHODS AND MATERIALS FOR EXPRESSION OF HUMAN PLASMINOGEN VARIANT

This is a divisional of co-pending U.S. application Ser. No. 07/444,584 filed on Dec. 1, 1989, now U.S. Pat. No. 5,087,572.

BACKGROUND OF THE INVENTION

1. Field of the Invention

The present invention relates in general to methods and materials for expression of a gene encoding a plasminogen variant and in particular to methods and materials for expression of a human plasminogen variant in a mammalian cell system and products thereof.

2. Description of Related Art

Deleterious accumulations in blood vessels of the clot protein fibrin are prevented by proteolytic degradation (fibrinolysis) of fibrin or of its precursor fibrinogen by the enzyme plasmin (Pm). In a large variety of disorders, pathological fibrin deposits are not degraded spontaneously, resulting in thrombosis, the presence of a blood clot (thrombus) in a blood vessel In many cases, thrombolytic therapy, i.e., dissolution of the blood clot by Pm, is the only feasible treatment.

Pm is produced in the circulation by activation of a precursor, the "proenzyme" or "zymogen" called plasminogen (Pg). Thrombolytic therapy is conducted by the administration of a plasminogen activator. Among such plasminogen activators are streptokinase (SK), urokinase (UK) and tissue plasminogen activator (t-PA).

Human Pg (HPg) exists in the circulation as a single-chain glycoprotein containing 791 amino acids having an amino-terminal amino acid of Glu (circulating HPg may thus be referred to as [Glu$^1$]plasminogen) [Forsgren et al., *FEBS Lett.*, 213: 254-260 (1987); Malinowski et al., *Biochem.*, 23: 4243-4250 (1984); McLean et al., *Nature*, 330: 132-137 (1987); Sottrup-Jensen et al., *Prog. Chem. Fibrinolysis Thrombolysis*, 3: 191-209 (1978); Wiman, *Eur. J. Biochem.*, 39: 1-9 (1973); and Wiman, *Eur. J. Biochem.*, 76: 129-137 (1977)].

Analysis of the carbohydrate sequence of HPg reveals that there are two glycosylation variants, a first having two glycosylation sites (Asn$^{289}$ and Thr$^{346}$) and a second having one glycosylation site (Thr$^{346}$), with subforms exhibiting incomplete sialation [Castellino, *Chem. Rev.*, 81: 431-446 (1981)]. These forms and subforms are examples of post-translational modifications exhibited by circulating plasminogen.

HPg is activated by cleavage of a Arg$^{561}$-Val$^{562}$ peptide bond to produce the two-chain, disulfide-linked serine protease [Lys$^{78}$]Pm. This molecule also lacks the amino-terminal 77 amino acids as a result of autolysis by human Pm (HPm) formed during the activation [(Violand Castellino, *J. Biol. Chem.*, 251: 3906-3912 (1976)]. The cleavage may be catalyzed by a variety of activators, among which are SK, UK and t-PA. [For a review, see Castellino, *Bioscience*, 33: 647-650 (1983).] Whereas the latter two proteins are enzymes that directly catalyze cleavage of the appropriate peptide bond in HPg, providing HPm, SK has no such inherent activity and its plasminogen activator activity relies on its ability to form complexes with HPg and HPm and utilize the actual or latent plasmin active sites of these latter two molecules to function as an activator [Castellino, supra].

[Glu$^1$] Pg exists in plasma in the form of two major variants, which differ in their extent of glycosylation at Asn$^{289}$ [Hayes and Castellino, *J. Biol. Chem.*, 254: 8768-8780 (1979); Castellino, supra]. In [Glu$^1$ Pg, the latent plasmin heavy chain, which includes residues 1-561, contains five highly homologous regions called "kringles" [Sottrup-Jensen et al., supra, each containing approximately 80 amino acids. These kringles most likely exist as independent domains [Castellino et al., *J. Biol. Chem.*, 256 4778-4782 (1981)] and are of importance to the functional properties of HPg and HPm. As examples, the kringle 1 domain (amino acid residues 84-162) may be important in the interaction of plasmin or plasminogen with fibrin and fibrinogen [Lucas et al., *J. Biol. Chem.*, 258: 4249-4256 (1983)], with the negative activation effector (Cl$^-$) [Urano et al., *J. Biol. Chem.*, 262: 15959-15964 (1987)], and with the positive activation effector epsilon-aminocaproic acid (EACA) [Markus et al., *J. Biol. Chem.*, 253: 727-732 (1978)]. Additionally, this same segment is responsible for the initial rapid binding of HPm to its major plasma inhibitor, $\alpha_2$-antiplasmin [Moroi and Aoki, *J. Biol. Chem.*, 251: 5956-5965 (1976)]. The kringle 4 region (residues 358-435) appears to contain weak EACA binding site(s) present on [Glu$^1$]Pg, which may be involved in the very large ligand-induced conformational alteration of [Glu$^1$Pg [Violand et al., *Arch. Biochem. Biophys.*, 170: 300-305 (1975)] and in a concomitant increase in the activation rate of the zymogen in the presence of the positive effector EACA [Claeys and Vermyelin, *Biochem. Biophys. Acta*, 342, 351-359 (1974)].

Although thrombolytic therapy is useful, its therapeutic potential is constrained by the availability of plasminogen at the site of the thrombus. The concentration of plasminogen may be limited due to consumption of plasminogen as a result of thrombolytic therapy, due to an inadequate amount of plasminogen being present in thrombi, or to a local plasminogen depletion related to the age of the thrombus and ischemia (a localized anemia due to a reduction in blood flow). [Anderle et al., *Haemostasis*, 18: (Suppl. 1), 165-175 (1988)]. Thus, supplementation of the locally available amount of plasminogen is desirable.

Although expression of large amounts of plasminogen in a recombinant expression system is a convenient way to obtain plasminogen for use in thrombolytic therapy, there have been great difficulties in expression of intact HPg in mammalian expression systems due to the nearly ubiquitous presence of intracellular plasminogen activators among mammalian cell types. The presence of these activators results in the appearance of a degraded form of HPg in conditioned cell media of such expression systems, possibly form autodigestion of plasminogen by the HPm produced [Busby et al., *Fibrinolysis*, 2, 64 (1988)].

A recombinant human plasminogen has been produced in insect cells (irHPg) that, by amino-terminal amino acid sequence analysis, molecular weight estimation on SDS/PAGE, Sepharoselysine affinity chromatography behavior, activation characteristics, antibody reactivity, and activity of the resulting plasmin, appears to be comparable in properties to human plasma [Glu$^1$]Pg. [Whitefleet-Smith et al., *Arch. Biochem. Biophys.*, 271: 390-399 (1989)]. This is a significant finding, since to date there has not been successful expression of wild-type recombinant HPg (wt-rHPg) in mammalian cells. However, when the kinetic properties of equimolar complexes formed from streptokinase with plasma HPg and with irHPg were compared, SDS/PAGE gels of the temporal events within the respective complexes were identical to results published by Bajaj and Castellino, *J. Biol. Chem.*, 252: 492–498 (1977), in that a rapid conversion of HPg to HPm occurred. This suggests that HPg is not a stable component of the complex.

It is known that the cleavage site of human t-PA encompassing positions 270–280 can be modified to create a t-PA variant that is resistant or immune to specific enzymatic cleavage. For example, t-PA variants are described [EP Pat. Publ. No. 199,574] that have amino acid substitutions at the proteolytic cleavage sites at positions 275, 276, and 277. These variants, characterized preferentially as t-PA variants having an amino acid other than arginine at position 275, are referred to as protease-resistant one-chain t-PA variants; unlike natural t-PA, which can exist in either a one-chain or two-chain form, they are resistant to protease cleavage at position 275 and are therefore not converted metabolically in vivo into a two-chain form. This form of t-PA is thought to have certain advantages biologically and commercially, in that it is more stable and its fibrin binding and fibrin stimulation are increased relative to two-chain t-PA. Another form of plasminogen activator contains one domain capable of interacting with fibrin and the protease domain of urokinase, with one embodiment being urokinase altered to make it less susceptible to forming two-chain urokinase. See WO 88/05081 published Jul. 14, 1988.

For further patent literature regarding modification of the protease cleavage site of t-PA, see, for example, EPO Pat. Nos. 241,209; 201,153 published Nov. 12, 1986; 233,013 published Aug. 19, 1987; 292,009 published Nov. 23, 1988; 293,936 published Dec. 7, 1988; and 293,934 published Dec. 7, 1988; and WO 88/10119.

It is an object of the present invention to devise a plasminogen molecule that is stable as such in a complex with a fibrinolytic enzyme such as streptokinase and is hence more active than the natural molecule.

It is another object to produce the plasminogen molecule in any recombinant expression system, not just those that lack an endogenous, site-specific plasminogen activator (such as insect cells).

These and other objects will become apparent to one of ordinary skill in the art.

SUMMARY OF THE INVENTION

Accordingly, the present invention provides a nucleic acid sequence encoding a plasminogen resistant to proteolytic cleavage to its two-chain form, preferably human plasminogen, and most preferably [Glu$^1$]plasminogen.

In another aspect, the invention furnishes an expression vector comprising the nucleic acid sequence operably linked to control sequences, as well as host cells comprising the vector, preferably eukaryotic and most preferably mammalian host cells.

In a still further aspect, the invention provides a method for producing a plasminogen comprising the step of culturing the cells containing the above vector and preferably also the step of recovering the plasminogen from the cell culture, or culture medium if the molecule is secreted.

In yet another aspect, the invention provides a plasminogen resistant to proteolytic cleavage to its two-chain form. Preferably, the plasminogen is a single-chain sequence variant mutated at its 561–562 two-chain cleavage site.

The present invention also provides a pharmaceutical composition for affecting thrombolysis comprising an effective amount of the plasminogen described above formulated in a pharmaceutically acceptable carrier. The composition also preferably includes a fibrinolytic enzyme complexed to the plasminogen.

The present invention further supplies a method for thrombolytic therapy comprising the step of administering to a mammal in need of thrombolytic therapy an effective amount of the pharmaceutical composition above described.

In a still further aspect, the invention provides a method for preparing a binary complex between a fibrinolytic enzyme and plasminogen, the complex having a catalytic site essential for fibrinolytic activity blocked by a group removable by hydrolysis, comprising: mixing a fibrinolytic enzyme with the cleavage-resistant plasminogen herein to form a binary complex in the presence of an excess of a blocking agent of the formula A-B or E-F, wherein A is a hydrolytically labile blocking group that is selective for the catalytic site essential for fibrinolytic activity and is capable of transferring form the group B to the catalytic site, B is a group that facilitates the attachment of a to the enzyme, E is a locating group that locates the agent in the catalytic site, and F is a hydrolytically labile blocking group that is capable of transferring from the locating group to the catalytic site.

The plasminogen variants prepared in accordance with the process herein do not degrade to plasmin in a complex with streptokinase and rapidly ($\leq$30 sec.) develop both amidolytic and plasminogen activator activity.

BRIEF DESCRIPTION OF THE DRAWINGS

FIGS. 1A through 1P contain the nucleotide sequence for vector pUc119PN127.6, except that at nucleotide position 3809 the vector contains a T, whereas the sequence of FIG. 1, which reflects the sequence encoding native human plasminogen, contains a C. The FIG. 1 sequence also includes a deduced amino acid sequence for human plasminogen having the native sequence.

DETAILED DESCRIPTION OF THE PREFERRED EMBODIMENTS

A. Definitions

Figure 1A:
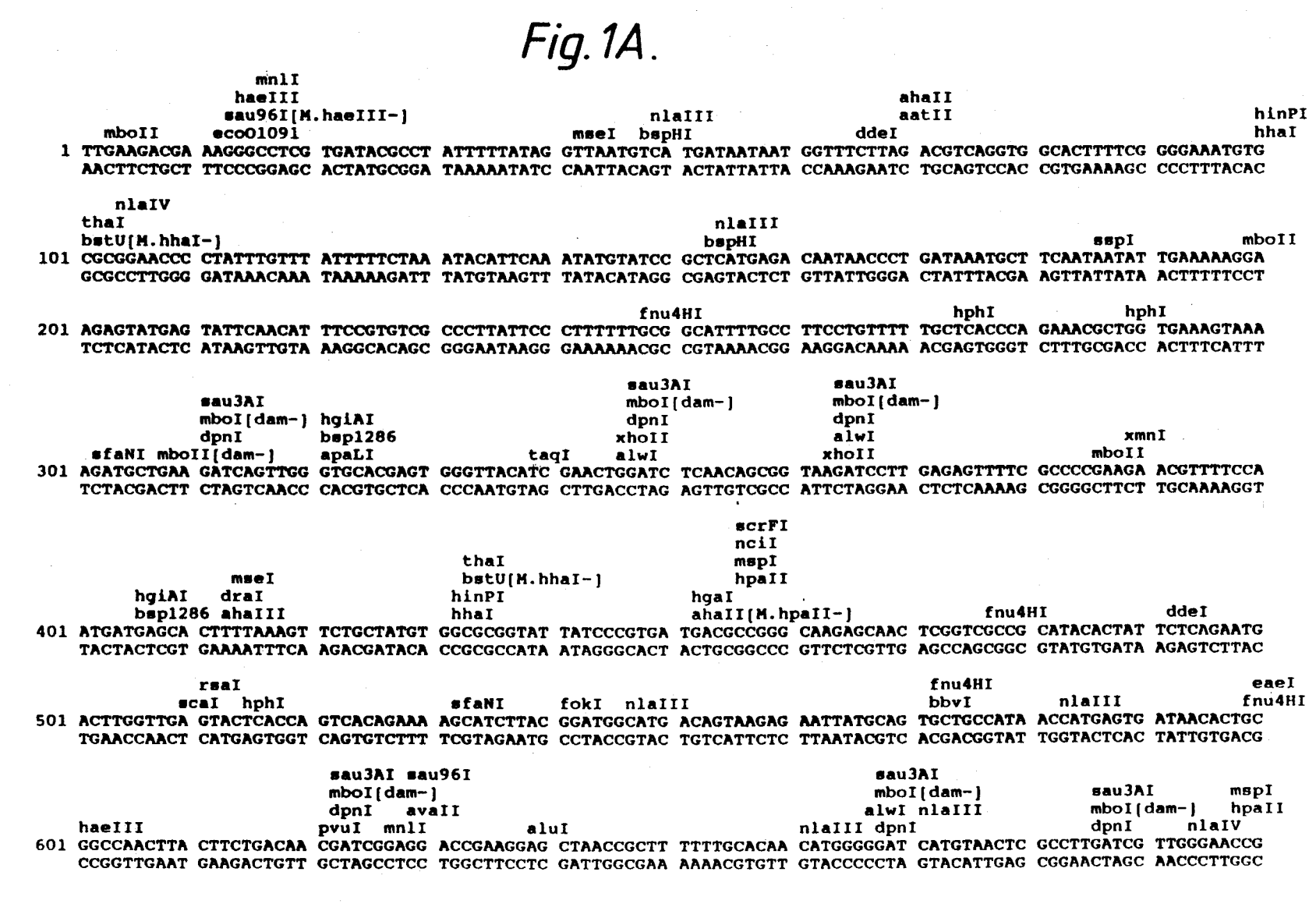
Figure 2:
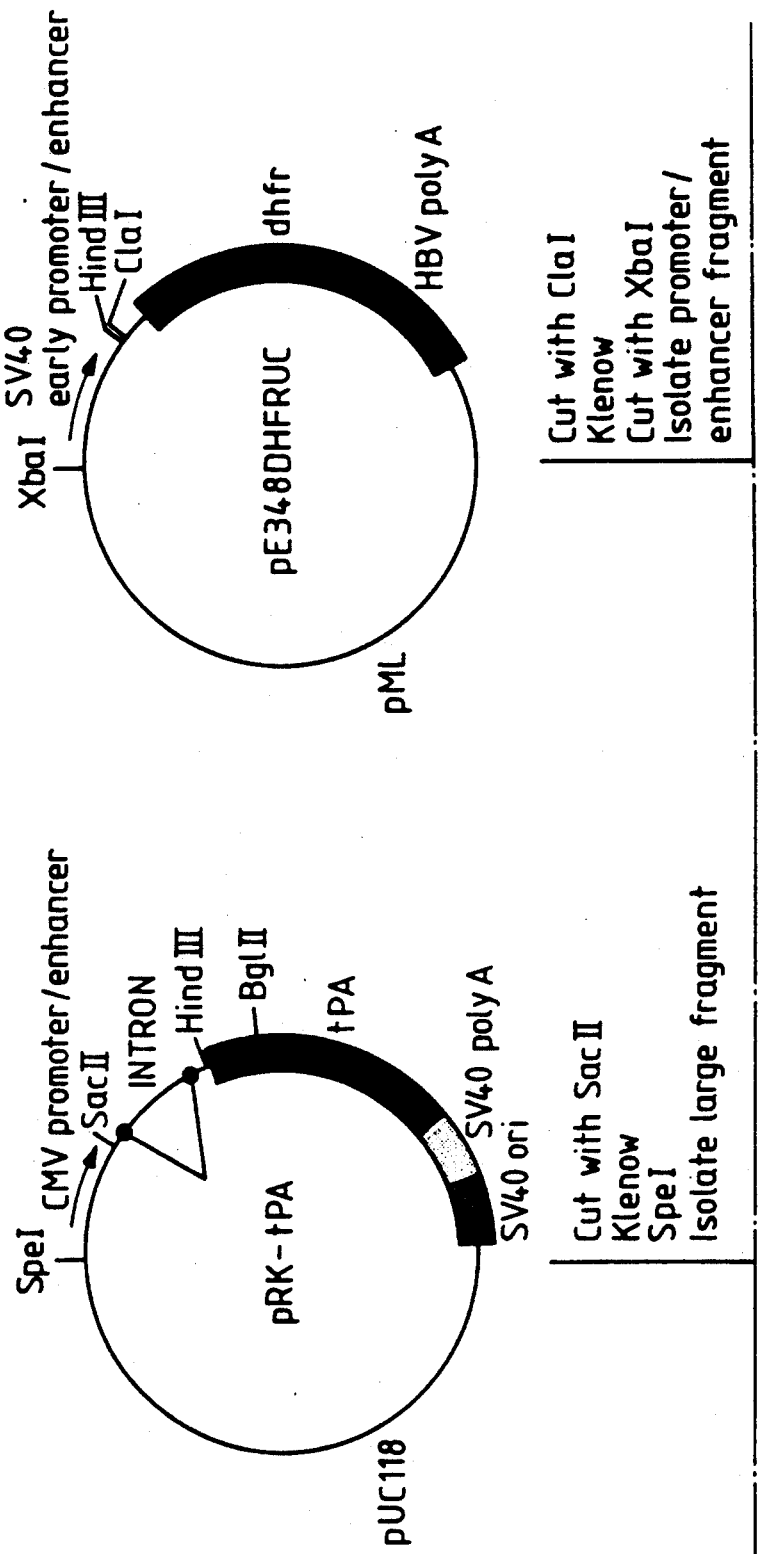
FIG. 2 shows the construction of the vector pSVI-tPA.
Figure 2:
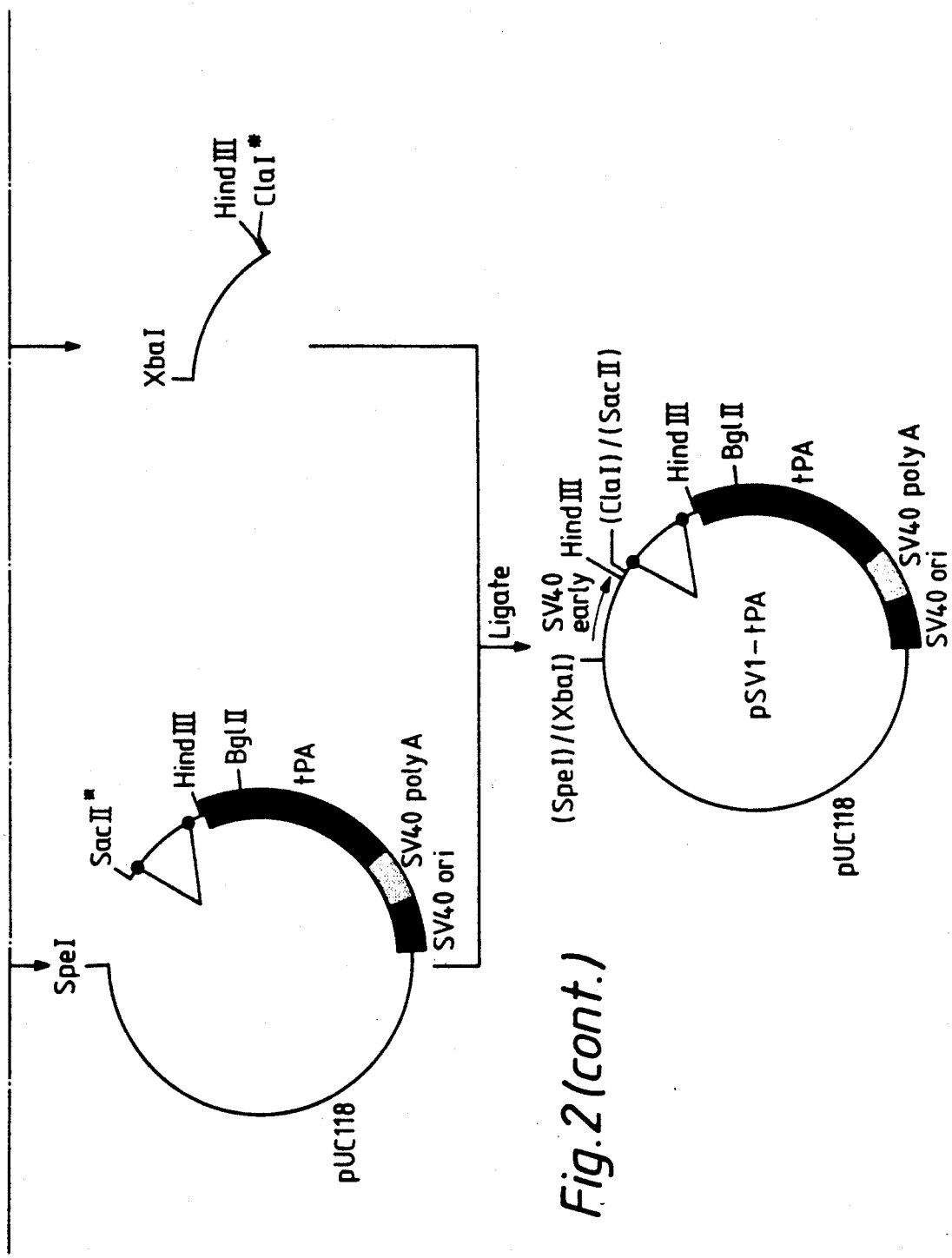

As used herein, "plasminogen," or "Pg," refers to plasminogen from any species, including bovine, equine, porcine, ovine, canine, murine, and feline plasminogen, as well as human plasminogen having the amino acid sequence shown in FIG. 1, provided that it has the biological activity of native Pg, i.e., is capable of being cleaved by a plasminogen activator (e.g., streptokinase, urokinase, or tissue plasminogen activator) to produce plasmin, or possesses an immune epitope that is immunologically cross-reactive with an antibody raised against at least one epitope of native Pg.

Plasminogen variants are defined as molecules in which the amino acid sequence of native Pg has been modified, typically by a predetermined mutation, wherein at least one modification renders the plasminogen resistant to proteolytic cleavage to its two-chain form. Amino acid sequence variants by Pg include, for example, deletions from, or insertions or substitutions of, residues within the amino acid Pg sequence shown in FIG. 1. Any combination of deletion, insertion and substitution may also be made to arrive at the final construct, provided that the final construct possesses the desired resistance to cleavage and biological activity. Obviously, it is preferred that the mutations made in the DNA encoding the variant Pg do not place the sequence out of reading frame and it is further preferred that they do not create complementary regions that could produce secondary mRNA structure (see, e.g., European Patent Publication No. 075,444).

A "two-chain cleavage site" in Pg and the site of "proteolytic cleavage to its two-chain form" comprises at least the arginine residue at position 561 of HPg. However, various amino acids adjacent to or within several residues of position 561 are also believed to be a part of the domain recognized by enzymes that convert plasminogen to its two-chain form. Thus, the replacement of amino acids at positions other than 561 within the domain could result in mutant plasminogens that are resistant to conversion to the two-chain form.

In the particular embodiment, "single-chain plasminogen variant" is a plasminogen that is resistant to conversion to the two-chain form at the 561–562 cleavage site. It is characterized by single or multiple amino acid substitutions at the two-chain activation site. As modified, such activation site is not enzymatically recognized, and therefore, not hydrolyzed by enzymes that normally convert plasminogen to its two-chain form.

By analogy to trypsin and chymotrypsin, it is believed that the importance of the formation of the two-chain form of any serine protease is the consequential presence of the free α-amino group in HPg at position 562. In this comparison, upon cleavage at arg561, the α-amino group 562 would be free to interact with the polypeptide chain in the area of the active site serine of plasminogen. The present invention therefore covers any mutation that would interfere with the interaction of such an α-amino group with the protease active site without diminishing overall activity of the molecule.

"Operably linked" as used herein refers to juxtaposition such that the normal function of the components can be performed. Thus, a coding sequence "operably linked" to control sequences refers to a configuration wherein the coding sequence may be expressed under the control of these sequences, and wherein the DNA sequences being linked are contiguous and, in the case of a secretory leader, contiguous and in reading phase. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned to facilitate translation of the coding sequence. Linking is accomplished by ligation at convenient restriction sites. If such sites do not exist, then synthetic oligonucleotide adaptors or linkers may be used in accordance with conventional practice.

As used herein, "cell," "cell line," and "cell culture" are used interchangeably and all such designations include progeny. Thus, the term "transformants" or "transformed cells" includes the primary subject cell and cultures derived therefrom without regard for the number of transfers. It is also understood that all progeny may not be precisely identical in DNA content due to deliberate or inadvertent mutations. Also included in these terms are mutant progeny that have the same function for which a primary subject cell is screened. Where distinct designations are intended, it will be clear from the context.

"Control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

The term "expression system" refers to DNA containing a desired coding sequence and control sequence in operable linkage, so that hosts transformed with these sequences are capable of producing the encoded proteins. For transformation, the expression system may be included on a vector called herein an "expression vector." However, the relevant DNA may also be integrated into the host chromosome.

B. Modes for Carrying Out the Invention

For purposes of this invention, variant plasminogen is that which is resistant to proteolytic cleavage to its two-chain form, generally by plasmin. Preferably the variant sequence is based on human plasminogen. While such variants may be prepared by any means, both recombinant and synthetic or partially synthetic, preferably the variants are those in which one of the amino acid residues, preferably the arginine at position 561, positioned at the critical cleavage site in the conversion of HPg to HPm, is replaced with another amino acid, preferably not a lysine residue, and most preferably a dicarboxyl containing amino acid or serine. Thus, the most preferred variants are R561S-HPg, R561E-HPg, and R561G-HPg, using the nomenclature indicated below. (The "A475" designation for HPg refers to the natural sequence HPg with an alanine residue at position 475, as opposed to the sequence found in pUC119PN127.6, which has a valine at position 475. The designations R561S-HPg, R561E-HPg, and R561G-HPg used below and in the claims refer, unless otherwise stated, to the HPg with an alanine at position 475.)

The variants may be prepared by site-directed mutagenesis of nucleotides in the DNA encoding the Pg, thereby producing DNA encoding the variant, and subsequent expression of the DNA in the appropriate host cell.

DNA encoding proteolytically resistant Pg may also be chemically synthesized and assembled by any of a number of techniques, prior to expression in a host cell. [See, e.g., Caruthers, U.S. Pat. No. 4,500,707; Balland et al., *Biochimie*, 67: 725-736 (1985); Edge et al., *Nature*, 292: 756-762 (1982).

In other embodiments, the variant may be unglycosylated, such as is accomplished by treating plasminogen expressed in a eukaryotic host with a suitable enzyme for such purpose such as glycopeptidase F. Also, the variant may contain other mutations, especially any that are beneficial to its activity.

For purposes of shorthand designation of the HPg variants described herein, it is noted that numbers refer to the amino acid residue/position along the amino acid sequences of putative mature Pg. Amino acid identification uses the single-letter alphabet of amino acids, i.e.,

| Asp | D | Aspartic acid | Ile | I | Isoleucine |
|-----|---|---------------|-----|---|------------|
| Thr | T | Threonine     | Leu | L | Leucine    |
| Ser | S | Serine        | Tyr | Y | Tyrosine   |
| Glu | E | Glutamic acid | Phe | F | Phenylala. |
| Pro | P | Proline       | His | H | Histidine  |
| Gly | G | Glycine       | Lys | K | Lysine     |
| Ala | A | Alanine       | Arg | R | Arginine   |
| Cys | C | Cysteine      | Trp | W | Tryptophan |
| Val | V | Valine        | Gln | Q | Glutamine  |
| Met | M | Methionine    | Asn | N | Asparagine |

The designation for a substitution variant herein consists of a letter followed by a number followed by a letter. The first (leftmost) letter designates the amino acid in the wild-type, mature Pg. The number refers to the amino acid position where the amino acid substitution is being made, and the second (right-hand) letter designates the amino acid that is used to replace the wild-type amino acid. The designation for an insertion variant consists of the letter i followed by a number designating the position of the residue in wild-type, mature Pg before which the insertion starts, followed by one or more capital letters indicating, inclusively, the insertion to be made. The designation for a deletion variant consists of the letter d followed by the number of the start position of the deletion to the number of the end position of the deletion, with the positions being based on the wild-type, mature Pg. Multiple mutations are separated by a comma in the notation for ease of reading them.

Examples of the nomenclature are as follows: a substitution variant where the arginine at position 561 of the wild-type Pg is replaced with a glutamic acid residue is designated R561E. A substitution variant with multiple substitutions at consecutive positions 561-562 of EE for RV is designated R561E, V562E. An insertion variant where cysteine and valine are inserted after position 560 of wild-type Pg is designated i560CV. A deletion variant where the amino acids at positions 561 to 562 are deleted from the wild-type, mature Pg is designated d562-562. The notation 'HPg' follows after each mutant.

Most deletions and insertions, and substitutions in particular, are not expected to produce radical changes in the characteristics of the recombinant Pg molecule. However, when it is difficult to predict the exact effect of the substitution, deletion, or insertion in advance of doing so, for example, when modifying the active site of Pg or an immune epitope, one skilled in the art appreciates that the effect may be evaluated by routine screening assays. For example, a variant typically may be made by site-specific mutagenesis of the native Pg-encoding nucleic acid, expression of the variant nucleic acid in recombinant cell culture, and, optionally, purification from the cell culture, for example, by immunoaffinity adsorption on a rabbit polyclonal anti-Pg column.

The variant may then be screened in a suitable screening assay for the desired characteristic. For example, a change in the immunological character of the Pg, such as affinity for a given antibody, may be measured by a competitive immunoassay. Changes in activation levels are measured by the appropriate assay. Modifications of such protein properties as redox or thermal stability, hydrophobicity, susceptibility to proteolytic degradation, or the tendency to aggregate with carriers or into multimers are assayed by methods well known to the ordinarily skilled artisan.

The vectors and methods disclosed herein are suitable for use in host cells over a wide range of prokaryotic and eukaryotic organisms, more preferably eukaryotes, and most preferably mammalian hosts.

In general, prokaryotes are preferred for initial cloning, amplifying, or storing the vectors of interest. Vector DNA is easily obtainable from certain prokaryotes. *E. coli* K12 strain MM 294 (ATCC No. 31,446) is particularly useful for this purpose. Other microbial strains that may be used include *E. coli* strains such as *E. coli* B and *E. coli* X1776 (ATCC No. 31,537). These examples are, of course, intended to be illustrative rather than limiting.

In general, plasmid vectors containing replicon and control sequences that are derived form species compatible with the host cell are used in connection with these prokaryotic hosts. The vector ordinarily carries a replication site, as well as marking sequences that are capable of providing phenotypic selection in transformed cells. For example, *E. coli* is typically transformed using pBR322, a plasmid derived from an *E. coli* species (see, e.g., Bolivar et al., *Gene,* 2: 95 [1977]). pBR322 contains genes for ampicillin and tetracycline resistance and thus provides easy means for identifying transformed cells. The pBR322 plasmid, or other microbial plasmid or phage, must also contain, or be modified to contain, promoters that can be used by the microbial organism for expression of the selectable marker genes.

These promoters most commonly used in recombinant DNA construction for prokaryotic hosts include the β-lactamase (penicillinase) and lactose promoter systems (Chang et al., *Nature,* 375: 615 [1978]; Itakura et al., *Science,* 198: 1056 [1977]; Goeddel et al., *Nature,* 281: 544 [1979]) and a tryptophan (trp) promoter system (Goeddel et al., *Nucleic Acids Res.,* 8: 4057 [1980]; EPO Appl. Publ. No. 0036,776). While these are the most commonly used, other microbial promoters have been discovered and utilized, and details concerning their nucleotide sequences have been published, enabling a skilled worker to ligate them functionally with plasmid vectors (see, e.g., Siebenlist et al., *Cell,* 20: 269 [1980]).

For expression, eukaryotic microbes, such as yeast cultures, are used. *Saccharoymyces cerevisiae,* or common baker's yeast, is the most commonly used among eukaryotic microorganisms, although a number of other strains are commonly available. For expression in Saccharomyces, the plasmid YRp7, for example (Stinchcomb et al., *Nature,* 282: 39 [1979]; Kingsman et al., *Gene,* 7: 141 [1979]; Tschemper et al., *Gene,* 10: 157 [1980]), is commonly used. This plasmid already contains the trp1 gene that provides a selection marker for a mutant strain of yeast lacking the ability to grow in tryptophan, for example, ATCC No. 44,076 or PEP4-1 (Jones, *Genetics,* 85: 12 [1977]). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., *J. Biol. Chem.*, 255: 2073 [1980]) or other glycolytic enzymes (Hess et al., *J. Adv. Enzyme Reg.*, 7: 149 [1968]; Holland et al., *Biochemistry*, 17: 4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters, which have the additional advantage of transcription controlled by growth conditions, are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication, and termination sequences is suitable.

In addition to microorganisms, cultures of cells derived from multicellular organisms may also be used as hosts. In principle, any such cell culture is workable, whether from vertebrate or invertebrate culture.

For expression in invertebrate hosts, numerous baculoviral strains and variants and corresponding permissive insect host cells form hosts such as *Aedes aegypti* (mosquito), *Aedes albopictus* (mosquito), *Drosphila melanogaster* (fruitfly), and *Bombyx mori* host cells, have been identified. (See, e.g., Luckow et al., *Bio/Technology*, 6: 47-55 (1988); and Maeda et al., *Nature*, 315: 592-594 (1985)). A variety of such viral strains are publicly available, e.g., the L-1 variant of *Autographa californica* NPV and the Bv-5 strain of *Bombyx mori* NPV, and such viruses may be used as the virus herein according to the present invention, particularly for transfection of *Spodoptera frugiperda* cells.

However, interest has been greatest in vertebrate cells, and propagation of vertebrate cells in culture (tissue culture) has become a routine procedure in recent years [*Tissue Culture*, Academic Press, Kruse and Patterson, editors (1973)].

Examples of such useful vertebrate host cell lines include the monkey kidney CVI line transformed by SV40 sequences (COS-7, ATCC CRL 1651); human embryonic kidney line (293, Graham et al., *J. Gen. Virol.*, 36: 59 (1977)); baby hamster kidney cells (BHK, ATCC CCL 10); Chinese hamster ovary cells (Urlaub and Chasin, *Proc. Natl. Acad. Sci. USA*, 77: 4216 (1980)); mouse sertoli cells (TM4, Mather, *Biol. Reprod.*, 23: 243-251 (1980)); monkey kidney cells (CVI, ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL51); rat hepatoma cells (HTC, M1.54, Baumann et al., *J. Cell. Biol.*, 85: 1-8 (1980)); and TRI cells (Mather et al., *Annals N.Y. Acad. Sci.*, 383: 44-68 (1982)). The most preferred eukaryotic host herein for stable expression is a Chinese hamster ovary cell line.

For use in mammalian cells, the control functions on the expression vectors are often provided by viral material. For example, commonly used promoters are derived from the genomes of polyoma, Adenovirus2, retroviruses, cytomegalovirus, and most frequently Simian Virus 40 (SV40). Other promoters are those from heterologous sources, e.g., the beta actin promoter. The early and late promoters of SV40 virus are particularly useful because both are obtained easily from the virus as a fragment that also contains the SV40 viral origin of replication [Fiers et al., *Nature*, 273: 113 (1978)]. Smaller or larger SV40 fragments may also be used, provided there is included the approximately 250-bp sequence extending from the HindIII site toward the BglI site located in the viral origin of replication. The immediate early promoter of the human cytomegalovirus is conveniently obtained as a HindIII restriction fragment. Greenaway et all, *Gene*, 18: 355-360 (1982). Further, it is also possible, and often desirable, to utilize promoter or control sequences normally associated with the desired gene sequence, provided such control sequences are compatible with the host cell systems.

Transcription of a DNA encoding the Pg by higher eukaryotes is increased by inserting an enhancer sequence into the vector. The enhancer is a cis-acting element of DNA, usually about from 10 to 300 bp, that acts on a promoter to enhance its transcription-initiation activity. Enhancers are relatively orientation and position independent, having been found 5' (Laimins et al., *Proc. Natl. Acad. Sci. USA*, 78: 993 (1981)) and 3' (Lusky et al., *Mol. Cell Bio.*, 3: 1108 (1983)) to the transcription unit, within an intron (Banerji et al., *Cell*, 33: 729 (1983)) as well as within the coding sequence itself (Osborne et al., *Mol. Cell Bio.*, 4: 1293 (1984)). Preferably, however, the enhancer element is located upstream of the promoter sequence for this invention. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. Most preferred herein is the SV40 enhancer region.

Expression vectors used in mammalian host cells will also contain polyadenylation sites. Examples of polyadenylation regions are those derived from viruses such as, e.g., the SV40 (early and late) or HBV.

An origin of replication may be provided either by construction of the vector to include an exogenous origin, such as may be derived from SV40 or other viral (e.g., Polyoma, Adeno, VSV, BPV) source, or ay be provided by the host cell. If the vector is integrated into the host cell chromosome, the latter is often sufficient.

The expression vectors may suitably contain a selection gene, also termed a selectable marker. A selection gene encodes a protein necessary for the survival or growth of a host cell transformed with the vector. Examples of suitable selectable markers for mammalian cells include dihydrofolate reductase (DHFR), thymidine kinase (TK), or neomycin. When such selectable markers are successfully transferred into a mammalian hose cell, the transformed mammalian host cell can survive if placed under selective pressure.

There are two widely used distinct categories of selective regimes. The first category is based on the metabolism of a cell and the use of a mutant cell line that lacks the ability to grow independent of a supplemented medium. Two examples are CHO DHFR cells and mouse LTK cells. These cells lack the ability to grow without the addition of such nutrients as thymidine or hypoxanthine. Because these cells lack certain genes necessary for a complete nucleotide synthesis pathway, they cannot survive unless the missing nucleotides are preferred in a supplemented medium. An alternative to supplementing the medium is to introduce an intact DHFR or TK gene into cells lacking the respective genes, thus altering their growth requirements. Individual cells that were not transformed with the DHFR or TK gene will not be capable of survival in non-supplemented medium. Therefore, direct selection of those cells requires cell growth in the absence of supplemental nutrients.

The second category is dominant selection, which refers to a selection scheme that does not require the use of a mutant cell line. This method typically employs a drug to arrest growth of a host cell. Those cells that have a novel gene would express a protein conveying drug resistance and would survive the selection. Examples of drugs used in dominant selection include neomycin (Southern and Berg, *J. Mol. Appl. Genet.*, 1: 327 (1982)), mycophenolic acid (Mulligan and Berg, *Science*, 209: 1422 (1980)), or hygromycin (Sugden et al., *Mol. Cell. Biol.*, 5: 410–413 (1985)). The three examples given above employ bacterial genes under eukaryotic control to convey resistance to the appropriate drug, i.e., neomycin (G418 or geneticin), xgpt (mycophenolic acid), or hygromycin, respectively.

Extremely good amounts of polypeptide are produced by cell cultures using the method of this invention; however, refinements, using a secondary coding sequence, serve to enhance production levels even further. One secondary coding sequence comprises dihydrofolate reductase (DHFR) that is affected by an externally controlled parameter, such as methotrexate (MTX), thus permitting control of expression by control of the methotrexate concentration.

In selecting a preferred host cell line for transfection by the vectors of the invention that comprise DNA sequences encoding both the gene of interest and DHFR protein, it is appropriate to select the host according to the type of DHFR protein employed. If wild-type DHFR protein is employed, it is preferable to select a host cell that is deficient in DHFR, thus permitting the use of the DHFR coding sequence as a marker for successful transfection in selective medium that lacks hypoxanthine, glycine, and thymidine. An appropriate host cell in this case is the Chinese hamster ovary (CHO) cell line deficient in DHFR activity, prepared and propagated as described by Urlaub and Chasin, *Proc. Natl. Acad. Sci.* (USA) 77: 4216 (1980).

On the other hand, if DHFR protein with low binding affinity for MTX is used as the controlling sequence, it is not necessary to use DHFR-deficient cells. Because the mutant DHFR is resistant to methotrexate, MTX-containing media can be used as a means of selection provided that the host cells are themselves methotrexate sensitive. Most eukaryotic cells that are capable of absorbing MTX appear to be methotrexate sensitive. One such useful cell line is a CHO line, CHO-K1 (ATCC No. CCL 61).

Construction of suitable vectors containing the desired coding and control sequences employs standard ligation techniques. Isolated plasmids or DNA fragments are cleaved, tailored, and religated in the form desired to prepare the plasmid required.

If blunt ends are required, the preparation may be treated for 15 minutes at 15° C. with 10 units of Polymerase I (Klenow), phenol-chloroform extracted, and ethanol precipitated.

Size separation of the cleaved fragments may be performed using 6 percent polyacrylamide gel described by Goeddel et al., *Nucleic Acids Res.*, 8: 4057 (1980).

For analysis to confirm correct sequences in plasmids constructed, the ligation mixtures are typically used to transform *E. coli* K12 strain 294 (ATCC 31,446) or other suitable *E. coli* strains, and successful transformants selected by ampicillin or tetracycline resistance where appropriate. Plasmids from the transformants are prepared and analyzed by restriction mapping and/or DNA sequencing by the method of Messing et al., *Nucleic Acids Res.*, 9: 309 (1981) or by the method of Maxam et al., *Methods of Enzymology*, 65: 499 (1980).

After introduction of the DNA into the mammalian cell host and selection in medium for stable transfectants, amplification of DHFR-protein-coding sequences is effected by growing host cell cultures in the presence of approximately 200–500 nM concentrations of methotrexate, a competitive inhibitor of DHFR activity. The effective range of concentration is highly dependent, of course, upon the nature of the DHFR gene and the characteristics of the host. Clearly, generally defined upper and lower limits cannot be ascertained. Suitable concentrations of other folic acid analogs or other compounds that inhibit DHFR could also be used. MTX itself is, however, convenient, readily available, and effective.

Complexes formed between fibrinolytic enzymes and plasminogen may be used as thrombolytic agents, as described further in Smith et al., U.S Pat. No. 4,808,405, the disclosure of which is incorporated herein by reference and which is illustrated in Example 5 below. Briefly, an enzyme derivative may be prepared that comprises a binary complex between streptokinase and plasminogen, which complex has a catalytic site essential for fibrinolytic activity blocked by a group that is removable by hydrolysis such that the pseudo-first order rate constant for hydrolysis of the derivative is in the range of $10^{-5} \text{sec}^{-1}$ to $10^{-3} \text{sec}^{-1}$ in isotonic aqueous media at pH 7.4 at 37° C., provided that the group that blocks the catalytic site is not a p-guanidino-benzoyl group. Examples of suitable such groups include acyl groups such as benzoyl, substituted benzoyl, acryloyl, or substituted acryloyl groups.

A method for preparing the complexes includes mixing streptokinase with plasminogen in the presence of an excess of a blocking agent of the formula A-B or E-F, wherein A is a group that is selective for the catalytic site essential for fibinolytic activity and that is capable of transferring from the group B to the catalytic site, and B is a group that facilitates the attachment of A to the enzyme; E is a locating group that locates the agent in the catalytic site and F is a group capable of transferring from the locating group to the catalytic site, and thereafter optionally isolating the derivatives so formed. Preferably the group removable by hydrolysis is an acyl group, most preferably a benzoyl, substituted benzoyl, acryloyl, or substituted acryloyl group, e.g., benzoyl substituted with halogen, $C_{1-6}$ alkyl, $C_{1-6}$ alkoxy, $C_{1-6}$ alkanoyloxy, or $C_{1-6}$ alkanoylamino or acryloyl substituted with $C_{1-6}$ alkyl, furyl, phenyl, or $C_{1-6}$ alkyl phenyl. Also, preferably AB is p-nitrophenyl-p'-guanidinobenzoate, group E is p-amidinophenyl or p-acetamidophenyl, and group F is a benzoyl or acryloyl group.

Also contemplated as part of this invention is a pharmaceutical composition that includes human plasminogen variant. Preferably such composition comprises a pharmaceutically acceptable carrier such as isotonic aqueous buffer or pharmaceutical grade "Water for Injection." In addition, the invention encompasses a pharmaceutical formulation comprising a pharmaceutically acceptable carrier together with a fibrinolytic enzyme, preferably a complex of the enzyme with the plasminogen variant, more preferably a binary complex of streptokinase and plasminogen variant, and most preferably a p-anisoyl streptokinase/plasminogen complex without internal peptide bond cleavage, as in Smith et al., U.S. Pat. 4,808,405, supra. In a further embodiment, the active site of the complex responsible for fibrinolytic activity is blocked by a group that is removable by hydrolysis such that the pseudo-first order rate constant for hydrolysis of the complex is in the range of $10^{-}$ sec$^{-1}$ to $10^{-3}$ sec$^{-1}$ in isotonic aqueous media at pH 7.4 at 37° C.

The compositions according to this invention are formulated in accordance with standard procedures to be adapted for parenteral administration to humans.

Typically, the compositions for intravenous administration are solutions of the sterile derivative in sterile isotonic aqueous buffer. Where necessary, the composition also includes a solubilizing agent for the complex. In general, the complex is supplied in unit dosage form, for example, as a dry powder or water-free concentrate in a sealed container such as an ampoule. For administration by infusion, the complex is dispensed from an infusion bottle containing sterile pharmaceutical grade Water for Injection. For administration by injection, the complex is dispensed from a vial of sterile Water for Injection. The injectable or infusible composition will be made up by mixing the ingredients prior to administration.

The effective amount of complex administered will depend on many factors, including the amount of fibrinolysis required and the speed with which it is required, the extent of thromboembolism, and the position and size of the clot, but the amount is generally dictated by the result to be obtained, i.e., lysis of the clot. For example, a patient with a pulmonary embolism or a life-threatening thrombus will require administration of a bolus of rapidly acting material. On the other hand, where it is desired to prevent the formation of thrombi after an operation, a small quantity of slow-acting material is particularly useful. The precise dose to be employed and the mode of administration may be decided according to the circumstances as seen by the physician. However, in general, a patient being treated for a medium-size thrombus receives a dose of from 0.10 to 1.0 mg/kg of body weight daily either by injection (in up to eight doses) or by infusion.

In order to simplify the examples and claims, certain frequently occurring methods will be referenced by shorthand phrases.

"Transfection" refers to the taking up of an expression vector by a host cell whether or not any coding sequences are in fact expressed. Numerous methods of transfection are known to the ordinarily skilled artisan, for example, CaPO$_4$ and electroporation. Successful transfection is generally recognized when any indication of the operation of this vector occurs within the host cell.

"Transformation" means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described by Cohen, S. N. *Proc. Natl. Acad. Sci.* (USA), 69: 2110 (1972); Mandel et al., *J. Mol. Biol.* 53: 154 (1970); and more recently Liljestrom et al., *Gene*, 40: 241-246 (1985), is generally used for prokaryotes or other cells that contain substantial cell-wall barriers. For mammalian cells without such cell walls, the calcium phosphate precipitation method [Graham, F. and van der Eb, A., *Virology*, 52: 456-457 (1978); Kingston, in *Current Protocols in Molecular Biology*, Ausubel, et al., eds., (John Wiley & Sons, New York: 1987), 1.8.1-1.8.3] is preferred. General aspects of mammalian cell host system transformations have been described by Axel in U.S. Pat. No. 4,399,216 issued Aug. 16, 1983. Transformations into yeast are typically carried out according to the method of Van Soligen, P., et al., *J. Bact.*, 130: 946 (1977) and Hsiao, C. L., et al., *Proc. Natl. Acad. Sci.* (USA) 76: 3829 (1979). However, other methods for introducing DNA into cells such as by nuclear injection or by protoplast fusion may also be used.

"Plasmids" are designated by a lower case p preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

The technique of "PCR" as used herein generally refers to the following: Minute amounts of a specific piece of DNA can be amplified using the polymerase chain reaction (PCR) as described in U.S. Pat. No. 4,683,195 issued Jul. 28, 1987. Generally, sequence information from the ends of the stretch of interest or beyond needs to be available, such that oligonucleotide primers can be designed; these primers will point towards one another, and will be identical or similar in sequence to opposite strands of the template to be amplified. The 5' terminal nucleotides of the two primers will coincide with the ends of the amplified material. PCR can be used to amplify specific DNA sequences from total genomic DNA, cDNA transcribed from total cellular RNA, bacteriophage or plasmid sequences, etc. See generally H. Erlich, ed., *PCR Technology*, Stockton Press, N.Y., 1989.

The technique of "PCR mutagenesis" as used herein refers to the following (see Erlich, supra, the chapter by R. Higuchi, p. 61-70): When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

In the procedure detailed below, the ratio of template to product material is extremely low, and as a result, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer, or performing a second PCR with different mutant primers and ligating the two resulting PCR fragments simultaneously to the vector fragment in a three (or more)-part ligation.

The PCR mutagenesis procedure employed in the examples below was as follows: Template plasmid DNA (1 µg) was linearized by digestion with a restriction endonuclease that has a unique recognition site in the plasmid DNA outside of the region to be amplified. Of this material, 1-5 ng was added to a PCR mixture containing 16.6 mM $(NH_4)_2SO_4$, 67 mM tris.HCl (pH 8.8), 6.7 mM $MgCl_2$, 6.7 µM EDTA, 10 mM 2-mercaptoethanol, 1 mM each dATP, dCTP, dGTP, and TTP, 170 µg/ml bovine serum albumin, 25 pmole of each oligonucleotide primer, and 1 µl Thermus aquaticus (Taq) DNA polymerase (5 units/µl, purchased from Perkin-Elmer Cetus, Norwalk, Conn. and Emeryville, Calif.) in a final volume of 50 µl in a 0.5-ml reaction vial. The reaction mixture was overlayed with 35 µl mineral oil and inserted into a DNA Thermal Cycler (purchased from Perkin-Elmer Cetus) programmed as follows:

| | |
|---|---|
| time-delay file | 12 min. 94° C. |
| thermo-cycle file | 1 min. 50° C. |
| | 2-3 min. 68-72° C. |
| | 1 min. 94° C. |
| | 20 cycles |
| time-delay file | 4 min. 50° C. |
| time-delay file | 12 min. 68° C. |
| soak file | 4° C. |

Each file shown above was linked to the one on the next line. At the end of the program, the reaction vial was removed from the thermal cycler and the aqueous phase transferred to a new vial, extracted with phenol/-chloroform/isoamylalcohol (50:50:1 vol), and ethanol precipitated, and the DNA was recovered by standard procedures. This material was subsequently subjected to the appropriate treatments for insertion into a vector.

"Digestion" of DNA refers to catalytic cleavage of the DNA with an enzyme that acts only at specific nucleotide sequences in the DNA. Such enzymes are called restriction enzymes, and the sequence for which each is specific is called a restriction site. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 µg of plasmid or DNA fragment is used with about 1-2 units of enzyme in about 20 µl of buffer solution. Appropriate buffers and substrate amounts for particular restriction enzymes are specified by the manufacturer. Incubation of about 1 hour at 37° C. is ordinarily used, but may vary in accordance with the supplier's instructions. After incubation, protein is removed by extraction with phenol and chloroform, and the digested nucleic acid is recovered from the aqueous fraction by precipitation with ethanol. When appropriate, digestion with a restriction enzyme is followed by bacterial alkaline phosphatase-mediated hydrolysis of the terminal 5' phosphates to prevent the two ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (T. Maniatis et al., 1982, *Molecular Cloning: A Laboratory Manual* (New York: Cold Spring Harbor Laboratory, 1982) pp. 133-134).

"Recovery" or "isolation" of a given fragment of DNA from a restriction digest means separation of the digest on polyacrylamide or agarose gel by lectrophoresis, identification of the fragment of interest by comparison of its mobility versus that of marker DNA fragments of known molecular weight, removal of the gel section containing the desired fragment, and separation of the gel from DNA. This procedure is known generally. For example, see R. Lawn et al., *Nucleic Acids Res.* 9:6103-6114 (1981), and D. Goeddel et al., *Nucleic Acids Res.* 8:4057 (1980).

"Ligation" refers to the process of forming phosphodiester bonds between two double stranded nucleic acid fragments (T. Maniatis et al., 1982, supra, p. 146). Unless otherwise provided, ligation may be accomplished using known buffers and conditions with 10 units of T4 DNA ligase ("ligase") per 0.5 µg of approximately equimolar amounts of the DNA fragments to be ligated. "Preparation" of DNA from transformants means isolating plasmid DNA from microbial culture. Unless otherwise provided, the alkaline/SDS method of Maniatis et al., 1982, supra, p. 90, may be used.

"Oligonucleotides" are short-length, single- or double-stranded polydeoxynucleotides that are chemically synthesized by known methods (such as phosphotriester, phosphite, or phosphoramidite chemistry, using solid phase techniques such as described in EP Pat. Pub. No. 266,032 published May 4, 1988, or via deoxynucleoside H-phosphonate intermediates as described by Froehler et al., *Nucl. Acids Res.*, 14: 5399-5407 [1986]). They are then purified on polyacrylamide gels.

"Site-directed mutagenesis" is a technique standard in the art, and is conducted using a synthetic oligonucleotide prier complementary to a single-stranded phage DNA to be mutagenized except for limited mismatching that represents the desired mutation. Briefly, the synthetic oligonucleotide is used as a primer to direct synthesis of a strand complementary to the phage, and the resulting double-stranded DNA is transformed into a phage-supporting host bacterium. Cultures of transformed bacteria are plated in top agar, permitting plaque formation from single cells that harbor the phage. Theoretically, 50% of new plaques contain the phage having, as a single strand, the mutated form; 50% will have the original sequence. The plaques are hybridized with kinased synthetic primer at a temperature that permits hybridization of an exact match, but at which temperature the mismatches with the original strand are sufficient to prevent hybridization. Plaques that hybridize with the probe are then selected and cultured, and the DNA is recovered.

The following examples are intended to illustrate the best mode now known for practicing the invention, but the invention is not to be considered limited thereto.

All literature citations herein are expressly incorporated by reference.

EXAMPLE 1

Construction of t-PA Intermediate Expression Vectors

Various t-PA vectors were derived from parent vector pSVI-tPA by altering a number of features of the splice donor-intron-splice acceptor unit with the specific purpose of increasing the efficiency of proper removal of the intron.

a. pSVI-t-PA

Portions of two previously disclosed mammalian expression vectors, pRK-tPA and pE348DHFRUC, were combined to generate pSVI-t-PA.

Mammalian expression vector pRK-tPA was prepared from pRK5 (described in EP 307,247, supra, where the pCIS2.8c28D starting plasmid is described in EP 278,776 published Aug. 17, 1988 based on U.S. Ser. Nos. 07/071,674 and 06/907,297) and from t-PA cDNA (Pennica et al., Nature, 301: 214 (1983)). The cDNA was prepared for insertion into pRK5 by cutting with restriction endonuclease HindIII (which cuts 49 pairs 5' of the ATG start codon) and restriction endonuclease BalI (which cuts 276 base pairs downstream of the TGA stop codon). This cDNA was ligated into pRK5 previously cut with HindIII and SmaI using standard ligation methodology (Maniatis et al., *Molecular Cloning: A Laboratory Manual*, Cold Spring Harbor Laboratory, New York, 1982). This construct was named pRK-t-PA, and is shown in FIG. 2.

pRK-tPA drives the efficient synthesis of t-PA upon transient transfection into human 293 fibroblasts. The vector contains the cytomegalovirus immediate early gene enhancer and promoter, the CMV-IE splice donor site and a portion of the associated intron, the bacteriophage SP6 promoter, a portion of an $IgV_H$ intron and the associated splice acceptor, the cDNA encoding t-PA, the SV40 early polyadenylation ("polyA") region, and the SV40 origin of replication ("ori") in plasmid pUC118.

The vector pE348DHFRUC (Vannice and Levinson, *J. Virology*, 62: 1305-1313 (1988), where it is designated pE, FIG. 1) contains the SV40 enhancer and early promoter region upstream of the HindIII site (position 5171 in the virus), preceding cDNA encoding murine dihydrofolate reductase (DHFR), which is followed by the 584-bp Hepatitis B virus (HBV) polyA signal in plasmid pML1 from the BamHI to the BglII sites of HBV. This plasmid contains a polylinker immediately upstream of the SV40 sequences.

Portions of vector pRK-tPA and pE348DHFRUC were isolated as follows (FIG. 2):

1. Vector pRK-tPA was digested with restriction enzyme SacII, and subsequently treated with the large ("Klenow") fragment of *e. coli* DNA polymerase I ("pol I") to remove the 3' protruding ends generated by SacII cleavage. This was followed by digestion with the restriction enzyme SpeI. The larger fragment containing a portion of the CMV transcribed sequences, the splice donor-intron-splice acceptor unit ("Intron" in FIG. 2), the t-PA cDNA, the SV40 polyA and ori regions, and pUC118, including a few nucleotides from the 5' end of CMV, was isolated from a polyacrylamide gel after electrophoretic separation of the fragments ("gel isolated").

2. Vector pE348DHFRUC was digested with the enzyme ClaI and the resulting 5' protruding ends were filled in using Klenow polI in the presence of all four deoxyribonucleotides (dNTPs: dATP, dGTP, dCTP, TTP). Upon subsequent digestion with XbaI, the SV40 transcription regulatory sequences (enhancer and early promoter, including the SV40 early sites of transcription initiation), present on the smaller XbaI-ClaI fragment (360 nucleotides), were gel isolated.

The isolated pRK-tPA and pE348DHFRUC fragments were ligated to generate vector pSVI-tPA.

b. pSVI2-tPA

Figure 3:
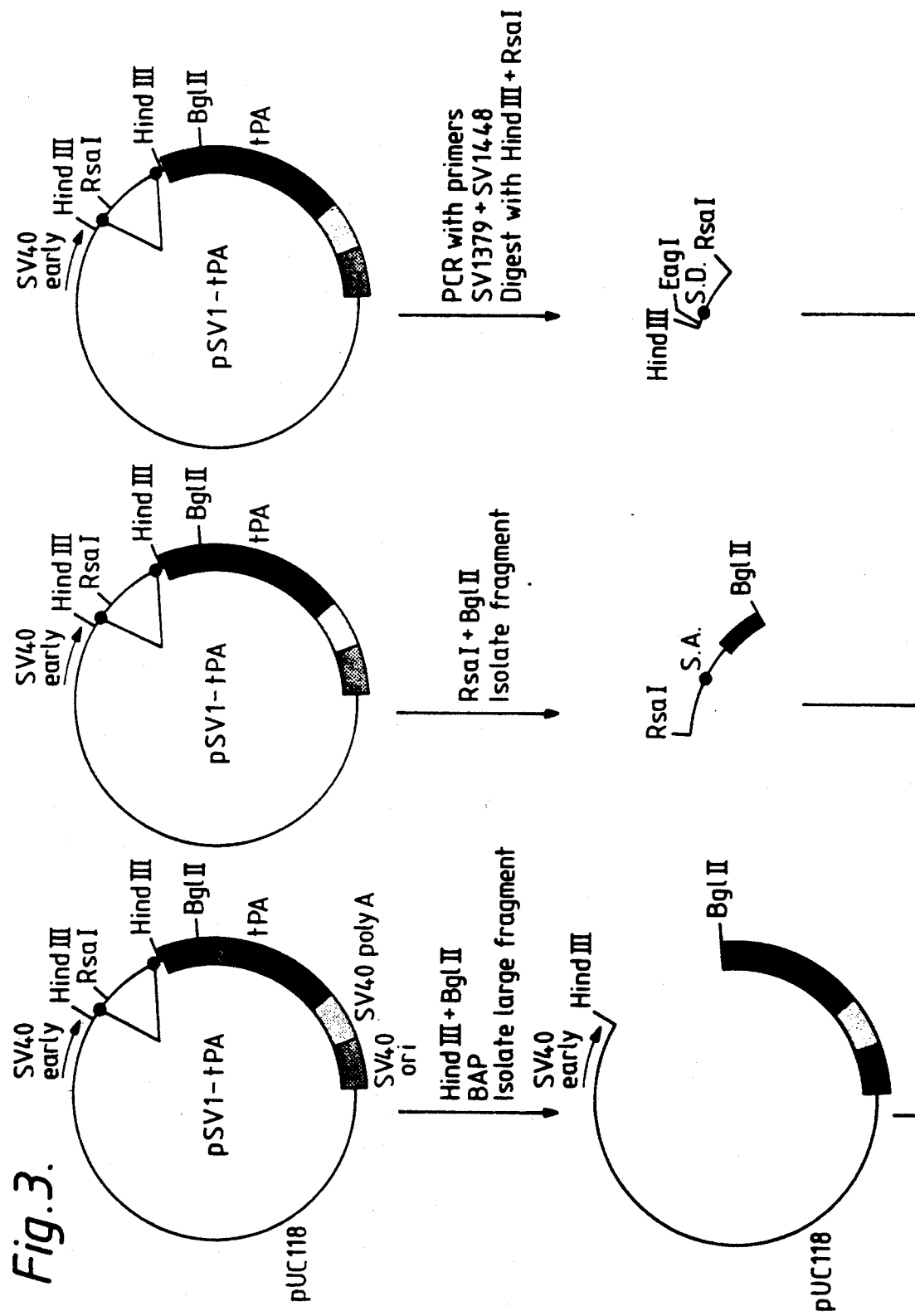
FIG. 3 shows the construction of the vector pSVI2-tPA.
Figure 3:
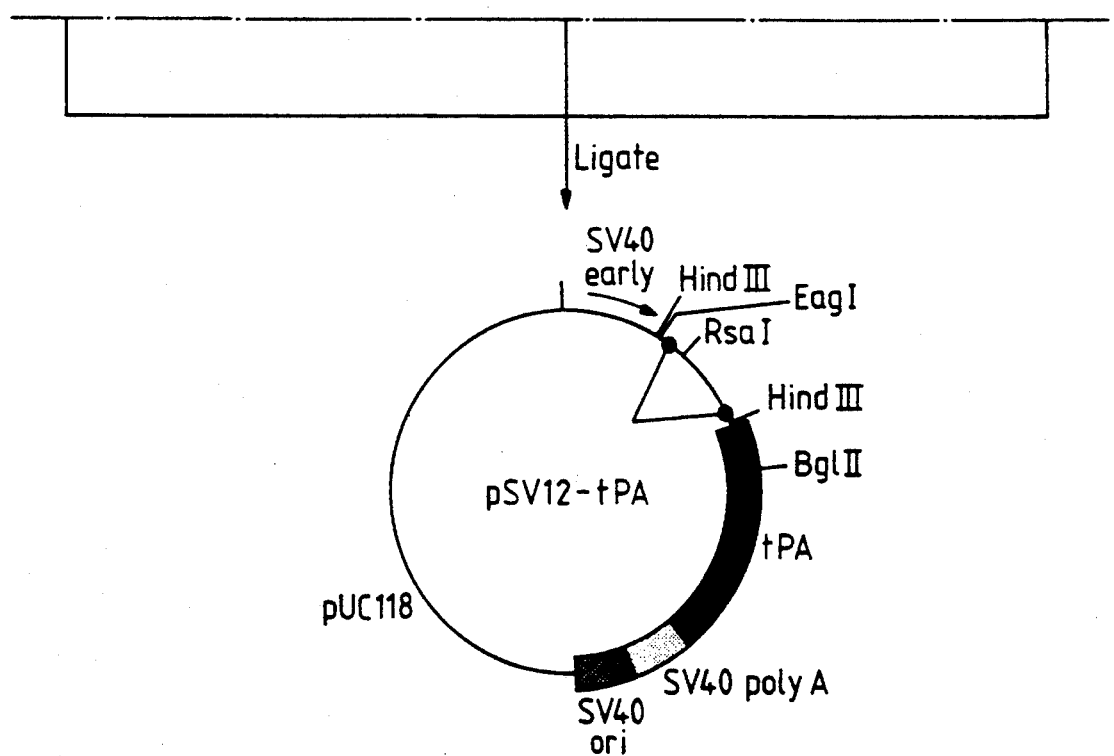

The vector pSVI2-tPA was prepared as shown in FIG. 3, wherein the splice donor site of vector pSVI-tPA was mutated by ligation of three fragments, prepared as described below. Nucleotides −3 (G) and −1 (C) relative to the 5' exon/intron boundary of pSVI-tPA were changed to C and G, respectively, to render the splice donor sequence identical to the consensus sequence CAG/GUAAGU. This was accomplished as follows:

1. Vector pSVI-tPA was cleaved with HindIII and BglII to generate a small fragment containing primarily the splice donor-intron-splice acceptor unit between the two HindIII sites at positions 381 and 618, another small fragment containing a 5' portion of the t-PA cDNA located between the HindIII and BglII sites at positions 618 and 770, and a large fragment containing the remainder of the pSVI-tPA DNA. After bacterial alkaline phosphatase ("BAP") treatment, the three fragments were separated by gel electrophoresis and the largest was recovered.

2. Vector pSVI-tPA was separately digested with RsaI and BglII, and the 327-nucleotide fragment extending from the RsaI site at position 443 to the BglII site at position 770 was gel isolated. This fragment includes the 3' portion of the intron, the splice acceptor, and a 5' portion of the t-PA cDNA.

3. Two oligonucleotides ("primers" in FIGS. 3-7) were synthesized. The first (SVI379) corresponded to nucleotides 379 to 400 (upper strand) of pSVI-tPA, with the exception of a G to C change at position 390 introduced to generate the sequence recognized by restriction endonuclease EagI (CGGCCG), and overlapped a HindIII site. It had the following sequence (position of the change underlined):

5'-AAAAGCTTATCCGGCCGGGAAC-3'.

The second oligonucleotide (SVI448) was identical in sequence to the lower strand of pSVI-tPA between positions 448 and 427, except for a G to C change at the 11th nucleotide and a C to G change at nucleotide-13. It included a RsaI site just 5' to the two single nucleotide changes. The sequence of this oligonucleotide, with the differences from the corresponding pSVI-tPA sequenced underlined, was as follows:

5'-CGGTACTTACCTGACTCTTGGC-3'.

The two oligonucleotides were used to amplify by PCR the region of pSVI-tPA between positions 379 and 448, which includes the splice donor. The PCR products were digested with HINDIII and RsaI, and the 62-nucleotide fragment was gel isolated.

The three isolated fragments were ligated and introduced into E. coli MM294. Plasmid DNA was isolated from several ampicillin-resistant colonies, and the nucleotide sequence of one isolate (pSVI2-tPA), that had the three fragments ligated in the desired order, was determined to verify the presence of the nucleotide changes specified by the two primers and the integrity of the region derived from the amplified fragment.

c. pSVI3-tPA

Figure 4:
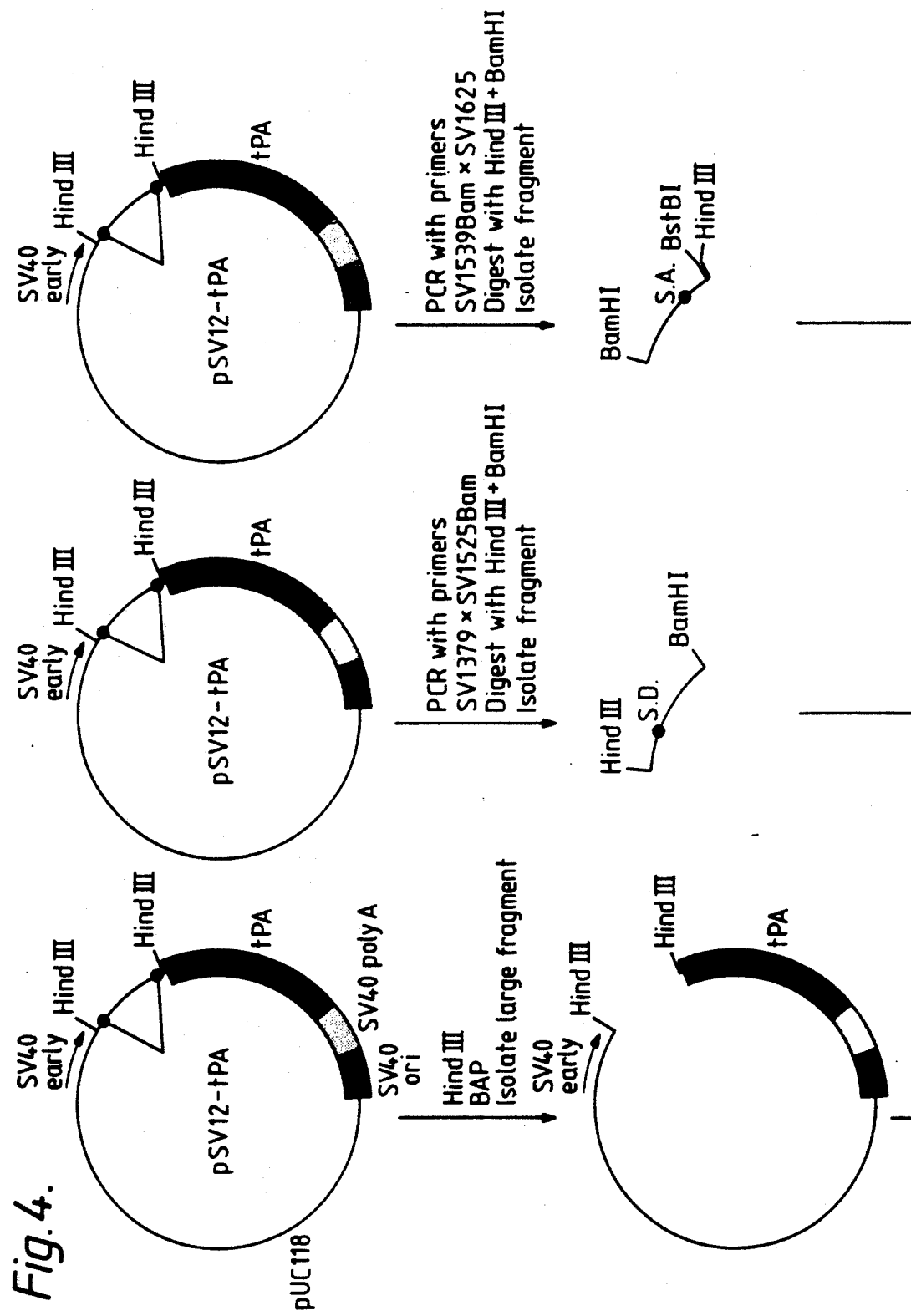
FIG. 4 shows the construction of the vector pSVI3-tPA.
Figure 4:
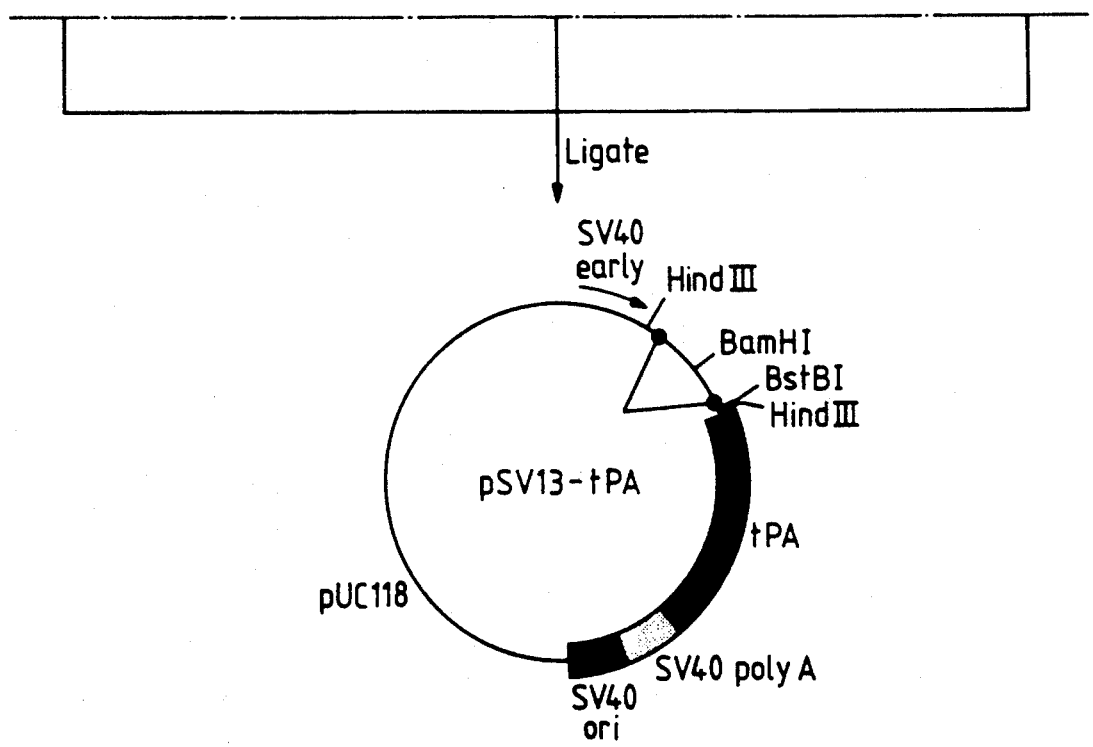

The vector pSVI3-tPA was prepared as shown in FIG. 4. Two adjacent regions of pSVI2-tPA were amplified by PCR using in each case one oligonucleotide identical to the pSVI2-tPA sequence and one mutant oligonucleotide specifying the desired changes. These fragments were used to replace the corresponding regions in pSVI2-tPA. The fragments isolated were as follows:

1. Vector pSVI2-tPA was designated with HINDIII, the digest treated with BAP, and the two HINDIII fragments were separated by gel electrophoresis. The larger fragment was recovered form the gel; it contained all pSVI2-tPA sequences, except for the 237-nucleotide HINDIII fragment that includes the splice donor-intron-splice acceptor unit.

2. A new oligonucleotide (SVI525Bam) was synthesized for PCR mutagenesis of the ATG trinucleotide within the pSVI2-tPA intron. It was identical in sequence to the lower strand of pSVI2-tPA from nucleotide 525 to nucleotide 497, except for a T to A change at position 516, an A to C change at position 519, and a T to G change at position 523. The first change was designed to alter the ATG trinucleotide to TTG; the second and third to create the recognition sequence for the enzyme BamHI (GGATCC). The nucleotide sequence of SVI525Bam was as follows (differences from the pSVI2-tPA sequence underlined):

5'-TAGGATCCAAAAGGTTATGTAT-TAATTGT-3'.

Oligonucleotides SVI379 (see above) and SVI525Bam were used to amplify by PCR mutagenesis the region between positions 379 and 525 of pSVI2-tPA while incorporating the changes specified by SVI525Bam. The reaction products were digested with HINDIII and BamHI and the resulting 137-nucleotide fragment was gel isolated.

3. Oligonucleotide SVI539Bam was synthesized for PCR mutagenesis of the pSVI2-tPA branchpoint region. It corresponded to the pSVI2-tPA sequence (upper strand ) from position 539 to position 573, but had the following changes: a G in place of the T at 541; a T in place of a C at 544; a C in place of an A at 545; a C in place of an A at 553; and a G in place of an A at 555. The first three changes created a BamHI recognition site, while the last two were intended to generate a signal resembling the branchpoint sequence (BPS) consensus. The nucleotide sequence of SVI539Bam was as follows (changes from the pSVI2-tPA sequence underlined);

5'-GGGGATCCTATAGACTGACATC-CACTTTGCCTTTC-3'.

Oligonucleotide SVI625 was synthesized and was identical to the lower strand of the pSVI2-tPA sequence from position 625 to position 603, except for an A to C change at position 617, designed to generate a BstBI restriction site (TTCGAA). The sequence of SVI625 was (change underlined):

5'-CCAAGCTTCGAACCGAGGTGCAG-3'.

Oligonucleotides SVI539BMA and SVI625 were used to amplify by PCR the region of pSVI2-tPA between nucleotides 539 and 625 and concurrently incorporate the desired changes. The PCR products were digested with HindIII and BamHI, and the 77-nucleotide fragment was gel purified.

The three fragments (FIG. 4) were ligated and as such were introduced into E. coli MM294. Plasmid DNA was isolated from a number of ampicillin-resistant colonies and analyzed by digestion with appropriate restriction enzymes and gel electrophoresis for the presence of all three fragments in one copy each. The relative orientation of the fragments was also determined by this analysis. The nucleotide sequence of one recombinant plasmid (pSVI3-tPA), which had the three constituent fragments arranged in the same order as in pSVI2-tPA, was determined in the region spanning the three sites of recombination (the two HindIII sites and the BamHI site), including all sequences between these sites.

d. pSVI5-tPA

Figure 5:
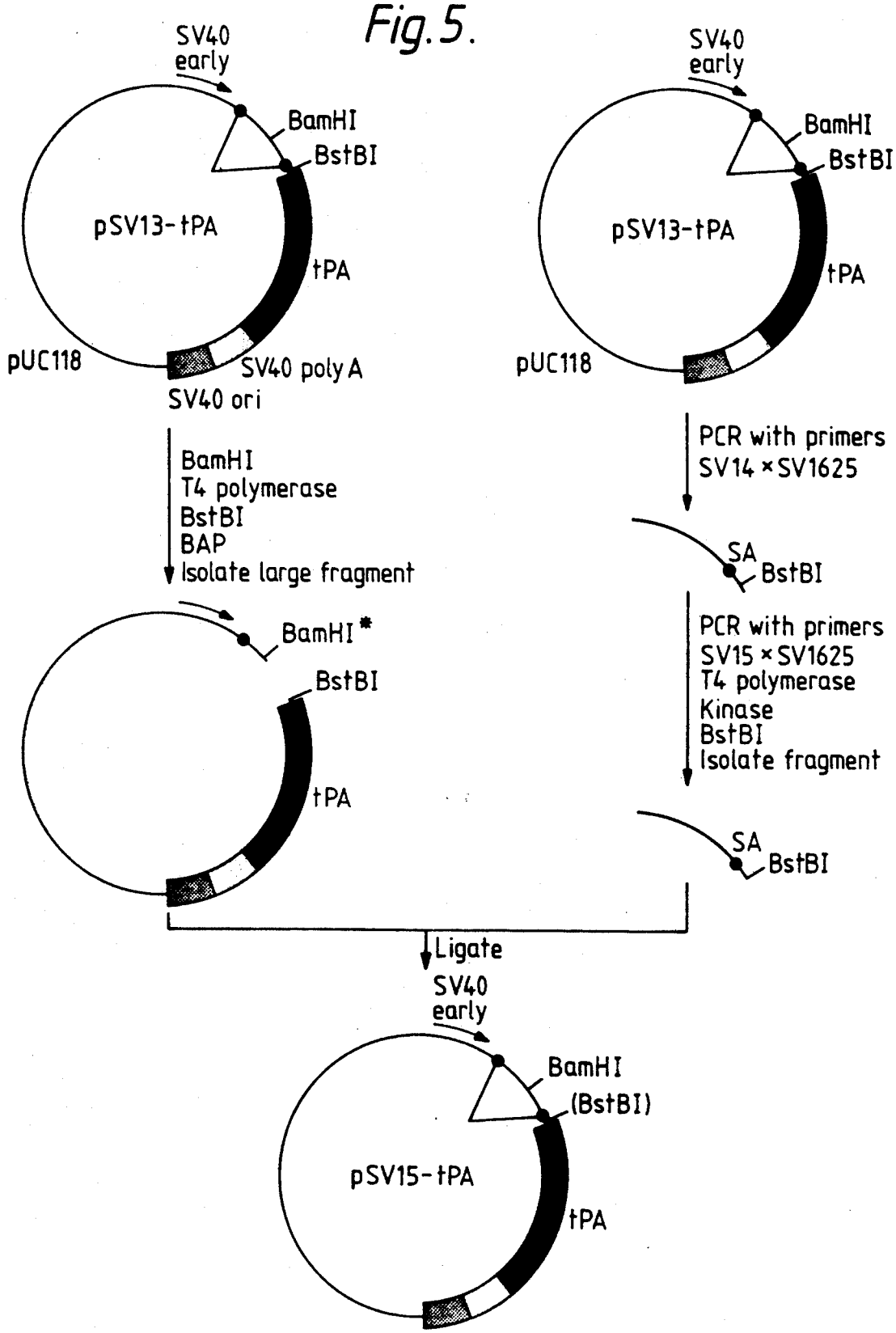
FIG. 5 shows the construction of the vector pSVI5-tPA.

Vector pSVI5-tPA was constructed from pSVI3-tPA by replacing a portion of the intron and the splice acceptor with a PCR-generated mutant fragment (as shown in FIG. 5). Nucleotide −16 (G) relative to the 3' splice junction of pSVI3-tPA was modified to the nucleotide T to create an uninterrupted 16 nucleotides long polypyrimidine tract as part of the splice acceptor. The vector also was modified to contain a potential branch acceptor nucleotide at position −23 relative to the 3' splice junction, embedded within the sequence GACTTATT, which is complementary to the splice donor sequence (G/GTAAGT) in this vector. Overlapping this BPS is another BPS (TACTGAC) that conforms to the "wide" BPS consensus and is complementary to the U2 snRNA sequence. The branch acceptor nucleotide in this BPS is located at position −27 relative to the 3' splice junction. Finally, the vector is modified by the insertion of a third BPS just upstream of the two BPSs in pSVI3-tPA. This third BPS is identical to the conserved yeast BPS (UACUAAC) and confirms to the "wide" mammalian BPS consensus (PyNCUPuAC). The branch acceptor in this BPS is located at position −34 relative to the 3' slice junction.

The fragments for generating pSVI5-tPA were prepared as follows:

1. Vector pSVI3-tPA was digested with BamHI and the resulting 5' protruding ends were filled in with T4 DNA polymerase in the presence of all four dNTPs. The material was subsequently digested with BstBI, treated with BAP, and the larger fragment containing all but part of the intron and the splice acceptor sequence of pSVI3-tPA gel isolated.

2. Two new oligonucleotides were synthesized for use in successive PCR amplifications without intermediate product isolation. This approach to introduce a variety of mutations was taken to avoid the use of a single long oligonucleotide with numerous mismatches to the target; longer synthetic oligonucleotides often contain a greater proportion of molecules of incorrect sequence. In addition, the fist oligonucleotide alone could in the future be used to create a vector differing from pSVI3-tPA in the branchpoint and splice acceptor regions.

The first oligonucleotide, SVI4, had its 3' terminal thirteen nucleotides in common with pSVI3-tPA (positions 545-557). Preceding these were 22 nucleotides of sequence similar, but not identical, to the pSVI3-tPa sequence between positions 523 and 544. The differences were as follows (underlined below): a G to T change at position 528; an A to T at 535, a C to A at 537, a C to T at 538, and an A to T at 539; and a G to T change at position 544. The last change could cause an extension of the polypyrimidine tract of the splice acceptor; the first would alter the pSVI3-tPA sequence GACTGAC to conform to the BPS consensus sequence that matches U2. The remaining four single nucleotide changes were designed to create a sequence complementary to the splice donor. The sequence of SVI4 was:

5'-CTATATACTGACT-
TATTCTTTTCCTTTCTCTCCAC-3'.

The second oligonucleotide (SVI5) overlapped the central portion of SVI4. It differed in the five 5' terminal nucleotides of SVI4 and extended in the 5' direction to incorporate the yeast BPS (TACTAAC). Its sequence was (underlined are the differences from the corresponding pSVI3-tPA sequence):

5'-CTACTAACTACTGACTTATTCTTT-3'.

The BPS/splice acceptor region of pSVI3-tPA was amplified and mutated by PCR mutagenesis using the oligonucleotide pair SVI4/SVI625. The PCR products were diluted and reamplified with oligonucleotide pair SVI5/SVI625. The products were treated with T4 DNA polymerase and T4 polynucleotide kinase and cleaved with restriction enzyme BstBI, and the 71-nucleotide fragment was gel isolated.

The two isolated fragments (FIG. 5) were ligated, and plasmid DNA was obtained from transformed (ampicillin-resistant) bacterial colonies and analyzed as described above for pSVI3-tPA. One isolate that carried all the desired intron changes was designated pSVI5-tPA.

Figure 6:
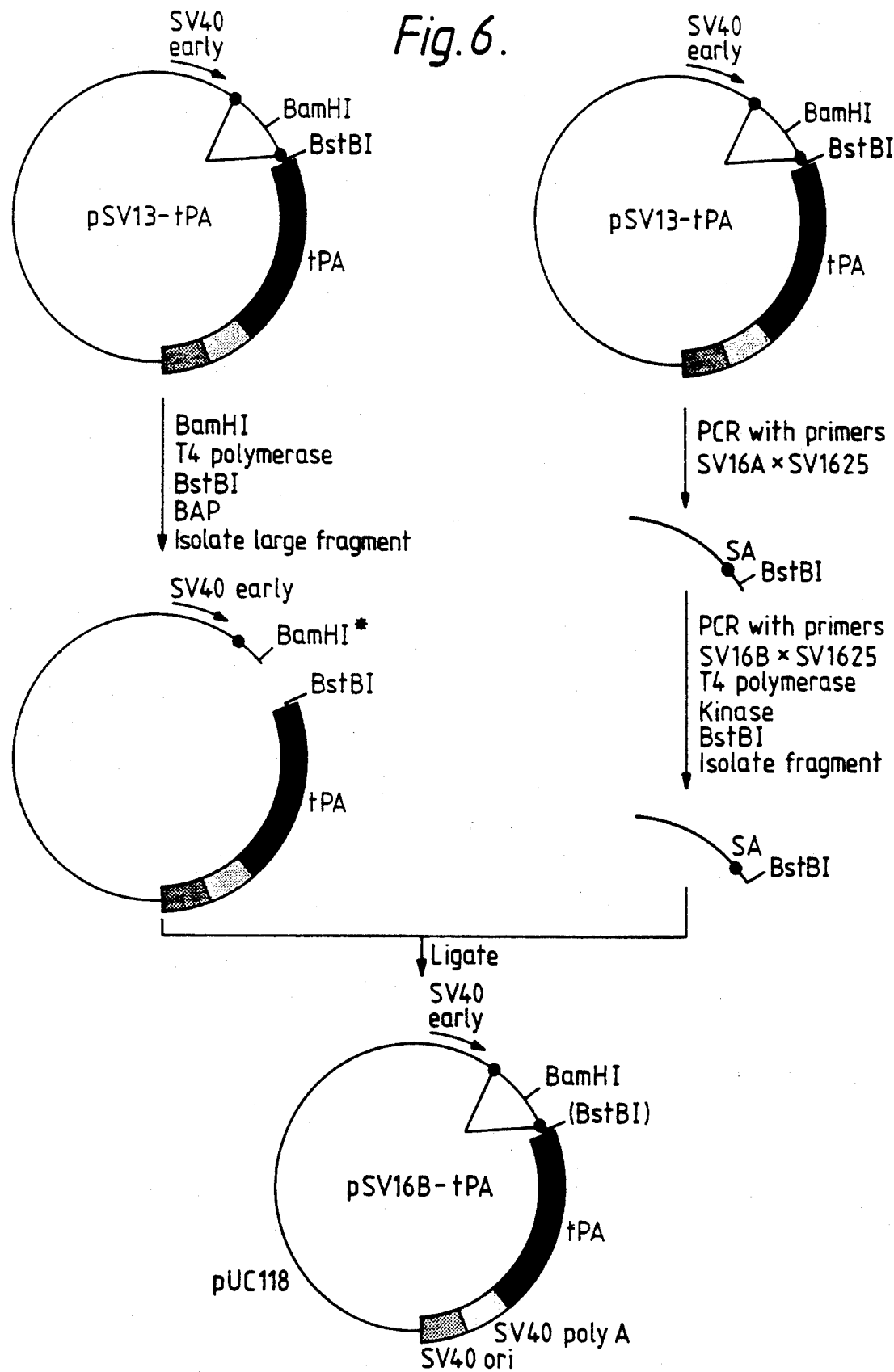
FIG. 6 shows the construction of the vector pSVI6B-tPA.

Sequence determination identified an additional unforeseen change outside of the splice donor-intron-splice acceptor unit. Two additional nucleotides (GC) were present in pSVI5-tPA within the BstBI site of pSVI3-tPA (TTCGAA changed to TTCGCGAA), which site was therefore absent form pSVI5-tPA. The two additional nucleotides, however, created a recognition site for the enzyme NruI, which is unique in the vector. The additional nucleotides most likely resulted from an unanticipated filling-in of the BstBI protruding ends of the two constituent fragments used for ligation.

e. pSVI6B-tPA pSVI6B-tPa was created by an approach similar to the one described above for pSVI5-tPA, using two successive amplifications with partially overlapping mutant oligonucleotides to generate the desired changes in the intron-splice acceptor region of pSVI3-tPA (as shown in FIG. 6).

The first oligonucleotide (SVI6A) had the following sequence (differences from pSVI3-tPA, positions 523-550, underlined):

5'-CCTGACACTGACATCCACTTTTCCTTTC-3';

and the second (SVI6B; compare to positions 523-545 of pSVI3-tPA):

5'-CTACTGACACTGACATCCACTTTTC-3'.

Nucleotide replacements in SVI6A were: T to C at 524, T to G at 526, G to C at 528, and G to T at 544. The changes specified by SVI6B were: insertion of a C between nucleotides 525 and 526 of pSVI3-tPA, insertion of a G between nucleotides 526 and 527, replacement of the G at position 528 by a C, and the G to T change at position 544. These changes were designed to optimize the pSVI3-tPA BPS and introduce a second BPS just flaking it to the 5' side; these two branchpoint sequences overlap at the central C and are shown in italics in the SVI6B sequence.

Successive amplifications with oligonucleotides SVI6A and SVI6B in the presence of SVI625 were performed to modify the pSVI3-tPA intron-splice acceptor unit as described for pSVI5-tPA. Enzymatic treatment of the PCR products, gel isolation, and ligation to the pSVI3-tPA large BamHI-BstBI fragment were also as described for pSVI5-tPA. Nucleotide sequence analysis of plasmid DNA from one ampicillin-resistant bacterial colony (this plasmid isolate was designated pSVI6B-tPA) showed several unanticipated changes in addition to the modifications specified by the SVI6B oligonucleotide; position 545 was a T rather than the C of pSVI3-tPA; position 550 was also a T rather than a C; and the additional dinucleotide creating the NruI restriction site in pSVI5-tPA was also present in the pSVI6B-tPA sequence. The first two changes would not be expected to affect adversely t-PA expression and were not corrected.

Construction of Broadly Applicable Parental Vector pSVI6B5

A broadly applicable parental vector for expression of different polypeptides was derived form pSVI6B-tPA. This vector, called pSVI6B5 (transformed *E. coli* strain ATCC No. 68, 151) carries polylinker regions in place of the t-PA cDNA in pSVI6B-tPA. These polylinker regions provide convenient, unique restriction endonuclease recognition sites that can be used to introduce any sequence that encodes a polypeptide of interest.

Vector pSVI6B5 was generated in four steps, as described below. The first three steps involved the removal of the BamHI, HindIII, and SalI restriction sites, respectively, from pSVI6B-tPA; as a consequence, upon replacement of the t-PA cDNA by the polylinker in the last step, the polylinker sites for these enzymes were unique in the resulting parental expression plasmid.

a. Construction of first intermediate plasmid pSVI6B-tPAd(b)

Vector pSVI6B-tPA was digested with BamHI, which cleaves only within the intron, the resulting 5' protruding ends were filled in with T4 DNA polymerase in the presence of dNTPs, and the linearized vector was gel isolated and treated with T4 DNA ligase to recirculsize. This caused the loss of the BamHI recognition sequence; instead, the recognition sequence for the enzyme ClaI was created. However, due to methylation, ClaI is unable to cleave this sequence when plasmid DNA is obtained from dam+ E. coli.

b. Construction of second intermediate plasmid pSVI6B-tPAd(bh)

Plasmid pSVI6B-tPAd(b) was digested with HindIII, which cleaves to both sides of the splice unit, the 5' protruding ends wee filled in with T4 DNA polymerase in the presence of all four dNTPs, and part of the reaction mixture was treated with BAP. The two fragments present in both the treated and untreated material were separated by gel electrophoresis; the larger fragment was isolated from the treated material, and the smaller fragment from the untreated material. The two fragments were ligated to create plasmid pSVI6B-tPAd(bh). Filling in of the HindIII ends of both constituent fragments caused the loss of the two HindIII sites in the resulting plasmid and concurrently created two new recognition sites for the enzyme NheI.

c. Construction of third intermediate plasmid pSVI6B-tPAd(bhs)

The single SalI recognition site was removed from plasmid pSVI6B-tPAd(bh) by digestion with this enzyme, T4 DNA polymerase treatment in the presence of dNTPs, gel isolation of the linear plasmid DNA, and recircularization using T4 DNA ligase. This resulted in the creation of a new PvuI recognition site.

d. Construction of plasmid pSVI6B5

For generation of the final, multi-purpose parental plasmid, two fragments were prepared as follows:

1. Plasmid pSVI6B-tPAd(bhs) was digested with PstI and ClaI. There are three recognition sites for ClaI in this plasmid: one in the intron preceding the t-PA sequence, one at the boundary of the t-PA cDNA and the SV40 early polyA region, and one towards the end of the polyA region. Only one of these sites, the second, is insensitive to methylation. Consequently, plasmid DNA prepared from dam+ MM294 was cleaved by ClaI only at this site. A Pst recognition site is located at the junction of the splice unit and the t-PA cDNA, and several more are present in the t-PA sequence between this position and the methylation-insensitive ClaI site. Cleavage with PstI and ClaI thus resulted in the release of several smaller fragments containing t-PA sequences, and a large fragment containing all pSVI6B-tPAd(bhs) sequences with the exception of the t-PA cDNA. This larger fragment was gel isolated.

2. Two ligonucleotides were synthesized. These were complementary over the entire length (47 nucleotides) of the first (designated 5A). The second, 5B, was extended at its 5' end by two nucleotides, and at its 3' end by four (underlined in the 5B sequence below). Annealing of these complementary oligonucleotides thus resulted in a DNA fragment having one 5' and one 3' protruding and ("overhang"). The sequence of the four-nt 3' protruding end was TGCA-3', which is complementary to the 3' overhang created by PstI cleavage of PstI recognition sites. The two-nt 5' protruding end consisted of the dinucleotide 5'-CG, which is complementary to the 5' overhang created by ClaI cleavage or ClaI restriction sites. The sequences of the two oligonucleotides were further designed to provide recognition sites for a number of restriction endonucleases (some of these are indicated under the sequence of each oligonucleotide shown below). The sequence of oligonucleotide 5A was:

5'-TCGATTGAATTCCCCGGGGATCCTCTAGAGTCGACCTGCAGAAGCTT-3'.
      EcoRI  SmaI  BamHI  XbaI  SalI  PstI  HindIII The sequence of oligonucleotide 5B was:

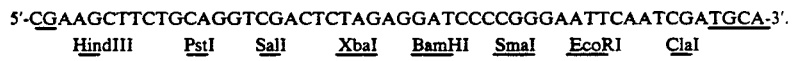

5'-CGAAGCTTCTGCAGGTCGACTCTAGAGGATCCCCGGGAATTCAATCGATGCA-3'.
  HindIII  PstI  SalI  XbaI  BamHI  SmaI  EcoRI  ClaI Oligonucleotides 5A and 5B were annealed and ligated to the isolated pSVI6B-tPAd(bhs) fragment to create plasmid pSVI6B5. Ligation of the PstI overhang to the TGCA-3' overhang of the annealed oligonucleotides did not regenerate a PstI site, but created a ClaI site; at the other end of the linker, ligation of the ClaI overhang to the 5'-CG overhang did not regenerate a ClaI site.

EXAMPLE 2

Construction of HPg and R561SPg Expression Vectors, CHO Cell Transformation Therewith, and Purification General Methods The oligonucleotides used for the mutageneses of the cDNA for this example and subsequent examples were synthesized using either (1) phosphoramidite chemistry on a Biosearch (San Rafael, Calif.) Cyclone two-column DNA synthesizer, with purification using the Applied Biosystems (Foster City, Calif.) oligonucleotide purification cartridges, or (2) H-phosphonate chemistry as described by Froehler et al., *Nucl. Acids. Res.*, 14: 5399–5407 (1986).

Cell transfections were performed by the calcium phosphate method (Kingston, in *Current Protocols in Molecular Biology*, supra).

Plasmid DNAs were purified by CsCl/ethidium bromide (EtBr) gradient centrifugation (Moore, in *Current Protocols in Molecular Biology*, Ausubel et al., eds. (John Wiley & Sons, New York, 1987), p. 1.7.1–1.7.4), with a Beckman (Palo Alto, Calif.) L5 65 preparative ultracentrifuge. A vertical rotor (Vti.65.1) centrifugation was employed for 7 hr. at 55,000 rpm, and at 15° C., to separate the DNA bands. After the desired material was obtained from the centrifuge tube, EtBr was removed form the plasmid DNA by extraction into a solution of isopropanol saturated with CsCl. The DNA was then dialyzed against a buffer of 1 mM Tris-HCl/0.1 mM EDTA, pH 7.1, prior to cell transfections.

Construction of R561S Expression Vector pA475R561SPg

A plasmid designated pUC119PN127.6 (the sequence of which is shown in FIG. 1 with the exception noted above regarding nucleotide 3809) was prepared as follows. A first cDNA was isolated from an n-oligo-(dT)-primed cDNA library constructed from liver mRNA isolated from five individuals. [Okyama et al., *Mol. Cell. Biol.*, 2: 161-170 (1982) and Gubler et al., *Gene*, 25: 263-269 (1983)]. Size-selected cDNAs (greater than 600 base pairs) were ligated into λgt10 bacteriophage vectors (Stratagene, San Diego, Calif.), and screened without amplification [Drayna et al., *Nature*, 327: 632-634 (1987)]. The cDNA was ligated to the γgt10 vector using a linker as follows.

```
              Eco RI    Sac I/Sst I  Sal I
λgt10:      GAATTCT    CGAGCTC    GTCGACC: cDNA
```

A λgt10 cDNA clone was recovered with a 75-base oligonucleotide probe (PL.1), corresponding to nucleotides 1, 306-1,380 of human plasminogen cDNA [Forsgren et al., *FEBS Lett.*, 213: 254-260 (1987)]. Filters were hybridized in 5×SSC (150 mM NaCl, 15 mM trisodium citrate), 50 mM sodium phosphate (pH 6.7), 5×Denhardt's solution, 20% formamide, 10% dextran sulphate, and 20 µg/ml of boiled, sonicated salmon sperm DNA at 42° C. overnight and washed for one hour in 2×SSC, 0.1% SDS at 55° C. and exposed to X-ray film. A λgt10 clone (designated λgt10:pmgn#127) was cut with SstI and ligated to SstI-cut pUC119 to give pUC119PN127.6, a nucleotide and a deduced amino acid sequence for which is illustrated in FIG. 1, with the exception noted above. The nucleotide sequence of the [Glu$^1$]Pg in pUC119PN127.6 showed the presence of Val$^{475}$ in place of Ala.

The clone was sequenced to completion. DNA sequence analysis was performed by the dideoxy chain termination method on both strands of the subcloned double-stranded cDNA [Sanger et al., *Proc. Natl. Acad. Sci. USA*, 74: 5463-5467 (1977)] either directly on double-stranded DNA or single-stranded templates [Chen et al., *DNA*, 4: 165-170 (1985)] after subcloning into a pUC119 vector.

Figure 7:
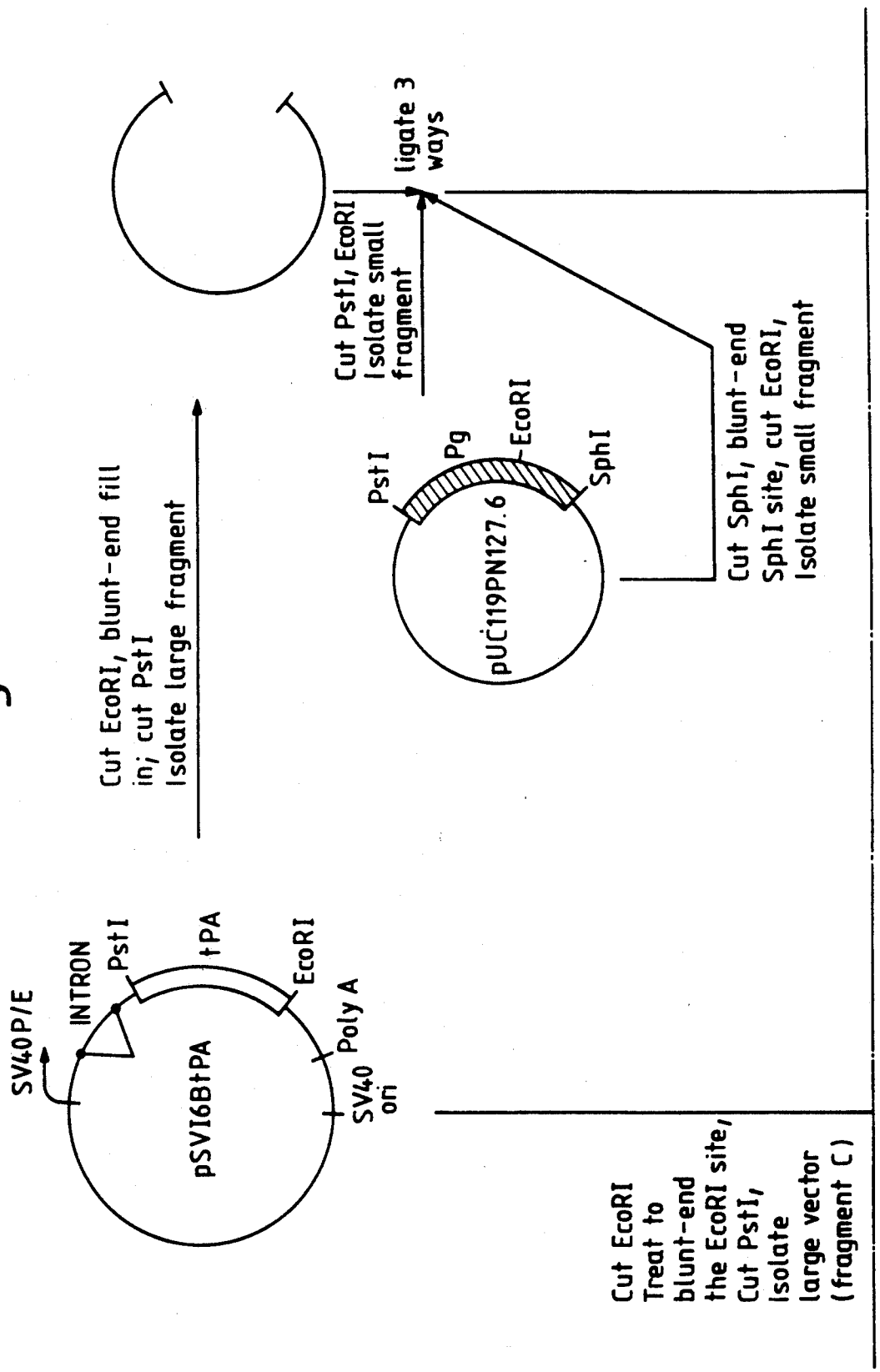
FIG. 7 shows the construction of pA475R561SPg used for expression of a HPg variant in accordance with this invention.

The vector pA475R561SPg containing the correct human Pg sequence except with a serine at position 561 was constructed as follows, and as shown in FIG. 7:

pSVI6BtPA was digested with EcoRI, filled in to blunt end the EcoRI site and then cut with PstI and the large fragment was isolated. pUC119PN127.6 was cut with SphI and filled in to blunt end the SphI site, and then cut with EcoRI, and the small fragment encompassing the 3' end of HPg cDNA was isolated; pUC119PN127.6 was also cut with PstI and EcoRI and the small fragment was isolated that encompassed the full 5' end of cDNA encoding HPg. These two small fragments and the large fragment from pSVI6BtPA were ligated together using T4 ligase to produce the plasmid pSVI6BPlgn. This plasmid was cleaved with PstI and EcoRI and the small fragment (248-bp) was isolated (fragment A). pSVI6BPlgn was also subjected to site-specific mutagenesis of the cDNA for HPg using the method of Kunkel et al., *Meth. Enzym.*, 154: 367-382 (1987) and using a primer for the R561S change as follows:

```
5'-ACCCCCCTACAACGGATCCAG-
   GACATTTCTTC-3'.
```

The colonies were screened by the presence of the new BamHI restriction endonuclease site also inserted in the cDNA as a result of these mutations. The resulting plasmid was designated pSVIR561SPg.C2. This plasmid was cut with SphI, and filled in to blunt end the SphI site, and cut with EcoRI and the small fragment (2.32 kb) was isolated (fragment B). The third fragment was prepared from pSVI6BtPA by cleaving this plasmid with EcoRI, and filled in to blunt end the EcoRI site and cut with PstI, and isolating the large fragment (Fragment C).

Fragments A, B, and C were ligated with T4 ligase to yield the plasmid pR561SPg containing the vector elements of pSVI6BtPA and the mutagenized plasminogen.

Other expression vectors could be utilized in place of pSVI6BtPA as the vector source. For example, pE342-tPA (U.S. Pat. No. 4,766,075) could be employed as the vector fragment by replacing the t-PA-encoding DNA of pE342-tPA with the plasminogen cDNA from pUC119PN127.6. Thus, regulatory elements from other expression vectors may be operably linked to the HPg cDNA as would be known to those skilled int he art to produce a HPg expression vector.

The final vector, pA475R561SPg, was prepared as follows: pR561SPg was cleaved with AhaII and EcoRI and the small mutagenized Pg fragment (1003 bp) was isolated (Fragment D). Also, pSVI6BPlgn was cleaved with SmaI and EcoRI and the vector fragment (4.394 kb) was isolated (Fragment E). Finally, pSVI6BPlgn was subjected to site-directed mutagenesis of the cDNA for HPg using the method of Kunkel et al., supra, with the following mutagenic primer (the underlined bases represent the mutations imposed) to make the V475A mutation:

```
5'-GTAACAGTGGTTGCCCTCTTGCCTC-3'.
```

Positive colonies were screened using an EcoRI/BstEII restriction endonuclease digest. Clones with the proper size fragments were sequenced over the region corresponding to amino acid positions 455-502.

The thus mutagenized pSVI6BPlgn was cut with SmaI and AhaII and the small fragment (1.55 kb) isolated (Fragment F). Fragments D, E, and F were ligated to produce the final plasmid, pA475R561SPg.

Construction of Plasminogen Expression Vector pA475Pg

A plasmid containing the A475 mutation without the R561S mutation (i.e., containing native-sequence plasminogen) was prepared as follows: pSVI6BPlgn was cut with AhaII and EcoRI and the small fragment was isolated (Fragment G). Fragments E and F (described above) and G were ligated to produce plasmid pA475Pg.

Construction of PAI-1 Expression Vector pRKPAI-1

An expression vector encoding the human β-migrating endothelial-cell-type plasminogen activator inhibitor (PAI-1) was constructed as follows: The cloning and sequence of PAI-1 are described by Ny et al., *Proc. Natl. Acad. Sci. USA*, 83: 6776-6780 (1986); Ginsberg et al., *J. Clin. Invest.*, 78: 1673-1680 (1986); Pannekoek et al., *EMBO J.* 5: 2539-2544 (1986). The PAI-1 cDNA was obtained form a human umbilical endothelial cell cDNA library as a λ clone and placed in a pUC18 cloning vector that replicates in *E. coli*. This plasmid was cut with BglII, blunt-ended, and cut with EcoRI. The small fragment, about 1430 bp, was gel purified. pRK5 was also cut with SmaI, then with EcoRI, and a vector fragment of 4712 bp was isolated and gel purified. These two fragments were ligated together using T4 ligase, and digests of minipreps were performed to confirm the orientation of the insert. The final vector is designated as pRKPAI1.

Transformations with pA475R561SPg or pA475Pg

CHO dhfr⁻ cells (Urlaub and Chasin, supra) were set in 60-mm plates at 5×10⁵ cells/plate, in duplicate. DNAs were transfected by the calcium phosphate protocol with the following combinations of plasmids:
(a) pA475R561SPg (50 μl or 5 μg/plate), pRKPAI-1 (4.2 μl or 5 μg/plate), and pFD11 (a DHFR-encoding plasmid described by Simonsen and Levinson, *Proc. Natl. Acad. Sci. USA*, 80: 2495-2499 (1983)), 6 μl or 0.5 μg/plate);
(b) pA475R561SPg (50 μl or 5 μg/plate) and pFD11 (6 μl or 0.5 μg/plate);
(c) pA475Pg (50 μl or 5 μg/plate), pRKPAI-1 (4.2 μl or 5 μg/plate), and pFD11 (6 μl or 0.5 μg/plate); or
(d) pA475Pg (50 μl or 5 μg/plate) and pFD11 (6 μl or 0.5 μg/plate).

The cells were split into selective culture medium containing 7% diafiltered fetal bovine serum at 0.1, 0.1, 0.1, 0.2, 0.2, and 0.3 μg of plasmid per 60-mm plate. Twelve days later one plate each of the four transformations (a-d) was washed with phosphate buffered saline and fed with selective culture medium and 7% plasminogen-depleted fetal bovine serum. This step removed any plasminogen that was not being produced by the cells. Clones producing plasminogen were screened by the amount of expression on the filters. Three clones of each of transformations a-d were picked with swabs into a 12-well plate. These twelve clones were grown in 10-cm plates and the medium was exchanged with a non-selective culture medium.

The harvested medium was subjected to ELISA protein determination. It was found that the pA475R561SPg and pRKPAI-1 clone #2 gave activity of at least 1 mg/l. Five roller bottles of the R561S-HPg material were produced for purification. R561S-HPg was purified from the CHO culture supernatant by affinity chromatography on Sepharose-lysine according to the method of Deutsch and Mertz, *Science*, 170: 1095-1096 (1970) as modified by Brockway and Castellino, *Arch. Biochem. Biophys.*, 151: 194-199 (1972).

EXAMPLE 3

Construction of R561EPg Expression Vector, Insect Cell Transformation Therewith, and Purification The general methods described in Example 2 were also employed in this example.

Construction of HPg and R561E-HPg Baculovirus Expression Vectors

The cDNA encoding HPg in the plasmid pUCb 119PN127.6 (in the BamHI/NaeI fragment) was mutagenized as described in Example 2 to generate the V475A change as described in Example 2 to create native-sequence Pg. The resulting plasmid was mutagenized as described in Example 2 to generate the R561E change using the mutagenic primer:

5'-CCCCCCTACAACCCTCCCG-
GGACATTTCTTCGG-3'.

Figure 8:
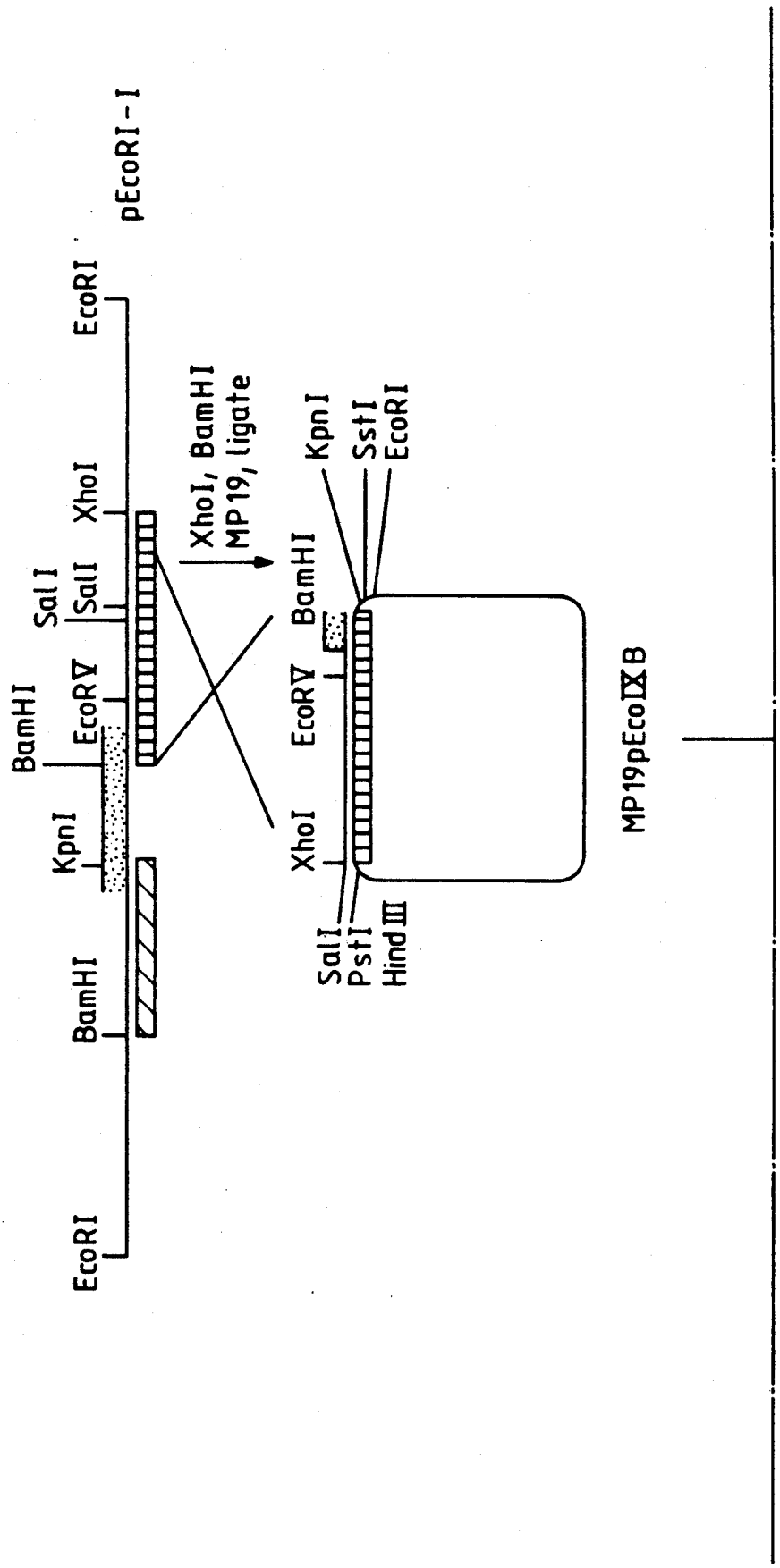
FIG. 8 is a flow chart that schematically depicts the construction of the baculovirus transfer vector pAV6 used for insect cell expression.

Positive colonies for this mutation were screened for the presence of the newly generated SmaI restriction endonuclease cleavage site that accompanies the alteration made. The recombinant baculovirus transfer vector pAV6 into which the A475HPg cDNA and A3475, R561EHPg cDNA were inserted was constructed to include DNA sequences surrounding the AcMNPV polyhedrin (PH) gene. pAV6 contains the polyhedron promoter in 1.8 kb from a HboI site located 5' of the PH gene to nucleotide −8 of the polyhedron initiation codon (ATG), and also includes a 1.5-kb fragment extending from a KpnI site within the polyhedron gene to a BamHI site 3' of this same gene. The XboI and BamHI sites were lost during closing of these fragments.

pAV6 was constructed as follows and as illustrated i FIG. 8. A 7.2-kb EcoRI fragment of *Autographa californica* DNA designated pEcoRI-I [Smith et al., *J. Virol.*, 45: 215-225 (1983); Smith et al., *J. Virol.*, 46: 584-593 (1983)], containing the polyhedron gene and flanking sequences, was cut with XhoI and BamHI (SalI and XhoI digestions produce compatible end). The resulting XhoI/BamHI fragment was ligated into a SalI- and BamHI-cut mp19 vector (Bethesda Research Laboratories, Gaithersburg, Md.) to form a construction designated mp19Xho-Bam. The plasmid mp19Xho-Bam was cut with EcoRV and KpnI, and a first synthetic oligonucleotide (constructed, as were all oligonucleotides referred to below, on a 380 A model automated DNA synthesizer available form Applied Biosystems, Foster City, Calif.) was ligated into the cut mp19Xho-Bam to produce a vector designated mp19A1D. The first synthetic oligonucleotide had the following sequence, including the indicated restriction and transcription initiation sites.

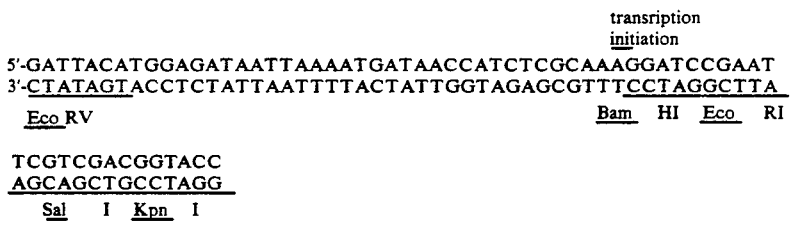

The first synthetic oligonucleotide replaced a sequence at the 5' end of the XhoI/BamHI fragment in mp19Xho-Bam from an EcoRV site to a putative CAP site and includes a multiple cloning site having BamHI, EcoRI, SalI, and KpnI sites.

Next, a pUC12 vector (Bethesda Research Laboratories) was cut with HindIII and stI, mp19A1D was cut with HindIII and KpnI, and a 1.8-kb fragment containing sequences flanking the 5' end of the polyhedron gene was isolated. The plasmid pEcoRI-I was cut with BamHI and KpnI and, from among the digestion products, a 1.5-kb fragment, extending from the KpnI site within the polyhedrin gene to a BamHI site in the 3' flanking region thereof, was isolated. These three fragments (pUC12, 1.8 kb, and 1.5 kb) were ligated along with a second synthetic oligonucleotide having the sequence 5'-GATCAGCT, to produce a construction designated pAV1.

After pAV1 was cut with BamHI and KpnI, the resulting fragment was ligated to a third synthetic oligonucleotide to produce a construction designated pAV2. The third synthetic oligonucleotide had a nucleotide sequence as follows:

```
5'-GAT CTA GAT CTG AGC TCG CGA TGG ATC CCG GGT AAC CGG TAC
3'-AT CTA GAC TCG AGC GCT ACC TAG GGC CCA TTG GC
```

A plasmid, pDS, was constructed by cutting pBR32 (the 4.4-kb plasmid available form Bethesda Research Laboratories) with HindIII and SalI, filling in with Klenow fragment, and ligating. Thus, the plasmid pDS lacks the sequences between HindIII and SalI and loses the SalI site, but maintains the HindIII site.

The plasmid pAV2 ws cut with HindIII and BamHI, and a 1.5-kb HindIII/BamHI fragment (containing the 5' flanking sequence) was isolated. Next, pAV2 was cut with BamHI and EcoRI, and a 1.5-kb EcoRI/BamHI fragment extending form the BamHI site in the multiple cloning site to the EcoRI site adjacent to the 3' flanking sequence was isolated. The plasmid pDS was cut with HindIII and EcoRI and ligated to the two fragments made from pAV2. The resulting plasmid was designated pAV3.

The plasmid pAV3 was cut with BamHI and SalI. A vector pAC373 [Smith et al., *Mol. Cell. Biol.*, 3: 2156-2165 (19783)] (containing NPV viral DNA from a SalI site about 1 kb 5' of the polyhedron gene to a BamHI site inserted at nucleotide −8 (the "A" of the "ATG" initiation site being +1) was cut with BamHI and SalI and ligated to the BamHI/SalI-cut pAV3 to produce a vector designated pAV4.

The vector pAV4 was cut with EcoRI, and the ends were filled with Klenow fragment and ligated to produce the vector designated pAV6 (lacking the EcoRI site of pAV4). [The transfer vector pAV6HPg, which is made from insertion of a BamHI/NaeI fragment coding for native sequence HPg from pUC119PN127.6 into the BamHI and SmaI sites of plasmid pAV6, contains the AcMNPV polyhedrin (PH) promoter linked to the HPg signal and mature [Glu$^1$]Pg coding sequence. This plasmid ws deposited in the host *E. coli* DH5α on Apr. 18, 1989 with the American Type Culture Collection, 12301 Parklawn Drive, Rockville, Md. 20852, under Accession No. 67, 929. ]

The A475-HPg and A475, R561E-HPg cDNAs described above were inserted into the BamHI and SmaI sites of pAV6, t produce pAVA475Pg and pAVA475R561EPg, respectively, which were used to infect the culture media of *Spodoptera frugiperda* cells as described below.

Transformation of Insect Cells with Transfer Vector

The construct pAVA475Pg or pAVA475R561EPg and wild-type viral DNA were used to cotransfect cultured *Spodoptera frugiperda* cells, as described by Whitefleet-Smith et al., supra. In a cell, crossover between homologous polyhedron flanking regions of the transfer vector and the virus provides a full-length recombinant virus carrying the HPg gene in place of the PH gene.

The AcTR temperature-inactivation resistant strain of *Autographa californica* nuclear polyhedrosis virus (AcMNPV) was used as the host virus for recombinant constructions. A cloned (e.g., Sf9 cells, as available form the American Type Culture Collection, Rockville, Md. under accession number ATCC CRL 1711)or an uncloned *Spodoptera frugiperda* cell line may be employed to provide host cells for all virus growth and manipulations [Vaughn et al., *In Vitro*, 13: 213-217 (1977)]. The procedures employed for culturing insect cells are described in Summers et al., Texas Agricultural Experiment Station Bulletin No. 1555, (1987), at pages 10-31 and 38, except that Gibco powdered Grace's Anteraea medium, Hink's medium (instead of TNM-KH medium), and a penicillin/streptomycin/amphotericin B antibiotic mixture were employed in the procedure at page 38 thereof.

Specifically, *Spodoptera frugiperda* cells ($3 \times 10^5$), in Hink's medium [Hink, *Nature*, 226: 466-467 (1970)] plus 10% fetal bovine serum (FBS) [Smith et al., *Mol. Cell. Biol.*, supra], were allowed to adhere to a 60-mm culture dish. After two hours, the medium was removed and the cells were incubated in a 0.5-ml suspension of wild-type DNA from AcMNPV (0.1 μg) plus pAVR561EPg transfer plasmid DNA (1 μg) in NaCl (0.8 g/l), KCl (0.37 g/l)Na$_2$H$_2$PO$_4$·2H$_2$O (0.125 g/l), dextrose (1 g/l), and Hepes-NaOH (5 g/l) at pH 7.2. After incubation overnight at about 27° C., the DNA suspension was removed and the cells were incubated for five days in Hink's medium, plus 10% FBS.

*Spodoptera frugiperda* cells may also be cultured in suspension by employing Corning (New York, N.Y.) slow-speed stirring vessels on a Cellgro slow-speed magnetic stirrer (Thermolyne Corp., Bubuque, Iowa). To each 1000-ml stirring vessel, 300 ml of incomplete Hink's medium (supplemented with 8.3% FBS and the penicillin/streptomycin/amphotericin B mixture as above) are added. The vessel is then inoculated with $5 \times 10^6$ cells and stirred at 80 rpm. Cells are subcultured when they attain a density of $2-\times 10^6$ cells/ml by removing 150-250 ml of cell suspension and replacing it with fresh medium. Suspension-grown cells attach to flasks and may thus be used in procedures requiring monolayers.

Cells may also be grown in a defined, low-protein medium EX-CELL 400 produced by JR. Scientific, Woodland, Calif. This medium may be used in place of complete Hink's medium for culturing cells in monolayers, in spinner flask suspension cultures, or in air-lift bioreactors [q.v., Maiorella et al., *Biotechnology*, 6: 1406-1410 (1988)].

After growth, the recombinant proteins A475HPg and A475, R561E-HPg were purified by affinity chromatography s described for the CHO-expressed plasminogens above.

EXAMPLE 4

1. Amino Acid Sequencing

The plasminogen and mutants thereof produced in accordance with Examples 2 and 3 were subjected to amino terminal amino acid sequence analysis on a Porton Instruments gas phase sequencer, after adsorption of the protein onto the peptide support discs. PTH-amino acids were separated on a Beckman reverse phase ODS column (5 μ, 4.6 mm×250 mm), employing a Spectra Physics HPLC system. The latter consisted of a Model 8800 ternary HPLC pump, a Model 8480 UV/Vis detector, a Model 4270 recording integrator, and a PI2030 Interface for on-line injections of the samples onto the HPLC column. Resolution of the 20 PTH amino acids was accomplished at 55° C., under the following linear gradient conditions: 88% solution A (1 ml glacial acetic acid/20 ml tetrahydrofuran/0.05 ml triethylamine/water to 500 ml, pH adjusted to 4.10 with 3N NaOH)/12% solution B (1% tetrahydrofuran in acetonitrile) as the start solution, to 60% solution A/40% solution B (limit solution) over a period of 24.5 min. at a flow rate of 1 ml/min. Solution B was then continued for an additional 5.5 min. at the same flow rate, during which time the last four PTH-amino acids were eluted.

2. Western Blot Analysis

The protein samples of Examples 2 and 3 were separated by SDS/PAGE (Laemmli, *Nature*, 227: 680–685 (1970)) on 10% (w/v) polyacrylamide gels under non-reducing conditions. The separated protein bands were transferred to Immobilon-P (Millipore, Bedford, Mass.) membranes according to established procedures (Burnette, *Anal. Biochem.*, 112: 195–203 (1981)), and then incubated at 37° C. for one hour in 1% (w/v) gelatin (Bio-Rad EIA grade) in TBS (0.05M TrisHCl, 0.15M NaCl, pH 7.4, blocking buffer). The exact conditions for transfer were 4° C. in 25 mM Tris-HCl/200 mM glycine/15% (v/v) methanol, pH 8.3, at 20 volts for 12 hours. This solution was replaced with another containing 4 μg/ml of monoclonal murine anti-HPg (Whitefleet-Smith et al., supra) in blocking buffer, and incubated at room temperature for 2 hours with mixing. The filter was washed with three changes of 0.05% (v/v) Tween-20 in TBS at room temperature, over a 15-min. period. It was then incubated with rabbit anti-mouse IgG-alkaline phosphatase conjugate (Sigma) in blocking buffer for two hours at room temperature, with mixing, and then washed as above. Positive bands were visualized after incubations, at room temperature, with the substrate solution (16.5 mg nitro blue tetrazolium/0.5 ml of 70% (v/v) aqueous DMF/8.5 mg bromochloroindolyl phosphate in 1 ml in water, which was added to 50 ml of 0.1M Tris-HCl/0.1M NaCl/0.005M $MgCl_2$, pH 9.5).

3. Amidolytic Assays of Stoichiometric Complexes of SK-HPg and SK-HPm

A quantity of 0.2 ml of a buffer consisting of 100 mM Hepes-NaOH/10 mM EACA, pH 7.4 was placed in a spectrophotometer cuvette, maintained at 25° C. Then the desired concentration of the chromogenic substrate, H-D-Val-L-Leu-L-Lys-pNA (S2251, Helena Laboratories, Beaumont, Tex.) was added, followed by the required amount of water. The hydrolysis of the substrate was accelerated by the addition of the desired preformed stoichiometric SK-HPg or SK-Hpm complex (final concentration, 6–10 nM). The rate of hydrolysis of S2251 was recorded continually for 2–5 min at 405 nm. The absorbancies were converted to initial activation rates as described previously (Urano et al., supra), and the rate data were analyzed according to usual Lineweaver-Burk plots. The enzyme complexes were generated by incubation at 25° C. of stoichiometric amounts of streptokinase (SK) (prepared according to the method published by Castellino et al., *Meth. Enzymology*, 45: 244–257 (1976)) and the desired plasminogen of Examples 2 and 3.

4. Plasminogen Activator Assays of Stoichiometric Complexes of SK-HPg and SK-HPm A quantity of 0.2 ml of a buffer consisting of 100 mM Hepes-NaOH/10 mM EACA, pH 7.4 was placed in a spectrophotometer cuvette, maintained at 25° C. Then, 0.08 ml of S2251 (final concentration, 0.5 mM) was added, followed by the required amount of water, various concentrations of bovine plasminogen (BPg, purified form fresh bovine plasma using the same method as sued to purify the recombinant Pgs), and lastly, the SK-HPg or SK-HPm activator complex prepared as described above (final concentration 0.2 mM). The rate of activation of BPg was monitored in continuous assay (Urano et al., supra) by recording the release of a p-nitroanilide resulting form the hydrolysis of S2251 by the bovine plasmin generated. The data were analyzed by Lineweaver-Burk plots as published for previous studies of this type (Urano et al., supra). Under these conditions, BPg was not activated by SK alone.

5. Deglycosylation of HPg

The desired HPg preparation (in 10 mM sodium phosphate, pH 7.4) was treated with glycopeptidase F (Boehringer Mannheim, Indianapolis, Ind.) at a concentration of 0.4 units of enzyme/μg of HPg. The reaction was allowed to proceed for 24 hours at 37° C. These conditions were found suitable for removal of the $Asn^{89}$-linked carbohydrate from all of the samples investigated. The mixture was then subjected to centrifugation in molecular weight 10,000 cut-off (Centricon 10) microconcentrator tubes (Amicon, Danvers, Mass.) to separate the liberated oligosaccharide from the protein sample.

B. Results

Two recombinant human plasminogens were obtained from infection of insect cells with a recombinant baculovirus containing the wild-type A475 [$Glu^1$]Pg cDNA (providing wt-irHPg, Whitefleet-Smith et al., supra) and the cDNA for wild-type A475 HPg containing an R561E mutation in the protein (R561E-HPg). Another recombinant protein with the wild-type (A475 sequence) containing an R561S mutation was produced in CHO cells (R561S-HPg). Their electrophoretic behavior suggests that all these recombinant proteins were highly purified and possessed the molecular weight characteristics associated with human [$Glu^1$]Pg. For brevity, the A475 mutation is not mentioned in the discussion below, although it is present in all the recombinantly produced HPg proteins mentioned.

Amino-terminal amino acid sequence analysis of all plasminogens reported provides the sequence $NH_2$-Glu-Pro-Leu-Asp-Asp, suggesting that all have been correctly processed with regard to cleavage of the signal polypeptide and also suggesting that the small mobility differences between purified recombinant proteins and human plasma HPg may be reflections of slight molecular weight variations resulting from differences in glycosylation among the plasma-, insect cell-, and CHO-cell-derived plasminogens.

The steady-state amidolytic activities of stoichiometric complexes of SK with the recombinant wild-type and variant plasmin(ogen)s are listed in Table I, and compared with that of the stoichiometric complex of SK and human plasma-derived plasmin(ogen) (i.e., native human plasma [$Glu^1$]Pg, affinity chromatography form 1, purified as were the recombinant Pgs). Full amidolytic activity of each of the complexes developed in 1-5 min., and 5-min. incubation times were used to generate the enzymes used in this study.

TABLE I

Steady-State Kinetic Constants at 25° C. for the Amidolytic Activity toward S-2251 of Equimolar Complexes of SK with Plasminogens and Plasmins

| Activator Species | $K_m$ (mM) | $k_{cat}$ (min$^{-1}$) | $k_{cat}/K_m$ (mM min)$^{-1}$ |
|---|---|---|---|
| SK-HPm[a] | 0.35 ± 0.05 | 312 ± 16 | 891 |
| SK-wt-irHPm | 0.33 ± 0.04 | 312 ± 12 | 945 |
| SK-R561E-HPg | 0.17 ± 0.05 | 272 ± 18 | 1600 |
| SK-R561S-HPg | 0.28 ± 0.06 | 368 ± 20 | 1314 |
| SK-R561S-HPgΔCHO[b] | 0.50 ± 0.06 | 377 ± 18 | 734 |

[a]Human plasma plasmin.
[b]HPg variant deglycosylated at Asn[289].

In the case of wt-irHPg and human plasma HPg, SDS/PAGE analysis of the components of the complexes at 5-min. incubation times clearly showed that they were composed of SK and [Lys[78]]HPm, as expected (Bajaj and Castillino, *J. Biol. Chem.*, 252: 492–498 (1977)). For the activation-cleavage-site-variant plasminogens, the complexes consisted of SK and the relevant HPg, as also would be expected, since the nature of the mutation precludes the conversion of HPg to HPm within the complex.

The data of Table I show that the SK-HPm complexes, containing either human plasma HPm or wt-irHPm, possess virtually identical steady-state kinetic constants toward S2251. Similarly, amidolytic activity is present in the stoichiometric complexes of SK with the two variant HPg preparations, viz., R561E-HPg and R561S-HPg. Comparison of the values of the kinetic constants for these latter two SK-HPg complexes with those of the former SK-HPm complexes suggests that only small differences exist in the amidolytic steady-state properties of the various SK-HPg and SK-HPm complexes.

The equimolar SK complexes with either human plasma HPm or the insect-expressed HPm are nearly identical, demonstrating that the insect cells produce a protein comparable to the human plasma counterpart. The $K_m$ for the SK complex with the variant cleavage-site resistant irHPg is slightly lower than this value for the same complexes with either of the plasmins, suggesting possible kinetic differences in the SK-HPg complex, as compared to the SK-HPm complex.

For determination of whether the Asn[289]-linked carbohydrate of HPg played a role in the small differences observed in the steady-state amidolytic kinetic constants, R561S-HPg (from CHO cells) was deglycosylated with glycopeptidase F. The stoichiometric complex of SK with this form of HPg possessed only a slightly higher Km than its glycosylated counterpart, suggesting that the presence of the carbohydrate on Asn[289], at least with respect to the type present on the CHO cell-expressed material, does not play a large role in this kinetic property of the SK-R561S-HPg complex.

Table II provides steady-state kinetic parameters reflecting the respective abilities of the various preformed stoichiometric SK-HPg and SK-HPm complexes, at catalytic levels, to serve as activators of plasminogen. BPg has been selected as the source of plasminogen due to its insensitivity to activation by SK alone.

TABLE II

Steady-State Kinetic Constants at 25° C. for the Plasminogen Activator Activity Toward Bovine Plasminogen of Equimolar Complexes of SK with Plasminogens and Plasmins

| Activator Species | $K_m$ (mM) | $k_{cat}$ (min$^{-1}$) | $k_{cat}/K_m$ (mM min$^{-1}$) |
|---|---|---|---|
| SK-HPg[a] | 1.72 ± 0.06 | 1.79 ± 0.07 | 1.04 |
| SK-HPm[b] | 7.00 ± 1.14 | 0.61 ± 0.09 | 0.09 |
| SK-wt-irHPg[c] | 0.98 ± 0.12 | 4.14 ± 0.52 | 4.22 |
| SK-wt-irHPm[d] | 9.80 ± 1.06 | 2.28 ± 0.23 | 0.32 |
| SK-R561E-HPg | 0.72 ± 0.07 | 7.00 ± 0.84 | 9.72 |
| SK-R561S-HPg | 0.98 ± 0.10 | 3.54 ± 0.36 | 3.61 |
| SK-R561S-HPgΔCHO[e] | 0.49 ± 0.11 | 8.52 ± 1.00 | 17.4 |

[a]Human plasma plasminogen. This complex was formed as a result of preincubation of SK and HPg for 30 sec. The relative percentage of the original HPg remaining at this time in the complex was approximately 80%. Approximately 20% existed as HPm in this complex.
[b]Human plasma plasmin. This complex was formed as a result of preincubation of SK and HPg for 3 min. The relative percentage of HPm in the complex with SK was approximately 100%.
[c]Insect cell-expressed wild-type human plasminogen. This complex was formed as a result of preincubation of SK and wt-irHPg for 30 sec. The relative percentage of the original HPg remaining at this time in the complex was approximately 80%. Approximately 20% existed as HPm in this complex.
[d]Insect cell-expressed wild-type human plasmin. This complex was formed as a result of preincubation of SK and wt-irHPg for 3 min. The relative percentage of HPm in complex with SK was approximately 100%.
[e]Stoichiometric complex of SK with R561S-HPg, deglycosylated at Asn[289].

Comparison of the kinetic properties of the SK-[Lys[78]]Pm (generated with plasma HPg) complex (3-min. preincubation time, Table II) shows that the complex containing the insect-expressed HPm is considerably more active than that containing human plasma HPm, due primarily to a difference in the $k_{cst}$ of activation. Moreover, the second-order specificity constant for plasminogen activation for the SK-R561E-HPg complex was approximately 30-fold greater than the same value for the SK-wt-irHPm complex, due to both a decrease in the $K_m$ and an increase in the $k_{cst}$ values.

From these data and a comparison of the data obtained with the SK-irHPm complex (3-min. preincubation time) and the SK-R561E-HPg complex, it would appear that the complex containing HPg is considerably more effective as a plasminogen activator than that same complex containing HPm. Additional evidence for this view is obtained from analysis of the effect of time of preincubation of stoichiometric levels of SK with both plasma [Glu[1]]Pg and with wt-irHPg on the ability of the resulting complexes to activate BPg.

At very early times of preincubation ($\leq 30$ sec.), SDS/PAGE shows that the complex still contains approximately 80% HPg, in the case of each plasminogen, and approximately 20% HPm. At times of 1 min., and thereafter, all HPg is converted to HPm within the complex. A much higher level of BPg activator activity is present in the 30-sec. sample than in samples preincubated for >1 min., strongly suggesting that the SK-HPg complex is more effective than the SK-HPm complex in activation of BPg.

Kinetic constants for the activation of BPg with the SK complexes prepared from human plasma HPg and wt-irHPg at short preincubation times (30 sec.) are listed in Table II. As seen from these data, the Km values are dramatically decreased from those obtained with the corresponding samples wherein all HPg was converted to HPm within the complexes (compare the data for the 30-sec. and 3-in. preincubation times in Table II). When similar experiments were performed with R561E-HPg and R561S-HPg, no such early time activity peak was noted; only temporally constant activator activities of the complexes were observed.

Finally, the mammalian-cell expressed variant HPg (R561S-HPg), in stoichiometric complex with SK, possessed similar, but not identical, steady-state kinetic values toward BPg activation as the insect-expressed protein (R561E-HPg). The $k_{cat}$ for the enzyme complex containing this latter protein is approximately 2-fold higher than that of the complex formed with the former HPg. That difference in glycosylation of the variant recombinant HPg preparations may play a role in the plasminogen activator activities of the SK complexes containing these same plasminogens can be observed from the data of Table II. Thus, the $k_{cat}$ for activation of BPg by the SK-R561S-HPg complex is approximately 2.4-fold lower and the $K_m$ approximately 2-fold higher than the corresponding values for the same complex prepared with the glycopeptidase F-deglycosylated R561S-HPg. These differences were not revealed in analysis of the amidolytic activities of the same complexes (Tale I). Thus, the deglycosylated form of the CHO-expressed variant HPg, in equimolar complex with SK, allowed the complex to become an even more sufficient activator of BPg.

It should be noted that all kinetic assays contained EACA as a buffer component. This agent was present to provide maximal activation rates and to eliminate any consideration of possible differences in activation rates being due to variable amounts of [Glu$^1$]Pg and [Lys$^{78}$]Pg in the assay mixtures with any of the plasminogens examined herein.

In conclusion, it has been shown that stabilization of HPg within the SK complex results in a greatly increased ability of the complex to activate plasminogen. In addition, stable forms of plasminogen have now been expressed in mammalian cells, enabling efficient preparation of plasminogen that is stable when complexed to streptokinase. In addition, such expression avoids using as the source of plasminogen human plasma, which carries a risk of containing detrimental human viruses such as HIV, HTLV-I, hepatitis, including non-A, non-B hepatitis virus, etc.

EXAMPLE 5

Complexes formed between fibrinoytic enzymes and plasminogen may be used as thrombolytic agents. The catalytic site of fibrinolytic enzymes may be blocked by a group that is removable by hydrolysis under certain conditions. Smith et al., U.S. Pat. No. 4,808,405, supra; and Smith et al, Nature, 290: 505-508 (1981). Therefore, R561E-HPg or R561S-HPg of this invention may be employed as a thrombolytic agent alone, as a complex with a fibrinolytic enzyme, as a complex with an acylated fibrinolytic enzyme, as an acylated proenzyme, or as an acylated proenzyme in a complex with a fibrinolytic enzyme or an acylated fibrinolytic enzyme. An acylated streptokinase/acylated plasminogen complex according to the present invention may be prepared as follows.

Streptokinase (about 451 mg; as available from AB Kabi, Stockholm, Sweden) may be mixed with a lysine/mannitol buffer (about 110 ml) at pH 7.0 and sterile glycerol (about 60 ml) and stirred for 5 minutes 4° C. A sterile filtered solution of p-amidino-phenyl-p'-anisate in DMSO (about 15 ml, about 20 mM) may be added over 2 minutes and the mixture stirred for 5 minutes at 4° C. R561E-HPg or R561S-HPg according to the present invention (about 809 mg) may be added over 2 minutes and the mixture stirred for 60 minutes at 4° C.

A pharmaceutical composition according to the present invention may be prepared from the above as follows: Human serum albumin (clinical grade) (18.9 ml 20% w/v) may be then added to the mixture with stirring for two minutes at 4° C. Lysine/mannitol buffer may be added to bring the volume to about 400 ml. The fluid may then be diafiltered for about 2.5 hours at 18° C. until about 2400 ml of diafiltrate is collected. The fluid may then be filtered through a 0.22 $\mu$ sterile filter and transferred to a sterile reservoir form which aliquots may be dispensed into sterile freeze-drying vials followed by freeze drying.

Deposit of Materials

The following strain has been deposited with the American Type Culture Collection, 12301 Parklawn Drive, Rockville, Md., USA (ATCC):

| Strain | ATCC Accession No. | Deposit Date |
| --- | --- | --- |
| 294/pSV16B5 | 68,151 | October 25, 1989 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture for 30 years form the data of deposit. The organism will be made available by ATCC under the terms of the Budapest Treaty, and subject to an agreement between Genentech, Inc. and ATCC, which assures permanent and unrestricted availability of the progeny of the culture to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if the culture on deposit should die or be lost or destroyed when cultivated under suitable conditions, it will be promptly replaced on notification with a viable specimen of the same culture. Availability of the deposited culture is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the culture deposited, since the deposited embodiments is intended as a separate illustration of certain aspects of the invention and any cultures that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. A human plasminogen (HPg) variant in which the arginine residue at position 561 of native-sequence plasminogen is replaced with another amino acid, which variant is incapable of proteolytic cleavage to its two-chain form and, when in a binary complex with streptokinase, is capable of activating native plasminogen.

2. The plasminogen variant of claim 1 in which the amino acid used to replace arginine is not lycine.

3. The plasminogen variant of claim 2 that is R561E-HPg, R561S-HPg, or R561G-HPg.

4. A pharmaceutical composition for effecting thrombolysis comprising a thrombolytically effective amount of the plasminogen variant of claim 3 in a pharmaceutically acceptable carrier.

5. The composition of claim 4 wherein the plasminogen variant is complexed with streptokinase.

6. The composition of claim 5 wherein the catalytic site essential for fibrinolytic activity is blocked by an acyl group removable by hydrolysis.

7. The composition of claim 6 wherein the complex is a p-anisoyl streptokinase/plasminogen variant complex.

8. The composition of claim 4 that is isotonic.

9. The composition of claim 4 that is sterile filtered.

10. A method for thrombolytic therapy comprising the step of administering to a mammal in need of thrombolytic therapy a thrombolytically effective amount of the composition of claim 5.

11. A method for thrombolytic therapy comprising the step of administering to a mammal in need of thrombolytic therapy a thrombolytically effective amount of the composition of claim 6.

12. The method of claim 11 wherein the composition comprises a p-anisoyl streptokinase/plasminogen variant complex.

13. The method of claim 10 wherein the mammal is human.